(12) United States Patent
Kallander et al.

(10) Patent No.: US 8,859,571 B2
(45) Date of Patent: Oct. 14, 2014

(54) QUINAZOLINE COMPOUNDS

(75) Inventors: Lara S. Kallander, King of Prussia, PA (US); Brian Griffin Lawhorn, King of Prussia, PA (US); Joanne Philp, King of Prussia, PA (US)

(73) Assignee: GlaxoSmithKline LLC, Wilmington, New Castle, DE (US)

( * ) Notice: Subject to any disclaimer, the term of this patent is extended or adjusted under 35 U.S.C. 154(b) by 59 days.

(21) Appl. No.: 13/505,324

(22) PCT Filed: Nov. 1, 2010

(86) PCT No.: PCT/US2010/054927
§ 371 (c)(1),
(2), (4) Date: May 1, 2012

(87) PCT Pub. No.: WO2011/056740
PCT Pub. Date: May 12, 2011

(65) Prior Publication Data
US 2012/0220588 A1 Aug. 30, 2012

Related U.S. Application Data

(60) Provisional application No. 61/257,646, filed on Nov. 3, 2009.

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC ......... 514/266.2; 544/283; 544/284; 544/291

(58) Field of Classification Search
USPC ............... 514/259, 266.2; 544/283, 284, 291
See application file for complete search history.

(56) References Cited

U.S. PATENT DOCUMENTS

| | | | |
|---|---|---|---|
| 6,015,814 A * | 1/2000 | Barker | 514/266.2 |
| 2007/0054928 A1 | 3/2007 | Bannen et al. | |
| 2007/0259904 A1 | 11/2007 | Noronha et al. | |

* cited by examiner

*Primary Examiner* — Paul V. Ward
(74) *Attorney, Agent, or Firm* — Duke M. Fitch; John Lemanowicz; William Majarian

(57) ABSTRACT

Disclosed are compounds having the formula: wherein $R^1$, $R^2$, $R^3$, $R^4$, $R^5$, $R^6$ and $R^7$ are as defined herein, and methods of making and using the same.

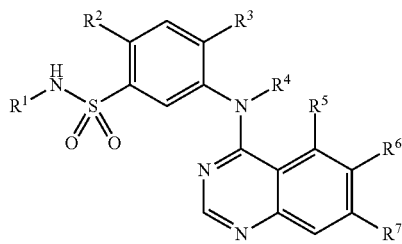

16 Claims, No Drawings

QUINAZOLINE COMPOUNDS

This application is a §371 of International Application No. PCT/US2010/054927, filed 01 Nov. 2010, which claims the benefit of U.S. Provisional Application No. 61/257,646, filed 03 Nov. 2009, which are incorporated herein in their entireties.

FIELD OF THE INVENTION

The present invention relates to compounds that inhibit TNNI3K and methods of making and using the same. Specifically, the present invention relates to quinazolines as TNNI3K inhibitors.

BACKGROUND OF THE INVENTION

Cardiac troponin I-interacting kinase (TNNI3K), also known as CARK (for cardiac ankyrin repeat kinase), is a protein kinase that exhibits highly selective expression for cardiac tissues and has been shown to interact with components of the sarcomere, including troponin I (Zhao, Y. et al., *J. Mol. Med.*, 2003, 81, 297-304; Feng, Y. et al., *Gen. Physiol. Biophys.*, 2007, 26, 104-109; Wang, H. et al., *J. Cell. Mol. Med.*, 2008, 12, 304-315). Although substrates for TNNI3K have not been identified to date, recent reports suggest that this protein does play a role in the development of pressure-induced cardiomyocyte hypertrophy and contractile dysfunction (Wheeler, F. C. et al., *Mamm. Genome*, 2005, 16, 414-423; Wang, X. et al. "TNNI3K, a cardiac-specific kinase, promotes cardiac hypertrophy in vivo", Poster presentation at the 2006 Scientific Sessions of the American Heart Association, Chicago, Ill., Wheeler, F. C. et al., *PLos Genet*, 2009, 5(9), e1000647; and Pu, W. T., *PLos Genet*, 2009, 5(9), e1000643). Inhibition of the kinase activity of TNNI3K may disrupt these signaling pathways, and enable the mitigation and/or reversal of cardiac hypertrophy seen in patients with progressively worsening heart failure.

In response to mechanical, neurohormonal, and genetic stimuli, the heart will undergo hypertrophy, or muscle growth and remodeling, in order to maintain sufficient cardiac output to meet tissue oxygen demands. While these structural changes are initially seen as compensatory, sustained dysregulation of hypertrophic signaling can lead to heart failure, the pathophysiogical state in which the heart can no longer adequately function as a pump (Mudd, J. O. and Kass, D. A., *Nature*, 2008, 451, 919-928). Prevention or reversal of pathological cardiac hypertrophy has the potential to delay or prevent the development of congestive heart failure (McKinsey, T. A. and Kass, D. A., *Nat. Rev. Drug Discov.*, 2007, 6, 617-635; Kaye, D. M. and Krum, H., *Nat. Rev. Drug Discov.*, 2007, 6, 127-139).

Heart failure is responsible for a reduced quality of life and premature death in a significant proportion of sufferers, and is characterized by impaired cardiac function either due to reduced pump function (systolic dysfunction) or reduced filling (diastolic dysfunction). Congestive heart failure (CHF) is characterized by impaired left ventricular function, increased peripheral and pulmonary vascular resistance and reduced exercise tolerance and dyspnea. The prevalence of heart failure is anticipated to increase with aging populations, prompting a need for new and improved methods of treating heart failure.

SUMMARY OF THE INVENTION

The invention is directed to novel quinazolines. Specifically, the invention is directed to a compound according to Formula I:

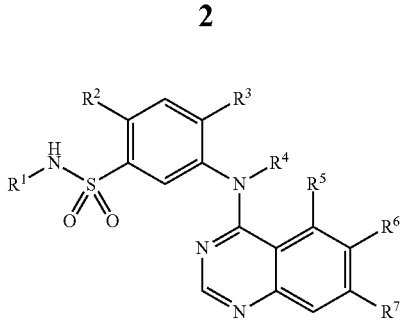

wherein:
$R^1$ is $(C_1-C_4)$alkyl;
$R^2$ is H or halogen;
$R^3$ is H, halogen, $(C_1-C_8)$alkyl, $(C_1-C_8)$haloalkyl, hydroxyl, hydroxy$(C_1-C_8)$alkyl-, $(C_1-C_8)$alkoxy, $(C_3-C_8)$cycloalkyloxy, $(C_1-C_8)$haloalkoxy, $(C_1-C_8)$alkylthio-, $(C_1-C_8)$haloalkylthio-, $(C_3-C_8)$cycloalkylthio-, $(C_1-C_8)$alkylsulfonyl, $(C_1-C_8)$haloalkylsulfonyl, $(C_3-C_8)$cycloalkylsulfonyl, phenyl, 5-membered heteroaryl, or —N($R^a$)($R^b$), wherein said phenyl or heteroaryl is optionally substituted one to three times, independently, by halogen, $(C_1-C_6)$alkyl, $(C_1-C_4)$haloalkyl, $(C_1-C_6)$alkoxy, $(C_1-C_4)$haloalkoxy, hydroxy$(C_1-C_4)$alkyl-, or —N($R^a$)($R^b$);

each $R^a$ is independently $(C_1-C_4)$alkyl, wherein said $(C_1-C_4)$alkyl is optionally substituted one to three times, independently, by halogen, hydroxyl, $(C_1-C_6)$alkoxy, amino, $(C_1-C_6)$alkylamino, $((C_1-C_6)$alkyl$)((C_1-C_6)$alkyl$)$amino, —$CO_2H$, —$CO_2(C_1-C_6)$alkyl, —$CONH_2$, —$CONH(C_1-C_6)$alkyl, or —$CON((C_1-C_6)$alkyl$)((C_1-C_6)$alkyl$)$, and $R^b$ is $(C_1-C_4)$alkyl;
or $R^a$ and $R^b$ taken together with the nitrogen atom to which they are attached form a 5-membered or 6-membered heterocyclic ring, optionally containing one additional heteroatom selected from nitrogen, oxygen and sulfur, wherein said ring is optionally substituted one or two times, independently, by halogen, $(C_1-C_4)$alkyl, $(C_1-C_4)$haloalkyl, amino, $(C_1-C_4)$alkylamino, $((C_1-C_4)$alkyl$)((C_1-C_4)$alkyl$)$amino, hydroxyl, hydroxy$(C_1-C_4)$alkyl-, oxo, $(C_1-C_4)$alkoxy, $(C_1-C_4)$haloalkoxy, or $(C_1-C_4)$alkoxy$(C_1-C_4)$alkyl;

$R^4$ is H;
$R^5$, $R^6$, and $R^7$ are each, independently, H, halogen, nitro, amino, $(C_1-C_4)$alkylamino, $((C_1-C_4)$alkyl$)((C_1-C_4)$alkyl$)$amino, hydroxyl, or $OR^c$; and each $R^c$ is, independently, $(C_1-C_8)$alkyl or a 5-6 membered heterocycloalkyl, wherein said $(C_1-C_8)$alkyl is optionally substituted one to three times, independently, by halogen, hydroxyl, $(C_1-C_4)$alkoxy, amino, $(C_1-C_4)$alkylamino, or —N($R^a$)($R^b$);

or $R^6$ and $R^7$ taken together represent —$O(C_1-C_2)$alkylO—;

or a salt, particularly a pharmaceutically acceptable salt, thereof.

The compounds of the invention are inhibitors of TNNI3K and can be useful for the treatment of cardiac diseases and disorders, particularly heart failure. Accordingly, the invention is further directed to pharmaceutical compositions comprising a compound of the invention. The invention is still further directed to methods of inhibiting TNNI3K and treatment of conditions associated therewith using a compound of the invention or a pharmaceutical composition comprising a compound of the invention.

DETAILED DESCRIPTION OF THE INVENTION

As used herein, the term "alkyl" represents a saturated, straight or branched hydrocarbon moiety, which may be unsubstituted or substituted by one, or more of the substituents defined herein. Exemplary alkyls include, but are not limited to methyl (Me), ethyl (Et), propyl, isopropyl, butyl, isobutyl, t-butyl and pentyl. The term "$C_1$-$C_4$" refers to an alkyl containing from 1 to 4 carbon atoms.

When the term "alkyl" is used in combination with other substituent groups, such as "haloalkyl" or "hydroxyalkyl" or "arylalkyl", the term "alkyl" is intended to encompass a divalent straight or branched-chain hydrocarbon radical. For example, "arylalkyl" is intended to mean the radical—alkyl-aryl, wherein the alkyl moiety thereof is a divalent straight or branched-chain carbon radical and the aryl moiety thereof is as defined herein, and is represented by the bonding arrangement present in a benzyl group (—$CH_2$-phenyl).

As used herein, the term "cycloalkyl" refers to a non-aromatic, saturated, cyclic hydrocarbon ring. The term "($C_3$-$C_8$)cycloalkyl" refers to a non-aromatic cyclic hydrocarbon ring having from three to eight ring carbon atoms. Exemplary "($C_3$-$C_8$)cycloalkyl" groups useful in the present invention include cyclopropyl, cyclobutyl, cyclopentyl, cyclohexyl, cycloheptyl, and cyclooctyl.

"Alkoxy" refers to a group containing an alkyl radical attached through an oxygen linking atom. The term "($C_1$-$C_4$) alkoxy" refers to a straight- or branched-chain hydrocarbon radical having at least 1 and up to 4 carbon atoms attached through an oxygen linking atom. Exemplary "($C_1$-$C_4$) alkoxy" groups useful in the present invention include, but are not limited to, methoxy, ethoxy, n-propoxy, isopropoxy, n-butoxy, s-butoxy, and t-butoxy.

"Alkylthio-" refers to a group containing an alkyl radical attached through a sulfur linking atom. The term "($C_1$-$C_4$) alkylthio-" refers to a straight- or branched-chain hydrocarbon radical having at least 1 and up to 4 carbon atoms attached through a sulfur linking atom. Exemplary "($C_1$-$C_4$)alkylthio-" groups useful in the present invention include, but are not limited to, methylthio-, ethylthio-, n-propylthio-, isopropylthio-, n-butylthio-, s-butylthio-, and t-butylthio-.

"Alkylsulfonyl" refers to a group containing an alkyl radical attached through a sulfonyl radical (i.e. —S(=O)$_2$—). The term "($C_1$-$C_4$)alkylsulfonyl" refers to a straight- or branched-chain hydrocarbon radical having at least 1 and up to 4 carbon atoms attached through a sulfonyl radical. Exemplary "($C_1$-$C_4$)alkylsulfonyl" groups useful in the present invention include, but are not limited to, methanesulfonyl, ethanesulfonyl, propanesulfonyl, and butanesulfonyl.

"Cycloalkyloxy" and "cycloalkylthio" refers to a group containing a saturated carbocyclic ring atoms attached through an oxygen or sulfur linking atom, respectively. Examples of "cycloalkyloxy" moieties include, but are not limited to, cyclopropoxy, cyclobutoxy, cyclopentyloxy, cyclohexyloxy, and the like.

"Aryl" represents a group or moiety comprising an aromatic, monovalent monocyclic or bicyclic hydrocarbon radical containing from 6 to 10 carbon ring atoms, which may be unsubstituted or substituted by one or more of the substituents defined herein, and to which may be fused one or more cycloalkyl rings, which may be unsubstituted or substituted by one or more substituents defined herein.

Generally, in the compounds of this invention, aryl is phenyl.

Heterocyclic groups may be heteroaryl or heterocycloalkyl groups.

"Heterocycloalkyl" represents a group or moiety comprising a non-aromatic, monovalent monocyclic or bicyclic radical, which is saturated or partially unsaturated, containing 3 to 10 ring atoms, which includes 1 to 4 heteroatoms selected from nitrogen, oxygen and sulfur, and which may be unsubstituted or substituted by one or more of the substituents defined herein. Illustrative examples of heterocycloalkyls include, but are not limited to, azetidinyl, pyrrolidyl (or pyrrolidinyl), piperidinyl, piperazinyl, morpholinyl, tetrahydro-4H-1,4-thiazinyl, tetrahydrofuryl (or tetrahydrofuranyl), dihydrofuryl, oxazolinyl, thiazolinyl, pyrazolinyl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl and 1,5,9-triazacyclododecyl.

Generally, in the compounds of this invention, heterocycloalkyl groups are 5-membered and/or 6-membered heterocycloalkyl groups, such as pyrrolidyl (or pyrrolidinyl), tetrahydrofuryl (or tetrahydrofuranyl), tetrahydrothienyl, dihydrofuryl, oxazolinyl, thiazolinyl, pyrazolinyl, piperidyl (or piperidinyl), piperazinyl, morpholinyl, tetrahydropyranyl, dihydropyranyl, 1,3-dioxanyl, tetrahydro-4H-1,4-thiazinyl, 1,4-dioxanyl, 1,3-oxathianyl, and 1,3-dithianyl.

"Heteroaryl" represents a group or moiety comprising an aromatic monovalent monocyclic or bicyclic radical, containing 5 to 10 ring atoms, including 1 to 4 heteroatoms selected from nitrogen, oxygen and sulfur, which may be unsubstituted or substituted by one or more of the substituents defined herein. This term also encompasses bicyclic heterocyclic-aryl compounds containing an aryl ring moiety fused to a heterocycloalkyl ring moiety, containing 5 to 10 ring atoms, including 1 to 4 heteroatoms selected from nitrogen, oxygen and sulfur, which may be unsubstituted or substituted by one or more of the substituents defined herein. Illustrative examples of heteroaryls include, but are not limited to, thienyl, pyrrolyl, imidazolyl, pyrazolyl, furyl (or furanyl), isothiazolyl, isoxazolyl, oxazolyl, oxadiazolyl, thiazolyl, pyridyl (or pyridinyl), pyrazinyl, pyrimidinyl, pyridazinyl, triazinyl, tetrazinyl, triazolyl, tetrazolyl, benzo[b]thienyl, isobenzofuryl, 2,3-dihydrobenzofuryl, chromenyl, chromanyl, indolizinyl, isoindolyl, indolyl, indazolyl, purinyl, isoquinolyl, quinolyl, phthalazinyl, naphthridinyl, quinazolinyl, benzothiazolyl, benzimidazolyl, tetrahydroquinolinyl, cinnolinyl, pteridinyl, and isothiazolyl.

Generally, the heteroaryl groups present in the compounds of this invention are 5-membered and/or 6-membered monocyclic heteroaryl groups. Selected 5-membered heteroaryl groups contain one nitrogen, oxygen or sulfur ring heteroatom, and optionally contain 1, 2 or 3 additional nitrogen ring atoms. Selected 6-membered heteroaryl groups contain 1, 2, 3 or 4 nitrogen ring heteroatoms. Selected 5- or 6-membered heteroaryl groups include thienyl, pyrrolyl, imidazolyl, pyrazolyl, furyl, isothiazolyl, isoxazolyl, oxazolyl, oxadiazolyl, thiazolyl, triazolyl, tetrazolyl, pyridyl, pyrazinyl, pyrimidinyl, pyridazinyl, and triazinyl.

"Oxo" represents a double-bonded oxygen moiety; for example, if attached directly to a carbon atom forms a carbonyl moiety (C=O).

The terms "halogen" and "halo" represent chloro, fluoro, bromo or iodo substituents. "Hydroxy" or "hydroxyl" is intended to mean the radical —OH.

As used herein, the term "compound(s) of the invention" means a compound of formula (I) (as defined above) in any form, i.e., any salt or non-salt form (e.g., as a free acid or base form, or as a pharmaceutically acceptable salt thereof) and any physical form thereof (e.g., including non-solid forms (e.g., liquid or semi-solid forms), and solid forms (e.g., amorphous or crystalline forms, specific polymorphic forms, solvates, including hydrates (e.g., mono-, di- and hemi-hydrates)), and mixtures of various forms.

As used herein, the term "optionally substituted" means that the groups may be either unsubstituted or substituted with one or more of the specified substituents.

The alternative definitions for the various groups and substituent groups of Formula I provided throughout the specification are intended to particularly describe each compound species disclosed herein, individually, as well as groups of one or more compound species. The scope of this invention includes any combination of these group and substituent group definitions.

The invention is further directed to a compound according to Formula I, wherein:

$R^1$ is $(C_1$-$C_4)$alkyl;
$R^2$ is H or halogen;
$R^3$ is H, halogen, $(C_1$-$C_4)$alkoxy, $(C_5$-$C_6)$cycloalkyloxy, $(C_1$-$C_4)$haloalkoxy, $(C_1$-$C_4)$alkylthio-, $(C_1$-$C_4)$haloalkylthio-, $(C_5$-$C_6)$cycloalkylthio-, $(C_1$-$C_4)$alkylsulfonyl, $(C_1$-$C_4)$haloalkylsulfonyl, $(C_5$-$C_6)$cycloalkylsulfonyl, or —$N(R^a)(R^b)$; each $R^a$ is independently $(C_1$-$C_4)$alkyl, wherein said $(C_1$-$C_4)$alkyl is optionally substituted one to three times, independently, by halogen, hydroxyl, $(C_1$-$C_4)$alkoxy, amino, $(C_1$-$C_4)$alkylamino, $((C_1$-$C_4)$alkyl)$((C_1$-$C_4)$alkyl)amino, —$CO_2H$, —$CO_2(C_1$-$C_4)$alkyl, —$CONH_2$, —$CONH(C_1$-$C_4)$alkyl, or —$CON((C_1$-$C_4)$alkyl)$((C_1$-$C_4)$alkyl), and $R^b$ is $(C_1$-$C_4)$alkyl;

or $R^a$ and $R^b$ taken together with the nitrogen atom to which they are attached form a 5-membered or 6-membered heterocyclic ring, optionally containing one additional heteroatom selected from nitrogen, oxygen and sulfur, wherein said ring is optionally substituted one or two times, independently, by halogen, $(C_1$-$C_4)$alkyl, $(C_1$-$C_4)$haloalkyl, amino, $(C_1$-$C_4)$alkylamino, $((C_1$-$C_4)$alkyl)$((C_1$-$C_4)$alkyl)amino, hydroxyl, hydroxy$(C_1$-$C_4)$alkyl-, oxo, $(C_1$-$C_4)$alkoxy, $(C_1$-$C_4)$haloalkoxy, or $(C_1$-$C_4)$alkoxy$(C_1$-$C_4)$alkyl;

$R^4$ is H;

$R^5$, $R^6$, and $R^7$ are each, independently, H, halogen, nitro, amino, $(C_1$-$C_4)$alkylamino, $((C_1$-$C_4)$alkyl)$((C_1$-$C_4)$alkyl)amino, hydroxyl, or $OR^c$; and each $R^c$ is, independently, $(C_1$-$C_4)$alkyl, pyrrolidinyl, tetrahydrofuranyl, tetrahydrothienyl, piperidinyl, piperazinyl, morpholinyl, tetrahydropyranyl, tetrahydro-4H-1,4-thiazinyl, or 1,4-dioxanyl, wherein said $(C_1$-$C_4)$alkyl is optionally substituted by halogen, hydroxyl, trifluoromethyl, $(C_1$-$C_4)$alkoxy, amino, $(C_1$-$C_4)$alkylamino, $((C_1$-$C_4)$alkyl)$((C_1$-$C_4)$alkyl)amino, pyrrolidinyl, tetrahydrofuranyl, tetrahydrothienyl, piperidinyl, piperazinyl, morpholinyl, tetrahydropyranyl, tetrahydro-4H-1,4-thiazinyl, or 1,4-dioxanyl;

or $R^6$ and $R^7$ taken together represent —$O(C_1$-$C_2)$alkylO—;

or a salt, particularly a pharmaceutically acceptable salt, thereof.

In another embodiment of this invention:

$R^1$ is $(C_1$-$C_4)$alkyl;
$R^2$ is H;
$R^3$ is H, halogen, $(C_1$-$C_8)$alkyl, $(C_1$-$C_8)$haloalkyl, hydroxyl, hydroxy$(C_1$-$C_8)$alkyl-, $(C_1$-$C_8)$alkoxy, $(C_3$-$C_8)$cycloalkyloxy, $(C_1$-$C_8)$haloalkoxy, $(C_1$-$C_8)$alkylthio-, $(C_1$-$C_8)$haloalkylthio-, $(C_3$-$C_8)$cycloalkylthio-, phenyl, 5-membered heteroaryl, or —$N(R^a)(R^b)$, wherein said phenyl or heteroaryl is optionally substituted one to three times, independently, by halogen, $(C_1$-$C_6)$alkyl, $(C_1$-$C_4)$haloalkyl, $(C_1$-$C_6)$alkoxy, $(C_1$-$C_4)$haloalkoxy, hydroxy$(C_1$-$C_4)$alkyl-, or —$N(R^a)(R^b)$;

each $R^a$ is independently $(C_1$-$C_4)$alkyl, wherein said $(C_1$-$C_4)$alkyl is optionally substituted one to three times, independently, by halogen, hydroxyl, $(C_1$-$C_6)$alkoxy, amino, $(C_1$-$C_6)$alkylamino, $((C_1$-$C_6)$alkyl)$((C_1$-$C_6)$alkyl)amino, —$CO_2H$, —$CO_2(C_1$-$C_6)$alkyl, —$CONH_2$, —$CONH(C_1$-$C_6)$alkyl, or —$CON((C_1$-$C_6)$alkyl)$((C_1$-$C_6)$alkyl), and $R^b$ is $(C_1$-$C_4)$alkyl;

or $R^a$ and $R^b$ taken together with the nitrogen atom to which they are attached form a 5-membered or 6-membered heterocyclic ring, optionally containing one additional heteroatom selected from nitrogen, oxygen and sulfur, wherein said ring is optionally substituted one or two times, independently, by halogen, $(C_1$-$C_4)$alkyl, $(C_1$-$C_4)$haloalkyl, amino, $(C_1$-$C_4)$alkylamino, $((C_1$-$C_4)$alkyl)$((C_1$-$C_4)$alkyl)amino, hydroxyl, hydroxy$(C_1$-$C_4)$alkyl-, oxo, $(C_1$-$C_4)$alkoxy, $(C_1$-$C_4)$haloalkoxy, or $(C_1$-$C_4)$alkoxy$(C_1$-$C_4)$alkyl;

$R^4$ is H;
$R^5$ is H;
$R^6$ and $R^7$ are each $OR^c$; and each $R^c$ is, independently, $(C_1$-$C_8)$alkyl, optionally substituted one to three times, independently, by halogen, hydroxyl, $(C_1$-$C_4)$alkoxy, amino, $(C_1$-$C_4)$alkylamino, or $((C_1$-$C_4)$alkyl)$((C_1$-$C_4)$alkyl)amino;

or a salt, particularly a pharmaceutically acceptable salt, thereof.

In another embodiment of this invention:

$R^1$ is $(C_1$-$C_3$ alkyl);
$R^2$ is H;
$R^3$ is H, halogen, $C_1$-$C_6$ alkyl, $C_1$-$C_6$ haloalkyl, hydroxy$C_1$-$C_6$ alkyl-, $C_1$-$C_6$ alkoxy, $(C_3$-$C_6)$cycloalkyloxy, $C_1$-$C_6$ haloalkoxy, $C_1$-$C_6$ alkylthio-, $(C_3$-$C_6)$cycloalkylthio-, $C_1$-$C_6$ haloalkylthio-, phenyl, 5-membered heteroaryl, or —$N(R^a)(R^b)$, wherein said heteroaryl contains one heteroatom selected from N, O and S, or contains one nitrogen atom and optionally contains 1 additional heteroatom selected from N, O and S, or contains two nitrogen atoms and optionally contains 1 additional heteroatom selected from N, O and S; and said phenyl or heteroaryl is optionally substituted one to three times, independently, by halogen, $(C_1$-$C_6)$alkyl, $(C_1$-$C_4)$haloalkyl, or —$N(R^a)(R^b)$;

each $R^a$ is independently $(C_1$-$C_4)$alkyl, wherein said $(C_1$-$C_4)$alkyl is optionally substituted by hydroxyl, trifluoromethyl, $(C_1$-$C_6)$alkoxy, amino, $(C_1$-$C_6)$alkylamino, or $((C_1$-$C_6)$alkyl)$((C_1$-$C_6)$alkyl)amino, and $R^b$ is $(C_1$-$C_4)$alkyl;

or $R^a$ and $R^b$ taken together with the nitrogen atom to which they are attached form a 5-membered or 6-membered heterocyclic ring, optionally containing one additional heteroatom selected from nitrogen, oxygen and sulfur, wherein said ring is optionally substituted one or two times, independently, by $(C_1$-$C_4)$alkyl, $(C_1$-$C_4)$haloalkyl, hydroxy$(C_1$-$C_4)$alkyl-, oxo, or $(C_1$-$C_4)$alkoxy$(C_1$-$C_4)$alkyl;

$R^4$ is H;
$R^5$ is H;
$R^6$ and $R^7$ are each $OR^c$; and each $R^c$ is, independently, $(C_1$-$C_4)$alkyl, optionally substituted one to three times, independently, by halogen;

or a salt, particularly a pharmaceutically acceptable salt, thereof.

In a specific embodiment of this invention, $R^1$ is —$CH_3$.

In another specific embodiment of this invention, $R^2$ is H or F. In a further specific embodiment of this invention, $R^2$ is H.

In another embodiment of the invention, $R^3$ is H, halogen, $(C_1$-$C_6)$alkyl, $(C_1$-$C_6)$haloalkyl, $(C_1$-$C_6)$alkoxy, $(C_5$-$C_6)$cycloalkyloxy, $(C_1$-$C_6)$haloalkoxy, $(C_1$-$C_6)$alkylthio-, $(C_5$-$C_6)$cycloalkylthio-, $(C_1$-$C_6)$haloalkylthio-, $(C_1$-$C_6)$alkylsulfonyl, $(C_1$-$C_6)$haloalkylsulfonyl, $(C_5$-$C_6)$cycloalkylsulfonyl, phenyl, 5-membered heteroaryl, or —$N(R^a)(R^b)$, wherein said heteroaryl contains one heteroatom selected from N, O and S, or contains one nitrogen atom and optionally contains 1 additional heteroatom selected from N, O and S, or contains two nitrogen atoms and optionally contains 1 additional heteroatom selected from N, O and S; and said phenyl or heteroaryl is optionally substituted one to three times, independently, by halogen, $(C_1-C_6)$alkyl, $(C_1-C_4)$haloalkyl, or —N($R^a$)($R^b$).

In a further embodiment of this invention, $R^3$ is H, halogen, $(C_1-C_8)$alkyl, $(C_1-C_8)$haloalkyl, hydroxyl, hydroxy$(C_1-C_8)$alkyl-, $(C_1-C_8)$alkoxy, $(C_3-C_8)$cycloalkyloxy, $(C_1-C_8)$haloalkoxy, $(C_1-C_8)$alkylthio-, $(C_1-C_8)$haloalkylthio-, $(C_3-C_8)$cycloalkylthio-, phenyl, 5-membered heteroaryl, or —N($R^a$)($R^b$), wherein said phenyl or heteroaryl is optionally substituted one to three times, independently, by halogen, $(C_1-C_6)$alkyl, $(C_1-C_4)$haloalkyl, $(C_1-C_6)$alkoxy, $(C_1-C_4)$haloalkoxy, hydroxy$(C_1-C_4)$alkyl-, or —N($R^a$)($R^b$).

In yet a further embodiment of this invention, $R^3$ is H, halogen, $C_1-C_6$ alkyl, $C_1-C_6$ haloalkyl, hydroxy$C_1-C_6$ alkyl-, $C_1-C_6$ alkoxy, $(C_3-C_6)$cycloalkyloxy, $C_1-C_6$ haloalkoxy, $C_1-C_6$ alkylthio-, $(C_3-C_6)$cycloalkylthio-, $C_1-C_6$ haloalkylthio-, phenyl, 5-membered heteroaryl, or —N($R^a$)($R^b$), wherein said heteroaryl contains one heteroatom selected from N, O and S, or contains one nitrogen atom and optionally contains 1 additional heteroatom selected from N, O and S, or contains two nitrogen atoms and optionally contains 1 additional heteroatom selected from N, O and S; and said phenyl or heteroaryl is optionally substituted one to three times, independently, by halogen, $(C_1-C_6)$alkyl, $(C_1-C_4)$haloalkyl, or —N($R^a$)($R^b$).

In yet a further embodiment of this invention, $R^3$ is H, halogen, $(C_1-C_4)$alkoxy, $(C_5-C_6)$cycloalkyloxy, $(C_1-C_4)$haloalkoxy, $(C_1-C_4)$alkylthio-, $(C_1-C_4)$haloalkylthio-, $(C_5-C_6)$cycloalkylthio-, $(C_1-C_4)$alkylsulfonyl, $(C_1-C_4)$haloalkylsulfonyl, $(C_5-C_6)$cycloalkylsulfonyl, or —N($R^a$)($R^b$).

In a specific embodiment of this invention, each $R^a$ is independently —CH$_3$, —CH$_2$CH$_3$, or —CH$_2$CF$_3$, and $R^b$ is —CH$_3$; or $R^a$ and $R^b$ taken together with the nitrogen to which they are attached represent pyrrolidin-1-yl, piperidin-1-yl, or morpholin-4-yl, wherein said pyrrolidin-1-yl, piperidin-1-yl, or morpholin-4-yl is optionally substituted one or two times, independently, by F, —CH$_3$, or —CF$_3$.

In another specific embodiment of this invention, $R^3$ is H, F, Cl, —OCH$_3$, —OCH(CH$_3$)$_2$, —OCF$_3$, —OCH$_2$CF$_3$, —OCH(CH$_3$)CF$_3$, —SCH$_3$, —SCH$_2$CF$_3$, —SO$_2$CH$_3$, —N(CH$_3$)$_2$, —N(CH$_3$)CH$_2$CH$_3$, —N(CH$_3$)CH$_2$CF$_3$, 2-(trifluoromethyl)pyrrolidin-1-yl, 2,5-(dimethyl)pyrrolidin-1-yl, piperidin-1-yl, 4,4-difluoro-piperidin-1-yl, or morpholin-4-yl.

In a further embodiment of this invention, $R^5$, $R^6$, and $R^7$ are each, independently, H, halogen, nitro, amino, $(C_1-C_4)$alkylamino, $((C_1-C_4)$alkyl$)((C_1-C_4)$alkyl$)$amino, hydroxyl, or OR$^c$, and each R$^c$ is, independently, $(C_1-C_4)$alkyl, pyrrolidinyl, tetrahydrofuranyl, tetrahydrothienyl, piperidinyl, piperazinyl, morpholinyl, tetrahydropyranyl, tetrahydro-4H-1,4-thiazinyl, or 1,4-dioxanyl, wherein said $(C_1-C_4)$alkyl is optionally substituted by halogen, hydroxyl, trifluoromethyl, $(C_1-C_4)$alkoxy, amino, $(C_1-C_4)$alkylamino, $((C_1-C_4)$alkyl$)((C_1-C_4)$alkyl$)$amino, pyrrolidinyl, tetrahydrofuranyl, tetrahydrothienyl, piperidinyl, piperazinyl, morpholinyl, tetrahydropyranyl, tetrahydro-4H-1,4-thiazinyl, or 1,4-dioxanyl; or $R^6$ and $R^7$ taken together represent —O($C_1-C_2$)alkylO—.

In a specific embodiment of this invention, $R^5$ is H, Cl, —OCH$_3$, —OCH$_2$CH$_3$, —OCH(CH$_3$)$_2$, —O(CH$_2$)$_2$OCH$_3$, or —O(tetrahydropyran-4-yl).

In another specific embodiment of this invention, $R^5$ is H.

In another embodiment of this invention, $R^6$ and $R^7$ are each OR$^c$; and each R$^c$ is, independently, $(C_1-C_8)$alkyl, optionally substituted one to three times, independently, by halogen, hydroxyl, $(C_1-C_4)$alkoxy, amino, $(C_1-C_4)$alkylamino, or $((C_1-C_4)$alkyl$)((C_1-C_4)$alkyl$)$amino.

In a further embodiment of this invention, $R^6$ and $R^7$ are each OR$^c$; and each R$^c$ is, independently, $(C_1-C_4)$alkyl, optionally substituted one to three times, independently, by halogen.

In yet a further embodiment of this invention, $R^6$ and $R^7$ are each OR$^c$; and each R$^c$ is, independently, $(C_1-C_4)$alkyl, optionally substituted by $(C_1-C_4)$alkoxy.

In a specific embodiment of this invention, $R^6$ is H, Cl, I, —OCH$_3$, —OCH$_2$CH$_3$, —OCH(CH$_3$)$_2$, —O(CH$_2$)$_2$OCH$_3$, —O(CH$_2$)$_3$-morpholin-4-yl, —NH$_2$, —NHCH$_3$, or —N(CH$_3$)$_2$.

In another specific embodiment of this invention, $R^6$ is H.

In another specific embodiment of this invention, $R^7$ is H, —OH, —OCH$_3$, —OCH$_2$CH$_3$, —OCH(CH$_3$)$_2$, —O(CH$_2$)$_3$Cl, —O(CH$_2$)$_2$OCH$_3$, —O(CH$_2$)$_3$OCH$_3$, —O(CH$_2$)$_3$-morpholin-4-yl, —NH$_2$, —NHCH$_3$, or —NO$_2$.

In another specific embodiment of this invention, $R^6$ and $R^7$ taken together represent —O(CH$_2$)$_2$O—.

Specific compounds of this invention are:

3-{[6,7-bis(methyloxy)-4-quinazolinyl]amino}-4-(dimethylamino)-N-methylbenzenesulfonamide;

3-{[6,7-bis(methyloxy)-4-quinazolinyl]amino}-N-methylbenzenesulfonamide;

3-{[6,7-bis(methyloxy)-4-quinazolinyl]amino}-N-methyl-4-(4-morpholinyl)benzenesulfonamide;

3-{[6,7-bis(methyloxy)-4-quinazolinyl]amino}-4-[ethyl(methyl)amino]-N-methylbenzenesulfonamide;

3-{[6,7-bis(methyloxy)-4-quinazolinyl]amino}-N-methyl-4-[(1-methylethyl)oxy]benzenesulfonamide;

3-{[6,7-bis(methyloxy)-4-quinazolinyl]amino}-N-methyl-4-(methyloxy)benzenesulfonamide;

3-{[6,7-bis(methyloxy)-4-quinazolinyl]amino}-N-methyl-4-(methylthio)benzenesulfonamide;

4-(dimethylamino)-N-methyl-3-(4-quinazolinylamino)benzenesulfonamide;

3-[(6-chloro-4-quinazolinyl)amino]-4-(dimethylamino)-N-methylbenzenesulfonamide;

4-(dimethylamino)-N-methyl-3-{[6-(methyloxy)-4-quinazolinyl]amino}benzenesulfonamide;

3-{[6,7-bis(methyloxy)-4-quinazolinyl]amino}-N-methyl-4-[(2,2,2-trifluoroethyl)oxy]benzenesulfonamide;

3-[(6-chloro-4-quinazolinyl)amino]-N-methyl-4-[(2,2,2-trifluoroethyl)oxy]benzenesulfonamide;

3-(7,8-dihydro[1,4]dioxino[2,3-g]quinazolin-4-ylamino)-4-(dimethylamino)-N-methylbenzenesulfonamide;

3-{[6,7-bis(methyloxy)-4-quinazolinyl]amino}-4-(4,4-difluoro-1-piperidinyl)-N-methylbenzenesulfonamide;

3-[(6-chloro-4-quinazolinyl)amino]-4-(4,4-difluoro-1-piperidinyl)-N-methylbenzenesulfonamide;

3-({7-[(3-chloropropyl)oxy]-4-quinazolinyl}amino)-4-(dimethylamino)-N-methylbenzenesulfonamide;

3-[(6,7-bis{[2-(methyloxy)ethyl]oxy}-4-quinazolinyl)amino]-4-(dimethylamino)-N-methylbenzenesulfonamide;

3-[(6,7-bis{[2-(methyloxy)ethyl]oxy}-4-quinazolinyl)amino]-N-methyl-4-(methyloxy)benzenesulfonamide;

3-[(6,7-bis{[2-(methyloxy)ethyl]oxy}-4-quinazolinyl)amino]-N-methyl-4-[(2,2,2-trifluoroethyl)oxy]benzenesulfonamide;

3-[(6,7-bis{[2-(methyloxy)ethyl]oxy}-4-quinazolinyl)amino]-N-methyl-4-(methylthio)benzenesulfonamide;

3-{[6,7-bis(methyloxy)-4-quinazolinyl]amino}-N-methyl-4-[(2R)-2-(trifluoromethyl)-1-pyrrolidinyl]benzenesulfonamide;
3-[(6-chloro-4-quinazolinyl)amino]-N-methyl-4-[(2R)-2-(trifluoromethyl)-1-pyrrolidinyl]benzenesulfonamide;
5-{[6,7-bis(methyloxy)-4-quinazolinyl]amino}-2-fluoro-N-methylbenzenesulfonamide;
3-{[6,7-bis(methyloxy)-4-quinazolinyl]amino}-N-methyl-4-[(trifluoromethyl)oxy]benzenesulfonamide;
3-{[6,7-bis(methyloxy)-4-quinazolinyl]amino}-N-methyl-4-(1-piperidinyl)benzenesulfonamide;
3-[(6-chloro-4-quinazolinyl)amino]-N-methyl-4-(1-piperidinyl)benzenesulfonamide;
3-{[6,7-bis(methyloxy)-4-quinazolinyl]amino}-4-(2,5-dimethyl-1-pyrrolidinyl)-N-methylbenzenesulfonamide;
3-[(6-chloro-4-quinazolinyl)amino]-4-(2,5-dimethyl-1-pyrrolidinyl)-N-methylbenzenesulfonamide;
3-{[6,7-bis(methyloxy)-4-quinazolinyl]amino}-N-methyl-4-[(2,2,2-trifluoroethyl)thio]benzenesulfonamide;
3-{[5,7-bis(methyloxy)-4-quinazolinyl]amino}-N-methylbenzenesulfonamide;
3-{[5,7-bis(methyloxy)-4-quinazolinyl]amino}-N-methyl-4-[(2,2,2-trifluoroethyl)oxy]benzenesulfonamide;
3-{[5,7-bis(methyloxy)-4-quinazolinyl]amino}-4-(dimethylamino)-N-methylbenzenesulfonamide;
3-(5-chloro-6,7-dimethoxyquinazolin-4-ylamino)-N-methylbenzenesulfonamide;
4-methoxy-3-(7-methoxy-6-(3-morpholinopropoxy)quinazolin-4-ylamino)-N-methylbenzenesulfonamide;
3-{[6,7-bis(methyloxy)-4-quinazolinyl]amino}-N-methyl-4-[methyl(2,2,2-trifluoroethyl)amino]benzenesulfonamide;
3-{[5,7-bis(methyloxy)-4-quinazolinyl]amino}-N-methyl-4-[methyl(2,2,2-trifluoroethyl)amino]benzenesulfonamide;
3-{[5,7-bis(methyloxy)-4-quinazolinyl]amino}-N-methyl-4-(methyloxy)benzenesulfonamide;
3-{[5,7-bis(methyloxy)-4-quinazolinyl]amino}-4-fluoro-N-methylbenzenesulfonamide;
3-{[5,7-bis(methyloxy)-4-quinazolinyl]amino}-4-chloro-N-methylbenzenesulfonamide;
3-{[5,7-bis(methyloxy)-4-quinazolinyl]amino}-N-methyl-4-(4-morpholinyl)benzenesulfonamide;
5-{[6,7-bis(methyloxy)-4-quinazolinyl]amino}-2-fluoro-N-methyl-4-(methyloxy)benzenesulfonamide;
3-{[6-(ethyloxy)-7-(methyloxy)-4-quinazolinyl]amino}-N-methyl-4-[(2,2,2-trifluoroethyl)oxy]benzenesulfonamide;
4-(dimethylamino)-3-(7-methoxy-6-(3-morpholinopropoxy)quinazolin-4-ylamino)-N-methylbenzenesulfonamide;
N-methyl-3-{[6-[(1-methylethyl)oxy]-7-(methyloxy)-4-quinazolinyl]amino}-4-[(2,2,2-trifluoroethyl)oxy]benzenesulfonamide;
3-({7-[(3-chloropropyl)oxy]-4-quinazolinyl}amino)-N-methyl-4-[(2,2,2-trifluoroethyl)oxy]benzenesulfonamide;
3-{[5-(ethyloxy)-7-(methyloxy)-4-quinazolinyl]amino}-N-methyl-4-[(2,2,2-trifluoroethyl)oxy]benzenesulfonamide;
N-methyl-3-{[5-[(1-methylethyl)oxy]-7-(methyloxy)-4-quinazolinyl]amino}-4-[(2,2,2-trifluoroethyl)oxy]benzenesulfonamide;
N-methyl-4-[(2,2,2-trifluoroethyl)oxy]-3-{[5, 6, 7-tris(methyloxy)-4-quinazolinyl]amino}benzenesulfonamide;
3-{[5,7-bis(methyloxy)-4-quinazolinyl]amino}-N-methyl-4-[(2,2,2-trifluoro-1-methylethyl)oxy]benzenesulfonamide;
5-{[5,7-bis(methyloxy)-4-quinazolinyl]amino}-2-fluoro-N-methyl-4-[(2,2,2-trifluoroethyl)oxy]benzenesulfonamide;
5-{[5,7-bis(methyloxy)-4-quinazolinyl]amino}-2-fluoro-N-methyl-4-(methyloxy)benzenesulfonamide;
5-{[6,7-bis(methyloxy)-4-quinazolinyl]amino}-2-fluoro-N-methyl-4-[(2,2,2-trifluoroethyl)oxy]benzenesulfonamide;
3-{[5,7-bis(methyloxy)-4-quinazolinyl]amino}-N-methyl-4-(methylthio)benzenesulfonamide;
3-{[5,7-bis(methyloxy)-4-quinazolinyl]amino}-N-methyl-4-[(trifluoromethyl)oxy]benzenesulfonamide;
N-methyl-4-[(trifluoromethyl)oxy]-3-{[5, 6,7-tris(methyloxy)-4-quinazolinyl]amino}benzenesulfonamide;
5-{[5,7-bis(methyloxy)-4-quinazolinyl]amino}-4-(dimethylamino)-2-fluoro-N-methylbenzenesulfonamide;
5-{[6,7-bis(methyloxy)-4-quinazolinyl]amino}-4-(dimethylamino)-2-fluoro-N-methylbenzenesulfonamide;
2-fluoro-N-methyl-4-[(2,2,2-trifluoroethyl)oxy]-5-{[5,6,7-tris(methyloxy)-4-quinazolinyl]amino}benzenesulfonamide;
4-chloro-N-methyl-3-{[5,6,7-tris(methyloxy)-4-quinazolinyl]amino}benzenesulfonamide;
N-methyl-3-[(7-(methyloxy)-5-{[2-(methyloxy)ethyl]oxy}-4-quinazolinyl)amino]-4-[(2,2,2-trifluoroethyl)oxy]benzenesulfonamide;
N-methyl-3-{[7-(methyloxy)-5-(tetrahydro-2H-pyran-4-yloxy)-4-quinazolinyl]amino}-4-[(2,2,2-trifluoroethyl)oxy]benzenesulfonamide;
N-methyl-4-[(2,2,2-trifluoro-1-methylethyl)oxy]-3-{[5,6,7-tris(methyloxy)-4-quinazolinyl]amino}benzesulfonamide;
N-methyl-4-(methylsulfonyl)-3-{[5,6,7-tris(methyloxy)-4-quinazolinyl]amino}benzenesulfonamide;
3-{[5-(ethyloxy)-7-(methyloxy)-4-quinazolinyl]amino}-N-methyl-4-[(trifluoromethyl)oxy]benzenesulfonamide;
N-methyl-3-{[5-[(1-methylethyl)oxy]-7-(methyloxy)-4-quinazolinyl]amino}-4-[(trifluoromethyl)oxy]benzenesulfonamide;
3-{[5-(ethyloxy)-7-(methyloxy)-4-quinazolinyl]amino}-N-methyl-4-[(2,2,2-trifluoro-1-methylethyl)oxy]benzenesulfonamide;
N-methyl-3-{[5-[(1-methylethyl)oxy]-7-(methyloxy)-4-quinazolinyl]amino}-4-[(2,2,2-trifluoro-1-methylethyl)oxy]benzenesulfonamide;
3-{[6,7-bis(methyloxy)-4-quinazolinyl]amino}-N-methyl-4-(methylsulfonyl)benzenesulfonamide;
3-{[6,7-bis(methyloxy)-4-quinazolinyl]amino}-N-methyl-4-[(2,2,2-trifluoro-1-methylethyl)oxy]benzenesulfonamide;
3-{[6-iodo-7-(methyloxy)-4-quinazolinyl]amino}-N-methyl-4-[(2,2,2-trifluoroethyl)oxy]benzenesulfonamide;
3-{[6,7-bis(ethyloxy)-4-quinazolinyl]amino}-N-methyl-4-[(2,2,2-trifluoroethyl)oxy]benzenesulfonamide;
4-(dimethylamino)-N-methyl-3-((7-nitroquinazolin-4-yl)amino)benzenesulfonamide;
4-(dimethylamino)-N-methyl-3-[(7-{[3-(4-morpholinyl)propyl]oxy}-4-quinazolinyl)amino]benzenesulfonamide;
N-methyl-3-[(7-{[3-(4-morpholinyl)propyl]oxy}-4-quinazolinyl)amino]-4-[(2,2,2-trifluoroethyl)oxy]benzenesulfonamide;
N-methyl-3-[(7-{[3-(methyloxy)propyl]oxy}-4-quinazolinyl)amino]-4-[(2,2,2-trifluoroethyl)oxy]benzenesulfonamide;
4-(dimethylamino)-N-methyl-3-[(7-{[3-(methyloxy)propyl]oxy}-4-quinazolinyl)amino]benzenesulfonamide;
3-{[5,7-bis(methyloxy)-4-quinazolinyl]amino}-N-methyl-4-(methylsulfonyl)benzenesulfonamide;
3-(7-hydroxy-6-methoxyquinazolin-4-ylamino)-N-methyl-4-(2,2,2-trifluoroethoxy)benzenesulfonamide;

3-(7-isopropoxy-6-methoxy-quinazolin-4-ylamino)-N-methyl-4-(2,2,2-trifluoro-ethoxy)-benzenesulfonamide;

3-(7-ethoxy-6-methoxy-quinazolin-4-ylamino)-N-methyl-4-(2,2,2-trifluoro-ethoxy)-benzenesulfonamide;

3-[6-methoxy-7-(2-methoxy-ethoxy)-quinazolin-4-ylamino]-N-methyl-4-(2,2,2-trifluoro-ethoxy)-benzenesulfonamide;

3-{[5,7-bis(methyloxy)-4-quinazolinyl]amino}-N-methyl-4-[(2,2,2-trifluoro-1-methylethyl)oxy]benzenesulfonamide;

3-{[5,7-bis(methyloxy)-4-quinazolinyl]amino}-N-methyl-4-[(2,2,2-trifluoro-1-methylethyl)oxy]benzenesulfonamide;

3-((6-aminoquinazolin-4-yl)amino)-4-(dimethylamino)-N-methylbenzenesulfonamide;

3-((7-aminoquinazolin-4-yl)amino)-4-(dimethylamino)-N-methylbenzenesulfonamide;

4-(dimethylamino)-3-((6-(dimethylamino)quinazolin-4-yl)amino)-N-methylbenzenesulfonamide;

4-(dimethylamino)-N-methyl-3-((6-(methylamino)quinazolin-4-yl)amino)benzenesulfonamide; and 4-(dimethylamino)-N-methyl-3-((7-(methylamino)quinazolin-4-yl)amino)benzenesulfonamide;

and salts, particularly pharmaceutically acceptable salts, thereof.

Representative compounds of this invention include the compounds of Examples 1-88.

The compounds according to Formula I may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, is not specified the structure is intended to encompass all individual stereoisomers and all mixtures thereof. Thus, compounds according to Formula I containing one or more chiral center may be used as racemic mixtures, enantiomerically enriched mixtures, or as enantiomerically pure individual stereoisomers.

Individual stereoisomers of a compound according to Formula I which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

For solvates of the compounds of the invention, or salts thereof, that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

Because of their potential use in medicine, the salts of the compounds of Formula I are preferably pharmaceutically acceptable. The compounds of this invention are bases, wherein a desired salt form may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycollates, tartrates mandelates, and sulfonates, such as xylenesulfonates, methanesulfonates, propanesulfonates, naphthalene-1-sulfonates and naphthalene-2-sulfonates.

If an inventive basic compound is isolated as a salt, the corresponding free base form of that compound may be prepared by any suitable method known to the art, including treatment of the salt with an inorganic or organic base, suitably an inorganic or organic base having a higher $pK_a$ than the free base form of the compound.

General Methods of Preparation

The compounds of Formula I may be obtained by using synthetic procedures illustrated in the Schemes below or by drawing on the knowledge of a skilled organic chemist. The synthesis provided in these Schemes are applicable for producing compounds of the invention having a variety of different $R^1$ and $R^2$ groups employing appropriate precursors, which are suitably protected if needed, to achieve compatibility with the reactions outlined herein. Subsequent deprotection, where needed, affords compounds of the nature generally disclosed. While the Schemes are shown with compounds only of Formula I, they are illustrative of processes that may be used to make the compounds of the invention.

Compound names were generated using the software naming program ACD/Name Pro V6.02 available from Advanced Chemistry Development, Inc., 110 Yonge Street, 14$^{th}$ Floor, Toronto, Ontario, Canada, M5C 1T4 (http://www.acdlabs.com/).

As shown in Scheme 1, the compounds of Formula I can be prepared under a variety of conditions by reaction of an arylamine (e.g., Ar—NH—$R^2$, specifically, Ar—NH$_2$) with an activated quinazoline.

Scheme 1

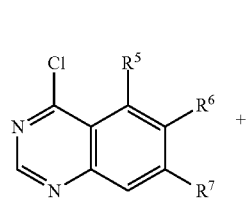

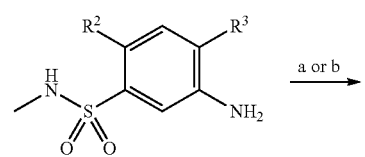

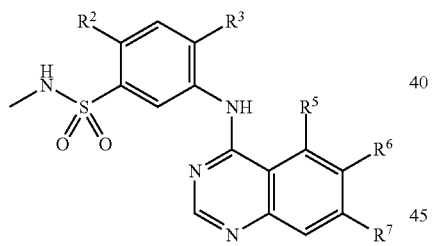

a) Isopropanol, μW (6-15 bar), 150° C., 15 min; b) Isopropanol, μw (1-2 bar), 100° C., 30 min As shown in Schemes 2-5, the compounds of Formula I can be prepared via common functional group transformations on advanced intermediates.

Scheme 2

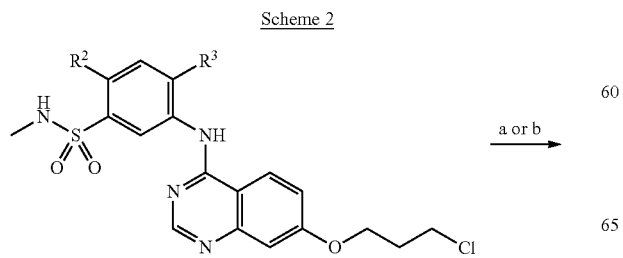

-continued

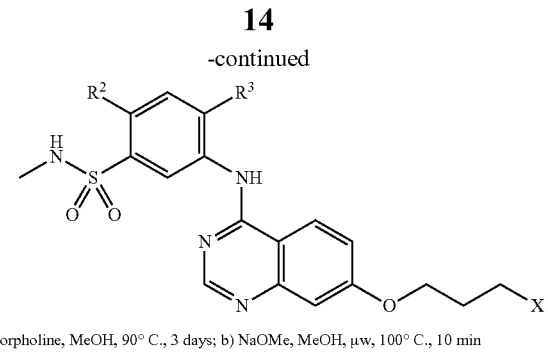

a) morpholine, MeOH, 90° C., 3 days; b) NaOMe, MeOH, μw, 100° C., 10 min

Scheme 3

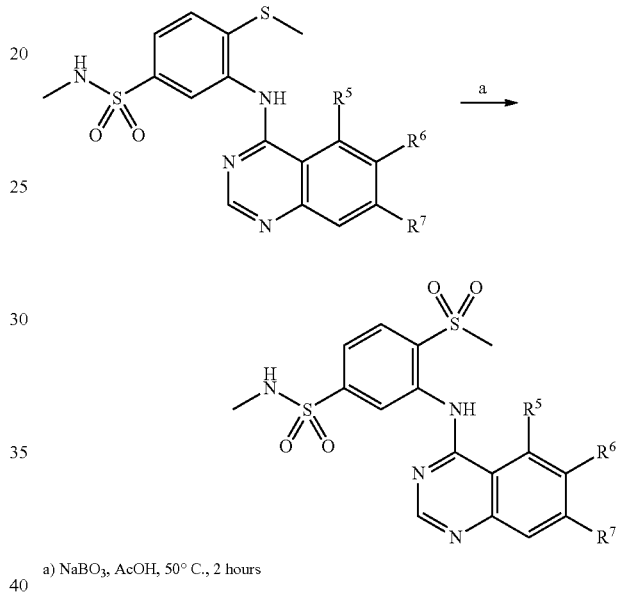

a) NaBO$_3$, AcOH, 50° C., 2 hours

Scheme 4

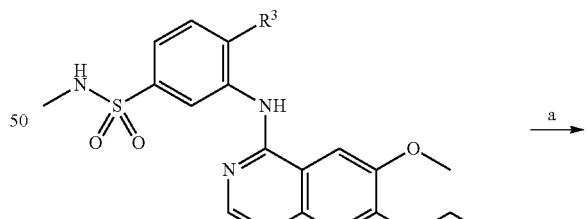

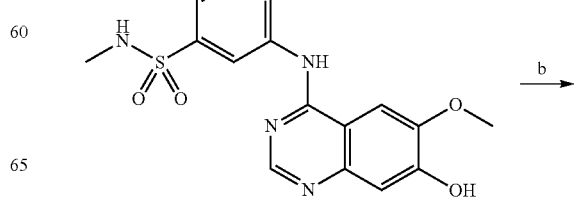

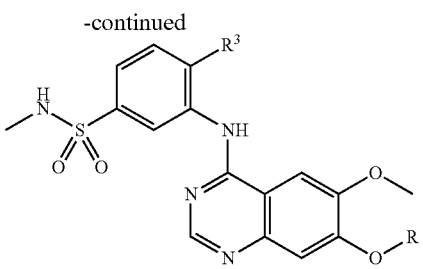

a) H₂, Pd/C, AcOH, EtOAc, MeOH, DMF, 25° C., 2 hours;
b) RBr, K₂CO₃, DMF, 60° C., 16 hours Scheme 5

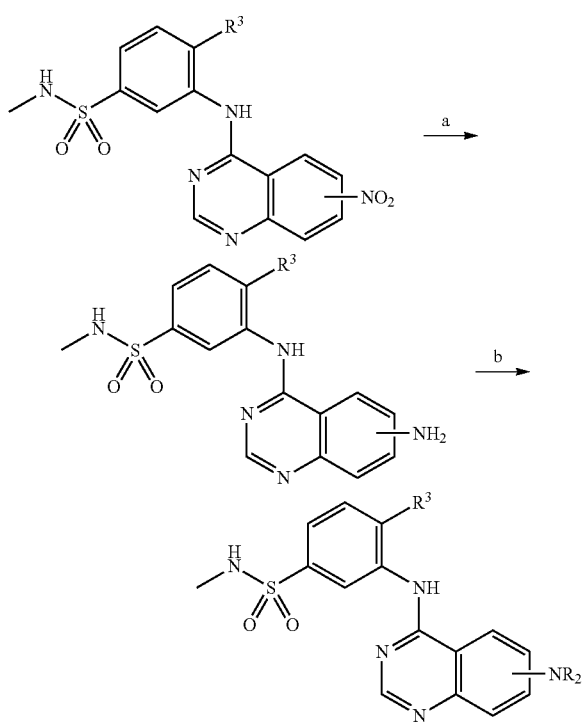

a) H₂, Pd/C, MeOH, 25° C., 2.5 hours;
b) H₂CO, NaBH(OAc)₃, AcOH, CH₂Cl₂, 25° C., 2 hours The invention also includes various deuterated forms of the compounds of Formula I. Each available hydrogen atom attached to a carbon atom may be independently replaced with a deuterium atom. A person of ordinary skill in the art will know how to synthesize deuterated forms of the compounds of Formula I. For example, deuterated alkyl groups (e.g., N-(deuteromethyl)amines or $R^a/R^b$ alkyls) may be prepared by conventional techniques (see for example: methyl-d₃-amine available from Aldrich Chemical Co., Milwaukee, Wis., Cat. No. 489,689-2). Employing such compounds according to Scheme 1 will allow for the preparation of compounds of Formula I in which various hydrogen atoms of the N-methyl or pyrimidinyl groups are replaced with a deuterium atom.

Methods of Use

The present invention is directed to a method of inhibiting TNNI3K which comprises contacting the kinase with a compound of Formula I or a salt thereof, particularly a pharmaceutically acceptable salt thereof. This invention is also directed to a method of treatment of a TNNI3K-mediated disease or disorder comprising administering an effective amount of the compound of Formula I or a salt thereof, particularly a pharmaceutically acceptable salt thereof, to a patient, specifically a human, in need thereof. As used herein, "patient" refers to a human or other mammal. Specifically, this invention is directed to a method of inhibiting TNNI3K activity, comprising contacting the kinase with an effective amount of a compound of Formula I or a pharmaceutically acceptable salt thereof. For example, TNNI3K activity may be inhibited in mammalian cardiac tissue by administering to a patient in need thereof, an effective amount a compound of Formula I or a pharmaceutically acceptable salt thereof.

The compounds of this invention may be particularly useful for treatment of TNNI3K-mediated diseases or disorders, specifically by inhibition of TNNI3K activity, where such diseases or disorders are selected from heart failure, particularly congestive heart failure; cardiac hypertrophy; and heart failure or congestive heart failure resulting from cardiac hypertrophy. The compounds of this invention may also be useful for the treatment of heart failure or congestive heart failure resulting from myocardial ischemia or myocardial infarction.

A therapeutically "effective amount" is intended to mean that amount of a compound that, when administered to a patient in need of such treatment, is sufficient to effect treatment, as defined herein. Thus, e.g., a therapeutically effective amount of a compound of Formula I, or a pharmaceutically acceptable salt thereof, is a quantity of an inventive agent that, when administered to a human in need thereof, is sufficient to modulate or inhibit the activity of TNNI3K such that a disease condition which is mediated by that activity is reduced, alleviated or prevented. The amount of a given compound that will correspond to such an amount will vary depending upon factors such as the particular compound (e.g., the potency ($pXC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmaceutical characteristics), disease or condition and its severity and the specific composition and method being used, but can nevertheless be determined by one of skill in the art.

"Treating" or "treatment" is intended to mean at least the mitigation of a disease condition in a patient, where the disease condition is caused or mediated by TNNI3K. The methods of treatment for mitigation of a disease condition include the use of the compounds in this invention in any conventionally acceptable manner, for example for prevention, retardation, prophylaxis, therapy or cure of a disease. The compounds of Formula I of this invention may be useful for the treatment of heart failure, particularly congestive heart failure. The compounds of Formula I of this invention may be useful for the treatment of cardiac hypertrophy, and heart failure or congestive heart failure resulting from cardiac hypertrophy, myocardial ischemia or myocardial infarction.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Treatment of TNNI3K-mediated disease conditions may be achieved using the compounds of this invention as a monotherapy, or in dual or multiple combination therapy, such as in combination with other cardiovascular agents, for example, in combination with one or more of the following agents: a beta-blocker, an ACE inhibitor, an angiotensin receptor blocker (ARB), a calcium channel blocker, a diuretic, a renin inhibitor, a centrally acting antihypertensive, a dual ACE/NEP inhibitor, an aldosterone synthase inhibitor, and an aldosterone-receptor antagonist, which are administered in effective amounts as is known in the art.

Examples of suitable beta blockers include timolol (such as BLOCARDEN™) carteolol (such as CARTROL™), carvedilol (such as COREG™), nadolol (such as CORGARD™), propanolol (such as INNOPRAN XL™), betaxolol (such as KERLONE™) penbutolol (such as LEVATOL™), metoprolol (such as LOPRESSOR™ and TOPROL-XL™), atenolol (such as TENORMIN™), pindolol (such as VISKEN™), bisoprolol, bucindolol, esmolol, acebutolol, labetalol, nebivolol, celiprolol, sotalol, and oxprenolol. Examples of suitable ACE inhibitors include alacepril, benazepril, benazaprilat, captopril, ceronapril, cilazapril, delapril, enalapril, enalaprilat, fosinopril, lisinopril, moexipiril, moveltopril, perindopril, quinapril, quinaprilat, ramipril, ramiprilat, spirapril, temocapril, trandolapril, and zofenopril. Preferred ACE inhibitors are benazepril, enalpril, lisinopril, and ramipril. Examples of suitable angiotensin receptor blockers include candesartan, eprosartan, irbesartan, losartan, olmesartan, tasosartan, telmisartan, and valsartan. Examples of suitable calcium channel blockers include dihydropyridines (DHPs) and non-DHPs. Suitable DHPs include amlodipine, felodipine, ryosidine, isradipine, lacidipine, nicardipine, nifedipine, nigulpidine, niludipine, nimodiphine, nisoldipine, nitrendipine, and nivaldipine, and their pharmaceutically acceptable salts. Suitable non-DHPs are flunarizine, prenylamine, diltiazem, fendiline, gallopamil, mibefradil, anipamil, tiapamil, and verampimil, and their pharmaceutically acceptable salts. A suitable diuretic is a thiazide derivative selected from amiloride, chlorothiazide, hydrochlorothiazide, methylchlorothiazide, and chlorothalidon. A suitable renin inhibitor is aliskiren. Examples of suitable centrally acting antihypertensives include clonidine, guanabenz, guanfacine and methyldopa. Examples of suitable dual ACE/NEP inhibitors include omapatrilat, fasidotril, and fasidotrilat. Examples of suitable aldosterone synthase inhibitors include anastrozole, fadrozole, and exemestane. Examples of suitable aldosterone-receptor antagonists include spironolactone and eplerenone.

The invention further includes the use of compounds of the invention as an active therapeutic substance, in particular in the treatment of diseases mediated by TNNI3K. Specifically, the invention includes the use of compounds of the invention in the treatment of heart failure, particularly congestive heart failure; cardiac hypertrophy; heart failure or congestive heart failure resulting from cardiac hypertrophy; and heart failure or congestive heart failure resulting from myocardial ischemia or myocardial infarction.

In another aspect, the invention includes the use of compounds of the invention in the manufacture of a medicament for use in the treatment of the above disorders.

Compositions

The compounds of the invention will normally, but not necessarily, be formulated into a pharmaceutical composition prior to administration to a patient. Accordingly, in another aspect the invention is directed to pharmaceutical compositions comprising a compound of the invention and a pharmaceutically-acceptable excipient.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. For oral application, for example, one or more tablets or capsules may be administered. A dose of the pharmaceutical composition contains at least a therapeutically effective amount of a compound of this invention (i.e., a compound of Formula I or a salt, particularly a pharmaceutically acceptable salt, thereof). When prepared in unit dosage form, the pharmaceutical compositions may contain from 1 mg to 1000 mg of a compound of this invention.

The pharmaceutical compositions of the invention typically contain one compound of the invention. However, in certain embodiments, the pharmaceutical compositions of the invention contain more than one compound of the invention. In addition, the pharmaceutical compositions of the invention may optionally further comprise one or more additional pharmaceutically active compounds.

As used herein, "pharmaceutically-acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically-acceptable are avoided. In addition, each excipient must of course be of sufficiently high purity to render it pharmaceutically-acceptable.

The compounds of the invention and the pharmaceutically-acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in Remington's *Pharmaceutical Sciences* (Mack Publishing Company).

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

In the following experimental descriptions, the following abbreviations may be used:

| Abbreviation | Meaning |
|---|---|
| aq | aqueous |
| brine | saturated aqueous sodium chloride |
| $CH_2Cl_2$ | methylene chloride |
| $CH_3CN$ or MeCN | acetonitrile |
| $CH_3SNa$ | sodium methyl mercaptide |
| d | day |
| DMF | N,N-dimethylformamide |
| DMSO | dimethylsulfoxide |
| equiv | equivalents |
| Et | ethyl |
| $Et_3N$ or TEA | triethylamine |
| $Et_2O$ | diethyl ether |
| EtOAc | ethyl acetate |
| h, hr | hour |
| HCl | hydrochloric acid |
| i-$Pr_2$NEt | N',N'-diisopropylethylamine |
| LCMS | liquid chromatography-mass spectroscopy |
| Me | methyl |
| MeOH or $CH_3OH$ | methanol |
| $MgSO_4$ | magnesium sulfate |
| min | minute |
| MS | mass spectrum |
| μw | microwave |
| NaH | sodium hydride |
| $NaHCO_3$ | sodium bicarbonate |
| $Na_2SO_4$ | sodium sulfate |
| $NH_4Cl$ | ammonium chloride |
| Pd/C | palladium on carbon |
| Ph | phenyl |
| rt | room temperature |
| satd | saturated |
| SPE | solid phase extraction |
| TFA | trifluoroacetic acid |
| THF | tetrahydrofuran |
| $t_R$ | retention time |

Preparation 1

4-fluoro-N-methyl-3-nitrobenzenesulfonamide

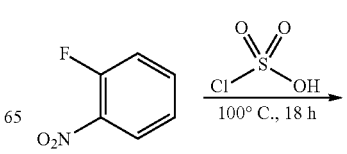

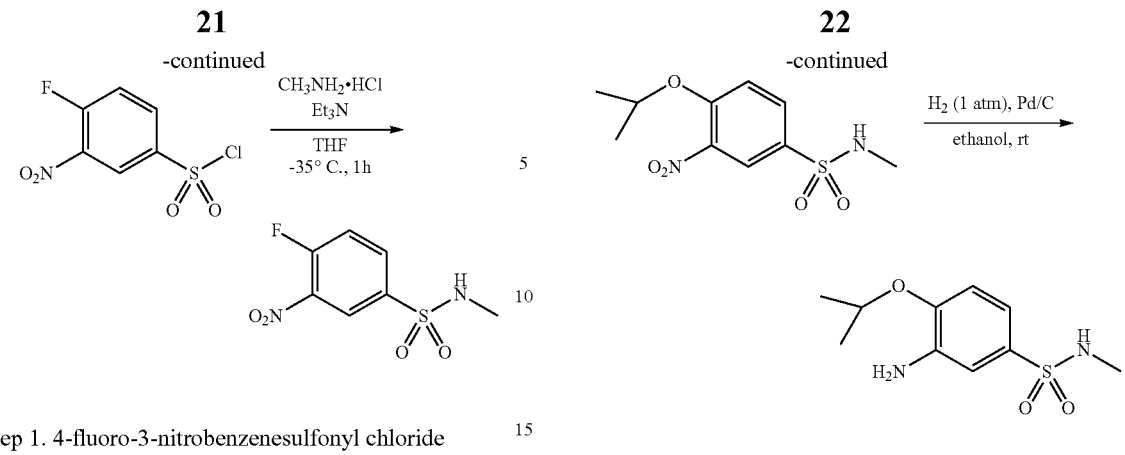

Step 1. 4-fluoro-3-nitrobenzenesulfonyl chloride

1-Fluoro-2-nitrobenzene (50.0 g, 0.354 mol) was added to chlorosulfonic acid (91 g, 0.778 mol) at 65° C. The resulting mixture was then heated to 100° C. for 18 h. The mixture was cooled to room temperature, poured over ice and extracted with methylene chloride. The combined organic layers were then washed with NaHCO$_3$, then brine, dried over MgSO$_4$, filtered and concentrated in vacuo to afford 4-fluoro-3-nitrobenzenesulfonyl chloride (55.3 g, 65% yield) as a brown oil.

Step 2. 4-fluoro-N-methyl-3-nitrobenzenesulfonamide

To a solution of 4-fluoro-3-nitrobenzenesulfonyl chloride (43 g, 179.5 mmol) in THF (500 mL), was added triethylamine (150 mL, 1.08 mol). The mixture was cooled to −35° C. and methylamine hydrochloride (14.5 g, 215.4 mmol) in water was added dropwise. After 1 h, the mixture was warmed to room temperature and diluted with 1:1 water/ethyl acetate. The organic layer was separated and washed with saturated aqueous sodium bicarbonate, then brine, dried over MgSO$_4$, filtered and concentrated in vacuo. The crude residue was purified via column chromatography (20% ethyl acetate/petroleum ether) to give 4-fluoro-N-methyl-3-nitrobenzenesulfonamide (38 g, 90% yield) as a yellow solid.

Preparation 2

3-amino-N-methyl-4-[(1-methylethyl)oxy]benzenesulfonamide

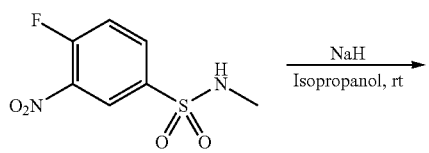

Step 1. N-methyl-4-[(1-methylethyl)oxy]-3-nitrobenzenesulfonamide

NaH (0.440 g, 11 mmol) was added to 20 mL of isopropanol and the resulting mixture stirred at room temperature. After 30 minutes, 4-fluoro-N-methyl-3-nitrobenzenesulfonamide (2.34 g, 10 mmol) was added. The reaction mixture was then stirred at room temperature overnight. The mixture was poured into EtOAc and water. The organic phase was separated, dried over Na$_2$SO$_4$, and concentrated in vacuo to give the crude product. Purification via column chromatography (1:1 petroleum ether/ethyl acetate) afforded N-methyl-4-[(1-methylethyl)oxy]-3-nitrobenzenesulfonamide (1.6 g, 58% yield) as a yellow solid. MS (m/z) 274.7 (M+H$^+$)

Step 2. 3-amino-N-methyl-4-[(1-methylethyl)oxy]benzenesulfonamide

To a mixture of N-methyl-4-[(1-methylethyl)oxy]-3-nitrobenzenesulfonamide (1.6 g, 5.8 mmol) in ethanol (20 mL) under nitrogen, Pd/C (0.160 g) was added. The flask was then evacuated and recharged with hydrogen three times. The resulting mixture was allowed to stir under a hydrogen atmosphere overnight at room temperature. The mixture was then filtered and concentrated to afford 3-amino-N-methyl-4-[(1-methylethyl)oxy]benzenesulfonamide (1.1 g, 77%) as a white solid. $^1$H NMR (400 MHz, DMSO-d$_6$) δ 7.01-7.10 (m, 2H), 6.87-6.98 (m, 2H), 5.08 (br. s., 2H), 4.63 (dt, J=5.93, 11.98 Hz, 1H), 2.34-2.41 (m, 3H), 1.29 (d, J=6.02 Hz, 6H); MS (m/z) 244.7 (M+H$^+$)

The following anilines were prepared from 4-fluoro-N-methyl-3-nitrobenzenesulfonamide using procedures analogous to those described in Preparation 2:

| Aniline Product | Conditions for Step 1 | MS (m/z) | $^1$H NMR |
|---|---|---|---|
| 3-amino-N-methyl-4-(methyloxy)benzenesulfonamide | sodium methoxide, methanol | 217.0 (M + H$^+$) | $^1$H NMR (400 MHz, DMSO-d$_6$) δ 7.09 (q, J = 4.85 Hz, 1H), 7.03 (s, 1H), 6.94 (s, 2H), 5.18 (s, 2H), 3.83 (s, 3H), 2.36 (d, J = 5.02 Hz, 3H) |

| Aniline Product | Conditions for Step 1 | MS (m/z) | $^1$H NMR |
|---|---|---|---|
| 3-amino-N-methyl-4-[(2,2,2-trifluoroethyl)oxy]benzenesulfonamide | NaH, 2,2,2-trifluoroethanol | 285.0 (M + H$^+$) | $^1$H NMR (400 MHz, DMSO-d$_6$) δ ppm 7.18 (q, J = 5.02 Hz, 1 H), 7.05-7.13 (m, 2 H), 6.93 (dd, J = 8.53, 2.26 Hz, 1 H), 5.25 (s, 2 H), 4.81 (q, J = 8.87 Hz, 2 H), 2.38 (d, J = 4.77 Hz, 3 H) |
| 3-amino-N-methyl-4-[(2,2,2-trifluoro-1-methylethyl)oxy]benzenesulfonamide | NaH, 1,1,1-trifluoro-2-propanol | 299.0 (M + H$^+$) | $^1$H NMR (400 MHz, DMSO-d$_6$) δ ppm 7.14-7.22 (m, 2 H), 7.11 (d, J = 2.26 Hz, 1 H), 6.92 (dd, J = 8.41, 2.38 Hz, 1 H), 5.19-5.30 (m, 3 H), 2.39 (d, J = 5.02 Hz, 3 H), 1.45 (d, J = 6.27 Hz, 3 H) |

Preparation 3

3-amino-N-methyl-4-(methylthio)benzenesulfonamide

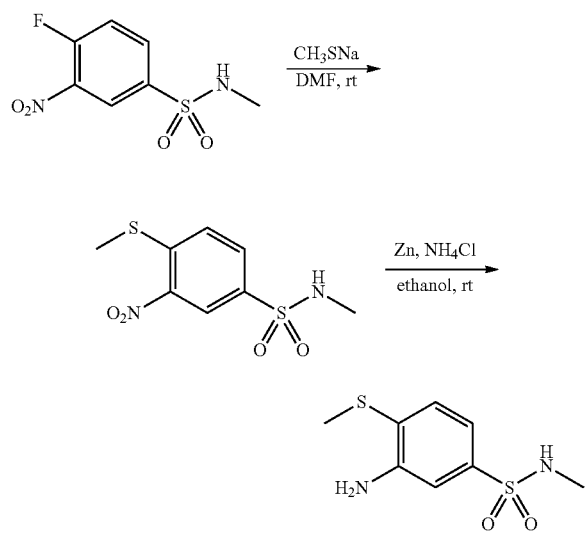

Step 1.
N-methyl-4-(methylthio)-3-nitrobenzenesulfonamide

To a solution of 4-fluoro-N-methyl-3-nitrobenzenesulfonamide (15 g, 64.01 mmol) in THF (150 mL), was added 20% CH$_3$SNa (22.4 g, 64.01 mmol) dropwise. The resulting mixture was then stirred overnight. In the morning, the mixture was poured into ethyl acetate and water, the organic phase separated, dried over Na$_2$SO$_4$, filtered and concentrated. The crude material was then purified via column chromatography (1:1 ethyl acetate/petroleum ether) to afford N-methyl-4-(methylthio)-3-nitrobenzenesulfonamide (3.29 g, 19%) as a yellow solid. MS (m/z) 262.7 (M+H$^+$)

Step 2.
3-amino-N-methyl-4-(methylthio)benzenesulfonamide

To a solution of N-methyl-4-(methylthio)-3-nitrobenzenesulfonamide (1.0 g, 3.81 mmol) in 10 mL of ethanol and 10 mL of NH$_4$Cl, zinc dust (2.5 g, 3.81 mmol) was added. The reaction mixture was stirred overnight at room temperature. The mixture was then filtered and diluted with ethyl acetate and water. The organic phase was separated, washed with water and brine, dried over MgSO$_4$, filtered and concentrated to afford 3-amino-N-methyl-4-(methylthio)benzenesulfonamide (0.500 g, 56%) as a white solid. $^1$H NMR (400 MHz, DMSO-d$_6$) δ 7.06 (d, J=8.03 Hz, 1H), 6.86 (s, 1H), 6.67-6.76 (m, 1H), 5.28 (br. s., 2H), 2.17 (s, 3H), 2.21 (s, 3H); MS (m/z) 232.7 (M+H$^+$)

The following anilines were prepared from 4-fluoro-N-methyl-3-nitrobenzenesulfonamide using procedures analogous to those described in Preparation 3:

| Aniline Product | Conditions | MS (m/z) | $^1$H NMR |
|---|---|---|---|
| 3-amino-N-methyl-4-[(2,2,2-trifluoroethyl)thio]benzenesulfonamide | Step 1: 2,2,2-trifluoroethanethiol, NaH<br>Step 2: NiCl$_2$, NaBH$_4$, MeOH | 300.7 (M + H$^+$) | $^1$H NMR (400 MHz, DMSO-d$_6$) δ ppm 7.48 (d, J = 7.94 Hz, 1 H), 7.33 (q, J = 5.00 Hz, 1 H), 7.14 (d, J = 1.98 Hz, 1 H), 6.85 (dd, J = 8.05, 2.09 Hz, 1 H), 5.87 (s, 2 H), 3.72 (q, J = 10.36 Hz, 2 H), 2.39 (d, J = 5.07 Hz, 3 H) |

Preparation 4

3-amino-N-methyl-4-(4-morpholinyl)benzenesulfonamide

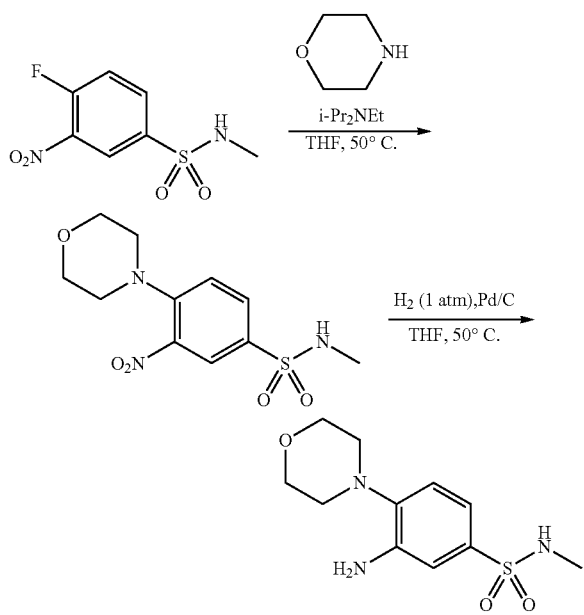

Step 1. N-methyl-4-(4-morpholinyl)-3-nitrobenzenesulfonamide

To a solution of 4-fluoro-N-methyl-3-nitrobenzenesulfonamide (2.00 g, 8.54 mmol) and morpholine (0.744 g, 8.54 mmol) in THF (100 mL), was added N,N-diisopropylethylamine (2.21 g, 17.08 mmol). The resulting solution was stirred at 50° C. overnight. In the morning, the reaction mixture was cooled to room temperature and concentrated to dryness in vacuo. The residue was dissolved in ethyl acetate and washed with water and brine, dried over $MgSO_4$, filtered and concentrated in vacuo to obtain N-methyl-4-(4-morpholinyl)-3-nitrobenzenesulfonamide (2.5 g, 97%) as a red oil. MS (m/z) 302.0 $(M+H^+)$

Step 2. 3-amino-N-methyl-4-(4-morpholinyl)benzenesulfonamide

To a mixture of N-methyl-4-(4-morpholinyl)-3-nitrobenzenesulfonamide (2.5 g, 8.30 mmol) in THF (100 mL) under nitrogen, Pd/C (0.8 g) was added. The flask was then evacuated and recharged with hydrogen three times. The resulting mixture was allowed to stir under a hydrogen atmosphere at 50° C. overnight. The mixture was then filtered and concentrated to afford 3-amino-N-methyl-4-(4-morpholinyl)benzenesulfonamide (1.98 g, 88%). $^1$H NMR (400 MHz, DMSO-$d_6$) δ 7.07-7.17 (m, 2H), 7.01 (d, J=8.28 Hz, 1H), 6.94 (dd, J=1.88, 8.16 Hz, 1H), 5.20 (s, 2H), 3.72-3.81 (m, 4H), 2.80-2.89 (m, 4H), 2.38 (d, J=4.77 Hz, 3H); MS (m/z) 272.2 $(M+H^+)$ The following anilines were prepared from 4-fluoro-N-methyl-3-nitrobenzenesulfonamide and the indicated amine using the procedures described in Preparation 4:

| Aniline Product | Amine/ Conditions in Step 1 | MS (m/z) | $^1$H NMR |
| --- | --- | --- | --- |
| 3-amino-4-(dimethylamino)-N-methylbenzenesulfonamide | dimethyl amine | 230.2 $(M + H^+)$ | $^1$H NMR (400 MHz, DMSO-$d_6$) δ 7.03-7.10 (m, 2H), 7.00 (d, J = 8.28 Hz, 1H), 6.93 (dd, J = 2.13, 8.16 Hz, 1H), 5.13 (s, 2H), 2.62 (s, 6H), 2.38 (d, J = 5.02 Hz, 3H) |
| 3-amino-4-[ethyl(methyl)amino]-N-methylbenzenesulfonamide | ethyl(methyl)amine | 244.1 $(M + H^+)$ | $^1$H NMR (400 MHz, DMSO-$d_6$) δ 7.06-7.13 (m, 2H), 7.02 (d, J = 8.28 Hz, 1H), 6.93 (dd, J = 1.76, 8.03 Hz, 1H), 5.11 (s, 2H), 2.89 (q, J = 7.03 Hz, 2H), 2.60 (s, 3H), 2.39 (d, J = 5.02 Hz, 3H), 1.03 (t, J = 7.03 Hz, 3H) |
| 3-amino-4-(4,4-difluoro-1-piperidinyl)-N-methylbenzenesulfonamide | 4,4-difluoropiperidine | 306.1 $(M + H^+)$ | $^1$H NMR (400 MHz, DMSO-$d_6$) δ ppm 7.15 (br. s., 1 H), 7.10 (d, J = 2.01 Hz, 1 H), 7.05 (d, J = 8.28 Hz, 1 H), 6.92 (dd, J = 8.16, 2.13 Hz, 1 H), 5.29 (s, 2 H), 2.95 (t, J = 4.77 Hz, 4 H), 2.39 (s, 3 H), 2.10-2.25 (m, 4 H) |
| 3-amino-N-methyl-4-[(2R)-2-(trifluoromethyl)-1-pyrrolidinyl]benzenesulfonamide | (2R)-2-(trifluoromethyl)pyrrolidine (conditions: dioxane, 110° C., sealed tube) | 324.1 $(M + H^+)$ | $^1$H NMR (400 MHz, DMSO-$d_6$) δ ppm 7.31 (d, J = 8.28 Hz, 1 H), 7.13-7.22 (m, 1 H), 7.10 (d, J = 2.26 Hz, 1 H), 6.91 (dd, J = 8.28, 2.26 Hz, 1 H), 5.20 (s, 2 H), 4.40-4.53 (m, 1 H), 3.49-3.59 (m, 1 H), 2.64-2.78 (m, 1 H), 2.42 (s, 3 H), 2.27-2.37 (m, 1 H), 1.84-2.04 (m, 3 H) |
| 3-amino-N-methyl-4-(1-piperidinyl)benzenesulfonamide | piperidine | 270.1 $(M + H^+)$ | $^1$H NMR (400 MHz, DMSO-$d_6$) δ ppm 7.11 (br. s., 1 H), 7.08 (d, J = 2.01 Hz, 1 H), 6.99 (d, J = 8.28 Hz, 1 H), 6.91-6.96 (m, 1 H), 5.09 (s, 2 H), 2.74-2.86 (m, 4 H), 2.38 (s, 3 H), 1.64-1.72 (m, 4H), 1.48-1.58 (m, 2 H) |

| Aniline Product | Amine/ Conditions in Step 1 | MS (m/z) | $^1$H NMR |
|---|---|---|---|
| 3-amino-4-(2,5-dimethyl-1-pyrrolidinyl)-N-methylbenzenesulfonamide | 2,5-dimethylpyrrolidine | 284.1 (M + H$^+$) | $^1$H NMR (400 MHz, DMSO-d$_6$) δ ppm 7.29 (d, J = 8.03 Hz, 1 H), 7.19 (br. s., 1 H), 7.09 (d, J = 2.26 Hz, 1 H), 6.92 (dd, J = 8.16, 2.13 Hz, 1 H), 5.38 (s, 2 H), 3.04-3.14 (m, 2 H), 2.41 (s, 3 H), 1.95-2.07 (m, 2 H), 1.42-1.55 (m, 2 H), 0.88 (d, J = 6.02 Hz, 6 H) |

Preparation 5

3-amino-4-fluoro-N-methylbenzenesulfonamide

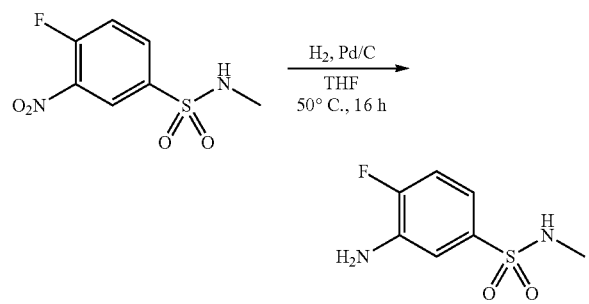

To a mixture of 4-fluoro-N-methyl-3-nitrobenzenesulfonamide (1.6 g, 6.83 mmol) in THF (50 mL) under nitrogen, Pd/C (0.600 g) was added. The flask was then evacuated and recharged with hydrogen. The resulting mixture was allowed to stir under a hydrogen atmosphere overnight at 50° C. The mixture was then filtered and concentrated to afford 3-amino-4-fluoro-N-methylbenzenesulfonamide (1.25 g, 89%) as an off-white solid. $^1$H NMR (400 MHz, DMSO-d$_6$) δ 7.26 (q, J=4.85 Hz, 1H), 7.13-7.22 (m, 2H), 6.90 (ddd, J=2.38, 4.27, 8.41 Hz, 1H), 5.63 (s, 2H), 2.40 (d, J=5.02 Hz, 3H); MS (m/z) 205.1 (M+H$^+$)

Preparation 6

3-amino-4-chloro-N-methylbenzenesulfonamide

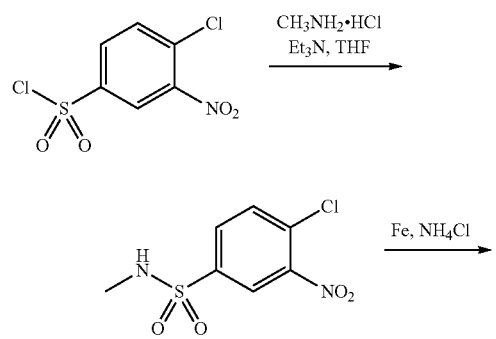

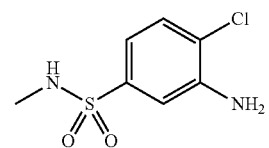

Step 1.
4-chloro-N-methyl-3-nitrobenzenesulfonamide

A solution of 4-chloro-3-nitrobenzenesulfonyl chloride (10 g, 39.1 mmol) in THF (100 mL) was cooled to −40° C. before being treated with a solution of methylamine hydrochloride (2.64 g, 39.1 mmol) in 10 ml of water followed by TEA (5.44 mL, 39.1 mmol). The reaction mixture was stirred and allowed to warm to room temperature over 1 hour before being partitioned between 350 mL EtOAc and 30 mL brine. The organic layer was washed twice with brine, dried over MgSO$_4$ and subjected to flash chromatography (330 g silica gel, 0-40% EtOAc/hexane) to afford 4-chloro-N-methyl-3-nitrobenzenesulfonamide (6.38 g, 65%) as a light yellow solid. MS (m/z) 251.0 (M+H$^+$).

Step 2.
3-amino-4-chloro-N-methylbenzenesulfonamide

A solution of 4-chloro-N-methyl-3-nitrobenzenesulfonamide (6.35 g, 25.3 mmol) in EtOH (150 mL) and water (50.0 mL) was treated with iron (14.15 g, 253 mmol) and NH$_4$Cl (13.55 g, 253 mmol) and heated at 90° C. for 4 hours before being cooled and filtered through celite. The filter cake was washed with EtOAc and the combined filtrate was filtered again to remove precipitated NH$_4$Cl before being concentrated. The resulting crude material was partitioned between 350 ml EtOAc and 50 ml saturated aqueous NaHCO$_3$. The organic layer was washed with brine, dried over MgSO$_4$, concentrated and subjected to flash column chromatography (330 g silica gel, 0-15% EtOAc/DCM) to afford 3-amino-4-chloro-N-methylbenzenesulfonamide (5.60 g, 100%) as a light yellow crystalline solid. $^1$H NMR (400 MHz, MeOD) δ ppm 7.39 (d, J=8.28 Hz, 1 H), 7.27 (d, J=2.26 Hz, 1 H), 7.03 (dd, J=8.28, 2.26 Hz, 1 H), 2.54 (s, 3 H). MS 221.0 (M+H$^+$).

Preparation 7

3-amino-N-methyl-4-[methyl(2,2,2-trifluoroethyl)amino]benzenesulfonamide

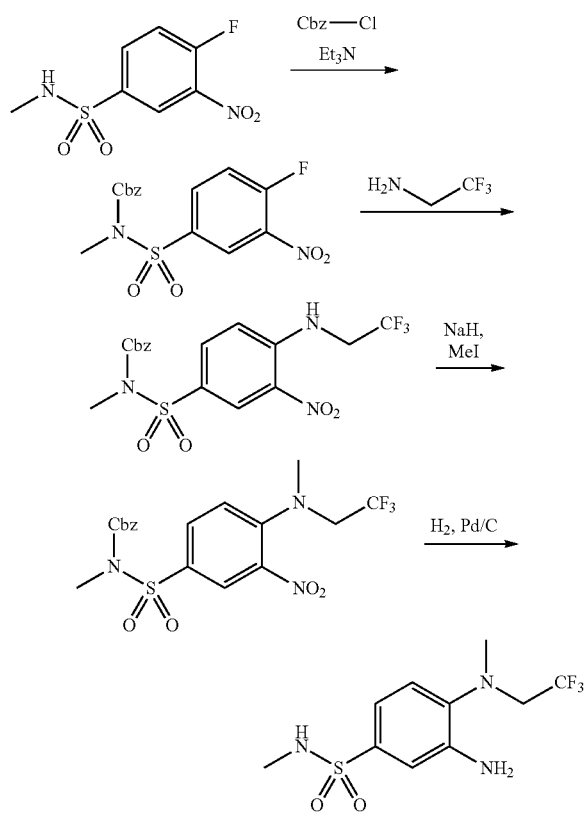

Step 1. phenylmethyl[(4-fluoro-3-nitrophenyl)sulfonyl]methylcarbamate

A solution of 4-fluoro-N-methyl-3-nitrobenzenesulfonamide (2 g, 8.54 mmol) in THF (20 mL) was treated with triethylamine (2.380 mL, 17.08 mmol) followed by dropwise addition of benzyl chloroformate (3.75 mL, 11.10 mmol). The mixture was stirred at 25° C. for 5 hours before being concentrated. The residue was treated with water and extracted with $CH_2Cl_2$. The organic extracts were washed (brine), dried (sodium sulfate), concentrated, and subjected to flash chromatography (25-50% EtOAc-hexanes) to give a yellow solid, which was suspended in EtOAc-hexanes, collected by filtration, and washed with hexanes to give phenylmethyl[(4-fluoro-3-nitrophenyl)sulfonyl]methylcarbamate (1 g, 32%) as a white solid. MS (m/z) 391.0 (M+Na$^+$).

Step 2. phenylmethyl methyl({3-nitro-4-[(2,2,2-trifluoroethyl)amino]phenyl}sulfonyl)carbamate A solution of phenylmethyl[(4-fluoro-3-nitrophenyl)sulfonyl]methylcarbamate (1 g, 2.71 mmol) in THF (10 mL) at 25° C. was treated with 2,2,2-trifluoroethylamine (0.592 g, 5.97 mmol) and stirred for 20 hours before being concentrated to give a yellow oil, which was dissolved in EtOAc/hexanes. A yellow precipitate formed, which was collected by filtration and washed with hexanes to give phenylmethyl methyl({3-nitro-4-[(2,2,2-trifluoroethyl)amino]phenyl}sulfonyl)carbamate (1.07 g, 88%) as a yellow solid. MS (m/z) 448.1 (M+H$^+$).

Step 3. phenylmethyl methyl({4-[methyl(2,2,2-trifluoroethyl)amino]-3-nitrophenyl}sulfonyl)carbamate A solution of phenylmethyl methyl({3-nitro-4-[(2,2,2-trifluoroethyl)amino]phenyl}sulfonyl)carbamate (1 g, 2.24 mmol) in DMF (1 mL) at 25° C. was treated with sodium hydride (0.179 g, 4.47 mmol) and stirred for 2 minutes before being treated with iodomethane (0.42 mL, 6.71 mmol). After 1 hour, the mixture was diluted with water and extracted with EtOAc. The organic extract was washed (brine), dried (sodium sulfate), concentrated, and subjected to flash chromatography (10-35% EtOAc-hexanes) to give phenylmethyl methyl({4-[methyl(2,2,2-trifluoroethyl)amino]-3-nitrophenyl}sulfonyl) carbamate (539 mg, 52%) as a yellow oil. MS (m/z) 462.1 (M+H$^+$).

Step 4. 3-amino-N-methyl-4-[methyl(2,2,2-trifluoroethyl)amino]benzenesulfonamide A solution of phenylmethyl methyl({4-[methyl(2,2,2-trifluoroethyl)amino]-3-nitrophenyl}sulfonyl)carbamate (539 mg, 1.17 mmol) in MeOH (10 mL) at 25° C. was treated with 10% palladium on carbon (124 mg, 0.117 mmol) and stirred under an atmosphere of hydrogen (balloon) overnight before being filtered through celite. The filtrate was again filtered through a 0.45 micron syringe filter and concentrated to give 3-amino-N-methyl-4-[methyl(2,2,2-trifluoroethyl)amino]benzenesulfonamide (320 mg, 92%) as a brown oil. $^1$H NMR (400 MHz, DMSO-d$_6$) δ ppm 7.14-7.20 (m, 2 H), 7.12 (d, J=2.26 Hz, 1 H), 6.95 (dd, J=8.28, 2.26 Hz, 1 H), 5.23 (s, 2 H), 3.82 (q, J=9.87 Hz, 2 H), 2.83 (s, 3 H), 2.39 (d, J=5.02 Hz, 3 H). MS (m/z) 298.0 (M+H$^+$).

Preparation 8

5-amino-2-fluoro-N-methylbenzenesulfonamide

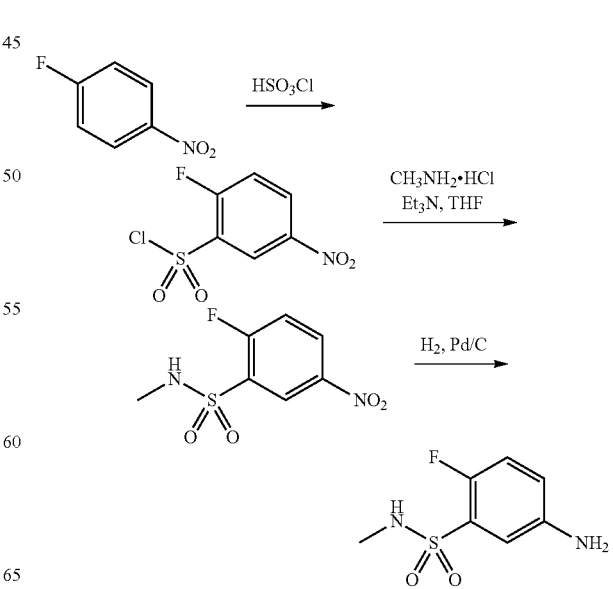

Step 1. 2-fluoro-5-nitrobenzenesulfonyl chloride

A mixture of 1-fluoro-4-nitrobenzene (3.0 g, 21.3 mmol) in chlorosulfonic acid (5.5 mL, 84 mmol) was stirred at 90-100° C. for 8 hours before being cooled to room temperature and slowly poured into ice water and extracted with EtOAc. The organic extract was washed with saturated aq. $NaHCO_3$ and water, dried (sodium sulfate), and concentrated to give 2-fluoro-5-nitrobenzenesulfonyl chloride (3.2 g, 63%) as a colorless oil, which was used directly in the next step.

Step 2. 2-fluoro-N-methyl-5-nitrobenzenesulfonamide

A solution of 2-fluoro-5-nitrobenzenesulfonyl chloride (3.2 g, 12.6 mmol) in THF (30 mL) at −45° C. was treated with methylamine hydrochloride (1.0 g, 15.1 mmol) and triethylamine (2.1 mL, 15.1 mmol) and stirred for 30 minutes. The mixture was then treated with 6M aqueous HCl to adjust the pH to 3 and warmed to room temperature before being diluted with water and extracted with EtOAc. The organic extract was dried (sodium sulfate), concentrated, and subjected to flash chromatography (5-20% EtOAc-petroleum ether) to give 2-fluoro-N-methyl-5-nitrobenzenesulfonamide as a yellow solid (3.0 g, 93%). MS (m/z) 235.1 ($M+H^+$).

Step 3. 5-amino-2-fluoro-N-methylbenzenesulfonamide

A solution of 2-fluoro-N-methyl-5-nitrobenzenesulfonamide (3.0 g, 12.8 mmol) in
MeOH (40 mL) was treated with 10% palladium on carbon (300 mg, 0.28 mmol) and stirred under hydrogen (40 psi) for 8 hours before being filtered through celite and concentrated to give 5-amino-2-fluoro-N-methylbenzenesulfonamide (2.5 g, 96%) as an off-white solid. $^1$H NMR (400 MHz, DMSO-$d_6$) δ ppm 7.40-7.49 (m, 1 H), 7.01-7.09 (m, 1 H), 6.94 (dd, J=5.95, 2.87 Hz, 1 H), 6.71-6.77 (m, 1 H), 5.49 (br. s., 2 H), 2.45 (d, J=4.85 Hz, 3 H). MS (m/z) 205.1 ($M+H^+$).

The following anilines were prepared from the indicated nitrobenzenes using procedures analogous to those described in Preparation 8:

| Aniline Product | Nitrobenzene in Step 1 | MS (m/z) | $^1$H NMR |
| --- | --- | --- | --- |
| 3-amino-N-methyl-4-[(trifluoromethyl)oxy]benzenesulfonamide | 1-nitro-2-[(trifluoromethyl)oxy]benzene | 271.0 ($M + H^+$) | $^1$H NMR (400 MHz, DMSO-$d_6$) δ ppm 7.39 (q, J = 4.77 Hz, 1 H), 7.31 (dd, J = 8.53, 1.51 Hz, 1 H), 7.24 (d, J = 2.26 Hz, 1 H), 6.92 (dd, J = 8.41, 2.38 Hz, 1 H), 5.92 (s, 2 H), 2.43 (d, J = 4.77 Hz, 3 H) |
| 5-amino-2-fluoro-N-methyl-4-(methyloxy)benzenesulfonamide | 4-fluoro-2-(methyloxy)-1-nitrobenzene | 235.1 ($M + H^+$) | $^1$H NMR (400 MHz, DMSO-$d_6$) δ ppm 7.31 (br. s., 1 H), 6.96 (d, J = 7.28 Hz, 1 H), 6.90 (d, J = 11.91 Hz, 1 H), 4.97 (s, 2 H), 3.82 (s, 3 H), 2.40 (d, J = 3.75 Hz, 3 H) |

Preparation 9

5-amino-4-(dimethylamino)-2-fluoro-N-methylbenzenesulfonamide

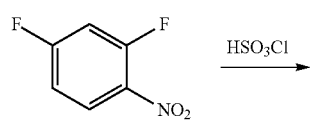

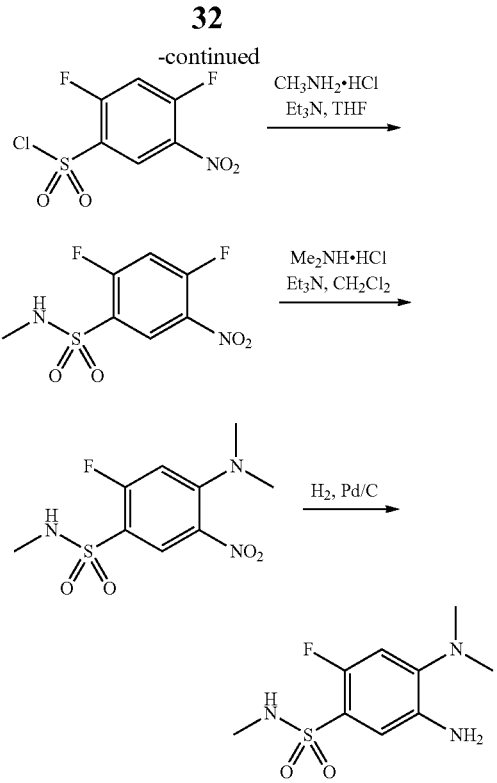

Step 1. 2,4-difluoro-5-nitrobenzenesulfonyl chloride

A mixture of 2,4-difluoro-1-nitrobenzene (20 g, 126 mmol) in chlorosulfonic acid (44 g, 378 mmol) was stirred at 100° C. for 48 hours before being poured into ice-water and extracted with EtOAc. The organic extract was dried ($Na_2SO_4$) and concentrated, and the residue was triturated with 10% EtOAc-petroleum ether to give 2,4-difluoro-5-nitrobenzenesulfonyl chloride as a brown oil (21 g, 81%) which was used directly in the next step.

Step 2. 2,4-difluoro-N-methyl-5-nitrobenzenesulfonamide

A solution of 2,4-difluoro-5-nitrobenzenesulfonyl chloride (21 g, 81 mmol) in THF (400 mL) at −60° C. was treated with methylamine hydrochloride (6.6 g, 97 mmol) and then treated dropwise with triethylamine (22.6 mL, 162 mmol). After stirring for 6 hours at −60 to −40° C. the mixture was adjusted to pH 3 with the addition of 15% aqueous HCl, diluted with water, and extracted with EtOAc. The organic extracts were dried ($Na_2SO_4$), concentrated, and subjected to flash chromatography (17% EtOAc-petroleum ether) to give 2,4-difluoro- N-methyl-5-nitrobenzenesulfonamide (8 g, 38%) as a brown solid. $^1$H NMR (400 MHz, CDCl$_3$) δ ppm 8.66-8.74 (m, 1 H), 7.20-7.25 (m, 1 H), 4.81-4.91 (m, 1 H), 2.78-2.81 (m, 3 H).

Step 3. 4-(dimethylamino)-2-fluoro-N-methyl-5-nitrobenzenesulfonamide

A solution of 2,4-difluoro-N-methyl-5-nitrobenzene-sulfonamide (8.0 g, 31.6 mmol) in CH$_2$Cl$_2$ (200 mL) at −20° C. was treated with dimethylamine hydrochloride (2.56 g, 31.6 mmol). The resulting mixture was treated dropwise with triethylamine and stirred for 1 hour before being treated with 15% aqueous HCl to adjust the pH to 3, diluted with water, and extracted with EtOAc. The organic extract was dried (sodium sulfate), concentrated, and subjected to flash chromatography (20-50% EtOAc-petroleum ether) to give 4-(dimethylamino)-2-fluoro-N-methyl-5-nitrobenzene-sulfonamide (4.0 g, 46%) as a yellow solid. MS (m/z) 278.1 (M+H$^+$).

Step 4. 5-amino-4-(dimethylamino)-2-fluoro-N-methylbenzenesulfonamide

A solution of 4-(dimethylamino)-2-fluoro-N-methyl-5-nitrobenzenesulfonamide (4.0 g, 14.3 mmol) in MeOH (100 mL) was treated with 10% Pd/C (400 mg) and stirred under H$_2$ (50 psi) for 16 hours before being filtered, concentrated, and subjected to flash chromatography (33-50% EtOAc-petroleum ether) to give 5-amino-4-(d imethylamino)-2-fluoro-N-methylbenzenesulfonamide as a white solid (2.5 g, 71%). $^1$H NMR (400 MHz, CDCl$_3$) δ ppm 7.13 (d, J=7.28 Hz, 1 H), 6.75 (d, J=11.69 Hz, 1 H), 4.58 (q, J=4.85 Hz, 1 H), 3.87 (br. s., 2 H), 2.66 (d, J=5.51 Hz, 3 H). MS (m/z) 248.1 (M+H$^+$).

Preparation 10

5-amino-2-fluoro-N-methyl-4-[(2,2,2-trifluoroethyl)oxy]benzenesulfonamide

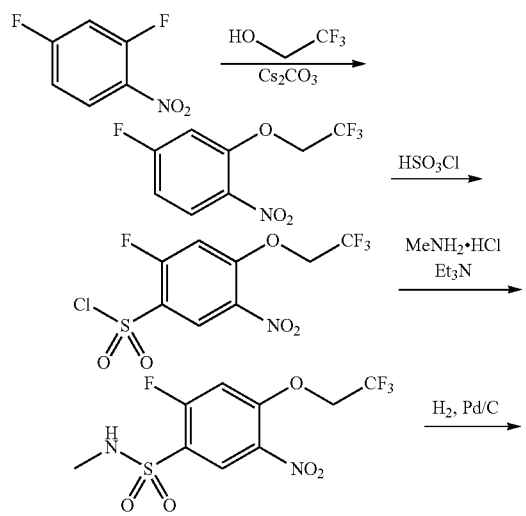

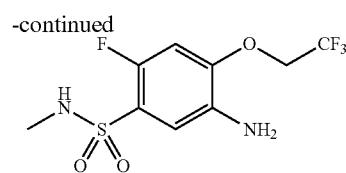

Step 1. 4-fluoro-1-nitro-2-[(2,2,2-trifluoroethyl)oxy]benzene

A mixture of 2,4-difluoro-1-nitrobenzene (10 g, 62.9 mmol) and 2,2,2-trifluoroethanol (6.29 g, 62.9 mmol) in THF (100 mL) at 25° C. was treated with Cs$_2$CO$_3$ (20.5 g, 62.9 mmol) and stirred for 8 hours before being diluted with the addition of water and extracted with EtOAc. The organic extract was dried (Na$_2$SO$_4$), concentrated, and subjected to flash chromatography (3% EtOAc-petroleum ether) to give 4-fluoro-1-nitro-2-[(2,2,2-trifluoroethyl)oxy]benzene (10 g, 67%) as a yellow solid. MS (m/z) 240.0 (M+H$_+$).

Step 2. 2-fluoro-5-nitro-4-[(2,2,2-trifluoroethyl)oxy]benzenesulfonyl chloride A mixture of 4-fluoro-1-nitro-2-[(2,2,2-trifluoroethyl)oxy]benzene (10 g, 41.8 mmol) in chlorosulfonic acid (82 mL, 125.5 mmol) was stirred at 50° C. for 8 hours before being poured into ice and extracted with EtOAc. The organic extracts were dried (Na$_2$SO$_4$) and concentrated to give 2-fluoro-5-nitro-4-[(2,2,2-trifluoroethyl)oxy]benzenesulfonyl chloride (15 g, crude) as a brown oil, which was used directly in the next step.

Step 3. 2-fluoro-N-methyl-5-nitro-4-[(2,2,2-trifluoroethyl)oxy]benzenesulfonamide A mixture of 2-fluoro-5-nitro-4-[(2,2,2-trifluoroethyl)oxy]benzenesulfonyl chloride (15 g, crude) in THF (150 mL) at −45° C. was treated with methylamine hydrochloride (5.96 g, 89 mmol) and then treated dropwise with triethylamine (12.4 mL, 89 mmol). After stirring for 1 hour at −45° C., the mixture was adjusted to pH 3 by the addition of aqueous 3M HCl, warmed to room temperature, diluted with water, and extracted with EtOAc. The organic extract was dried (Na$_2$SO$_4$), concentrated, and subjected to flash chromatography (9-17% EtOAc-petroleum ether) to give 2-fluoro-N-methyl-5-nitro-4-[(2,2,2-trifluoroethyl)oxy]benzenesulfonamide (10 g, 72% for two steps) as a yellow solid. MS (m/z) 333.0 (M+H$^+$).

Step 4. 5-amino-2-fluoro-N-methyl-4-[(2,2,2-trifluoroethyl)oxy]benzenesulfonamide A mixture of 2-fluoro-N-methyl-5-nitro-4-[(2,2,2-trifluoroethyl)oxy]benzene-sulfonamide (10 g, 30.1 mmol) in MeOH (150 mL) was treated with 10% Pd/C (1 g) and stirred under H$_2$ (45 psi) at 45° C. for 10 hours before being filtered. The filtrate was concentrated to give 5-amino-2-fluoro-N-methyl-4-[(2,2,2-trifluoroethyl)oxy]benzene-sulfonamide (8 g, 88%) as a white solid. $^1$H NMR (400 MHz, DMSO-d$_6$) δ ppm 7.40 (q, J=5.07 Hz, 1 H), 7.10 (d, J=11.69 Hz, 1 H), 7.05 (d, J=7.28 Hz, 1 H), 5.04 (s, 2 H), 4.83 (q, J=8.82 Hz, 2 H), 2.42 (d, J=4.41 Hz, 3 H). MS (m/z) 303.0 (M+H$^+$).

Preparation 11

3-amino-N-methyl-4-(methylsulfonyl)benzenesulfonamide

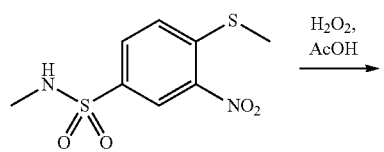

Step 1. N-methyl-4-(methylsulfonyl)-3-nitrobenzenesulfonamide

A mixture of N-methyl-4-(methylthio)-3-nitrobenzenesulfonamide (1.0 g, 3.81 mmol) in AcOH (15 mL) was treated dropwise with 30% aqueous $H_2O_2$ (5 mL, 44 mmol) and stirred at 117° C. for 2 hours before being cooled to room temperature and diluted with water (100 mL). The precipitate that formed was collected by filtration and dried to give N-methyl-4-(methylsulfonyl)-3-nitrobenzenesulfonamide (1.5 g, crude) as a yellow solid, which was used directly in the next step.

Step 2. 3-amino-N-methyl-4-(methylsulfonyl)benzenesulfonamide

A solution of N-methyl-4-(methylsulfonyl)-3-nitrobenzenesulfonamide (1.5 g, crude) in EtOH (20 mL) and saturated aqueous $NH_4Cl$ (20 mL) was treated with Zn dust (3.3. g, 51 mmol) and stirred at 50° C. overnight before being filtered (EtOAc wash). The filtrate was diluted with water and extracted with EtOAc. The organic extract was washed with water and brine, dried ($MgSO_4$), concentrated, and subjected to flash chromatography (33% EtOAc-petroleum ether) to give 3-amino-N-methyl-4-(methylsulfonyl)benzenesulfonamide (950 mg, 94% 2 steps) as a yellow solid. $^1$H NMR (400 MHz, DMSO-$d_6$) δ ppm 7.73 (d, J=8.28 Hz, 1 H), 7.58 (q, J=4.94 Hz, 1 H), 7.34 (d, J=1.76 Hz, 1 H), 7.01 (dd, J=8.53, 1.76 Hz, 1 H), 6.48 (s, 2 H), 3.18 (s, 3 H), 2.47 (d, J=5.02 Hz, 3 H). MS (m/z) 265.0 (M+H$^+$).

Preparation 12

4,5-dichloro-6,7-bis(methyloxy)quinazoline

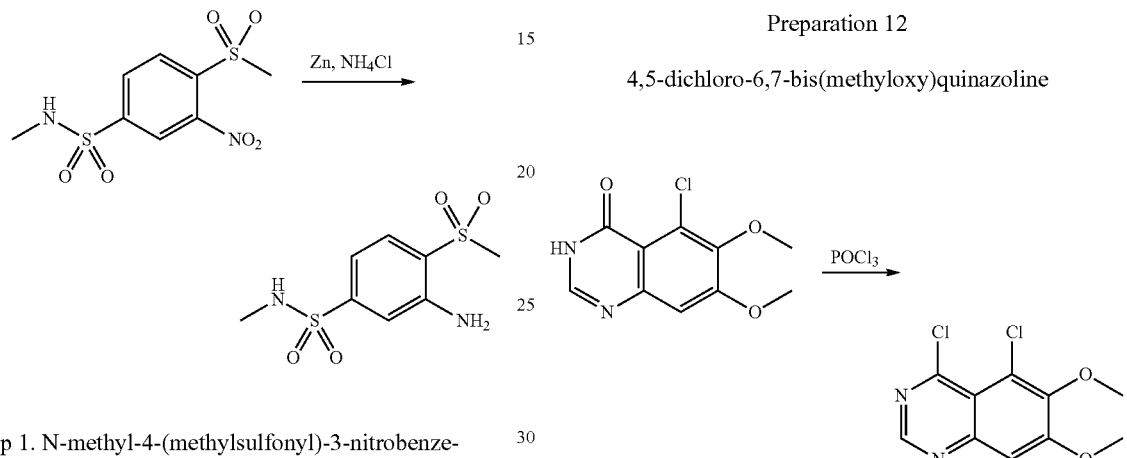

A mixture of 5-chloro-6,7-bis(methyloxy)-4(1H)-quinazolinone (100 mg, 0.42 mmol, prepared according to *J. Med. Chem.* (1999) 42 3860) in $POCl_3$ (2 mL) was heated at 80-90° C. for 8 hours before being concentrated. The residue was treated with saturated aqueous $NaHCO_3$ and extracted with EtOAc. The organic extract was dried ($Na_2SO_4$) and concentrated to give 4,5-dichloro-6,7-bis(methyloxy)quinazoline (70 mg, 65%) as a yellow solid. $^1$H NMR (400 MHz, DMSO-$d_6$) δ ppm 8.94 (s, 1 H), 7.56 (s, 1 H), 4.05 (s, 3 H), 3.87 (s, 3 H). MS (m/z) 258.9 (M+H$^+$).

The following 4-chloroquinazolines were prepared from the indicated commercially available or known quinazolinones using procedures analogous to those described in Preparation 12:

| Quinazoline Product | Quinazolinone SM | MS (m/z) | $^1$H NMR |
|---|---|---|---|
| 4-chloro-6,7-bis{[2-(methyloxy)ethyl]oxy}quinazoline | 6,7-bis{[2-(methyloxy)ethyl]oxy}-4(1H)-quinazolinone | 313.0 (M + H$^+$) | $^1$H NMR (400 MHz, DMSO-$d_6$) δ ppm 8.88 (s, 1 H), 7.50 (s, 1 H), 7.46 (s, 1 H), 4.32-4.42 (m, 4 H), 3.75-3.81 (m, 4 H), 3.37 (s, 3 H), 3.36 (s, 3 H) |
| 4-chloro-6-iodo-7-(methyloxy)quinazoline | 6-iodo-7-(methyloxy)-4(1H)-quinazolinone (prepared as in U.S. Pat. No. 6,225,318 B1 (2001)) | 320.7 (M + H$^+$) | $^1$H NMR (400 MHz, DMSO-$d_6$) δ ppm 9.03 (s, 1 H), 8.67 (s, 1 H), 7.48 (s, 1 H), 4.08 (s, 3 H) |

Preparation 13

4-chloro-6-(ethyloxy)-7-(methyloxy)quinazoline

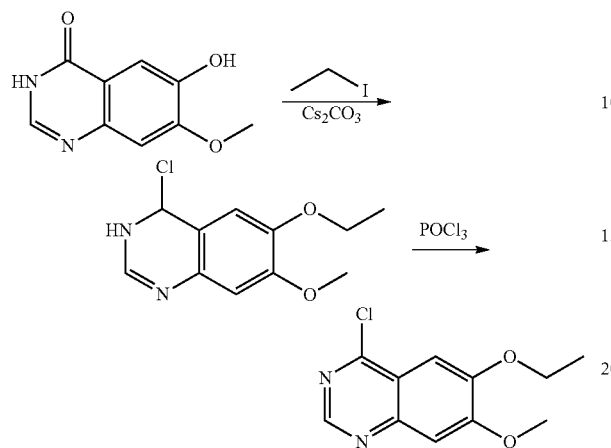

Step 1. 6-(ethyloxy)-7-(methyloxy)-4(1H)-quinazolinone

A mixture of 6-hydroxy-7-(methyloxy)-4(1H)-quinazolinone (1 g, 5.2 mmol) in water (12 mL), MeCN (6 mL), and MeOH (1 mL) at 25° C. was treated with Cs$_2$CO$_3$ (1.7 g, 5.2 mmol). After the mixture was stirred for 30 minutes, iodoethane (0.42 mL, 5.2 mmol) was added and the mixture was stirred at 60° C. for 40 hours before being cooled to room temperature. The solid was collected by filtration and washed with MeOH to give 6-(ethyloxy)-7-(methyloxy)-4(1H)-quinazolinone (560 mg, 49%). MS (m/z) 221.1 (M+H$^+$).

Step 2. 4-chloro-6-(ethyloxy)-7-(methyloxy)quinazoline

A mixture of 6-(ethyloxy)-7-(methyloxy)-4(1H)-quinazolinone (560 mg, 2.54 mmol) in POCl$_3$ (5 mL, 53.6 mmol) was treated with 1 drop of DMF and heated at 100° C. for 2 hours before being concentrated. The residue was treated with saturated aqueous NaHCO$_3$ and extracted with CH$_2$Cl$_2$. The organic extracts were dried (sodium sulfate) and concentrated to give 4-chloro-6-(ethyloxy)-7-(methyloxy)quinazoline (416 mg, 1.74 mmol, 69%) as an off-white solid. $^1$H NMR (400 MHz, DMSO-d$_6$) δ ppm 8.88 (s, 1 H), 7.46 (s, 1 H), 7.39 (s, 1 H), 4.26 (q, J=6.94 Hz, 2 H), 4.02 (s, 3 H), 1.44 (t, J=7.03 Hz, 3 H). MS (m/z) 239.0 (M+H$^+$).

The following quinazolines were prepared using procedures analogous to those described in Preparation 13 by substituting the indicated alkyl halide in the place iodoethane in Step 1:

Preparation 14

4-chloro-5-(ethyloxy)-7-(methyloxy)quinazoline

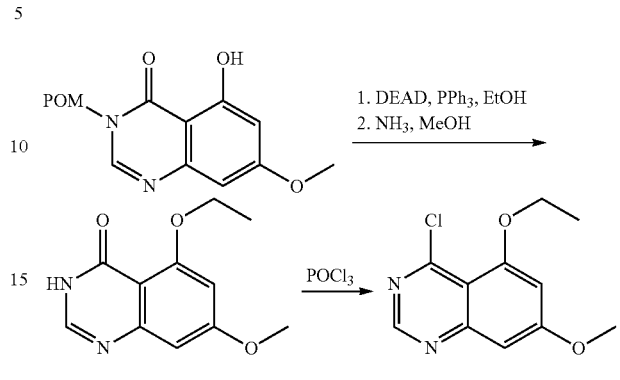

Step 1. 5-(ethyloxy)-7-(methyloxy)-4(1H)-quinazolinone

A mixture of [5-hydroxy-7-(methyloxy)-4-oxo-3(4H)-quinazolinyl]methyl 2,2-dimethylpropanoate (1 g, 3.26 mmol, prepared according to J. Med. Chem. (2006) 49 6465), triphenylphosphine (1.370 g, 5.22 mmol), and ethanol (0.210 mL, 3.59 mmol) in DCM (10 mL) at 0° C. was treated dropwise over 2 minutes with a 40% solution of DEAD in toluene (2.379 mL, 5.22 mmol). After addition, the mixture was warmed to room temperature and stirred for 3 hours before being concentrated. The residue was dissolved in 7 M ammonia in methanol (10 mL, 70.0 mmol) and the mixture was stirred for 3 days. The solid was collected by filtration and washed with MeOH and CH$_2$Cl$_2$ to give 5-(ethyloxy)-7-(methyloxy)-4(1H)-quinazolinone (286 mg, 40%) as a white solid. MS (m/z) 221.1 (M+H$^+$).

Step 2. 4-chloro-5-(ethyloxy)-7-(methyloxy)quinazoline

A mixture of 5-(ethyloxy)-7-(methyloxy)-4(1H)-quinazolinone (285 mg, 1.29 mmol) in POCl$_3$ (10 mL, 107 mmol) was treated with 1 drop of DMF and stirred at 100° C. for 1 hour before being concentrated. The residue was treated with saturated aqueous NaHCO$_3$ and extracted with CH$_2$Cl$_2$. The organic extracts were dried (sodium sulfate), concentrated, and subjected to flash chromatography (1-3% MeOH—CH$_2$Cl$_2$) to give 4-chloro-5-(ethyloxy)-7-(methyloxy)quinazoline (260 mg, 84%) as a white solid. $^1$H NMR (400 MHz, DMSO-d$_6$) δ ppm 8.84 (s, 1 H), 7.03 (d, J=2.51 Hz, 1 H), 6.84 (d, J=2.26 Hz, 1 H), 4.22 (q, J=6.86 Hz, 2 H), 3.96 (s, 3 H), 1.47 (t, J=6.90 Hz, 3 H). MS (m/z) 239.0 (M+H$^+$).

The following quinazolines were prepared using procedures analogous to those described in Preparation 14 by substituting the indicated alcohol in the place of ethanol in Step 1:

| Quinazoline Product | Alkyl Halide in Step 1 | MS (m/z) | $^1$H NMR |
|---|---|---|---|
| 4-chloro-6-[(1-methylethyl)oxy]-7-(methyloxy)quinazoline | 2-bromopropane | 253.0 (M + H$^+$) | $^1$H NMR (400 MHz, DMSO-d$_6$) δ ppm 8.88 (s, 1 H), 7.46 (s, 1 H), 7.41 (s, 1 H), 4.86-4.97 (m, 1 H), 4.01 (s, 3 H), 1.38 (d, J = 6.02 Hz, 6 H) |

| Quinazoline Product | Alcohol in Step 1 | MS (m/z) | $^1$H NMR |
|---|---|---|---|
| 4-chloro-5-[(1-methylethyl)oxy]-7-(methyloxy)quinazoline | 2-propanol | 253.0 (M + H$^+$) | $^1$H NMR (400 MHz, DMSO-d$_6$) δ ppm 8.82 (s, 1 H), 7.02 (d, J = 2.26 Hz, 1 H), 6.88 (d, J = 2.26 Hz, 1 H), 4.85-4.96 (m, 1 H), 3.96 (s, 3 H), 1.40 (d, J = 6.02 Hz, 6 H) |
| 4-chloro-7-(methyloxy)-5-(tetrahydro-2H-pyran-4-yloxy)quinazoline | tetrahydro-2H-pyran-4-ol | 295.0 (M + H$^+$) | $^1$H NMR (400 MHz, DMSO-d$_6$) δ ppm 8.69 (br. s., 1 H), 6.78 (s, 2 H), 4.81-4.91 (m, 1 H), 3.86-3.93 (m, 5 H), 3.49-3.56 (m, 2 H), 1.89-2.01 (m, 2 H), 1.68 (m, J = 13.49, 6.93, 6.93, 3.51 Hz, 2 H) |
| 4-chloro-7-(methyloxy)-5-{[2-(methyloxy)ethyl]oxy}quinazoline | 2-(methyloxy)ethanol | 269.0 (M + H$^+$) | $^1$H NMR (400 MHz, DMSO-d$_6$) δ ppm 8.84 (s, 1 H), 7.04 (d, J = 2.26 Hz, 1 H), 6.88 (d, J = 2.26 Hz, 1 H), 4.26-4.33 (m, 2 H), 3.96 (s, 3 H), 3.77-3.83 (m, 2 H), 3.36 (s, 3 H) |

Preparation 15

4-chloro-5,6,7-tris(methyloxy)quinazoline

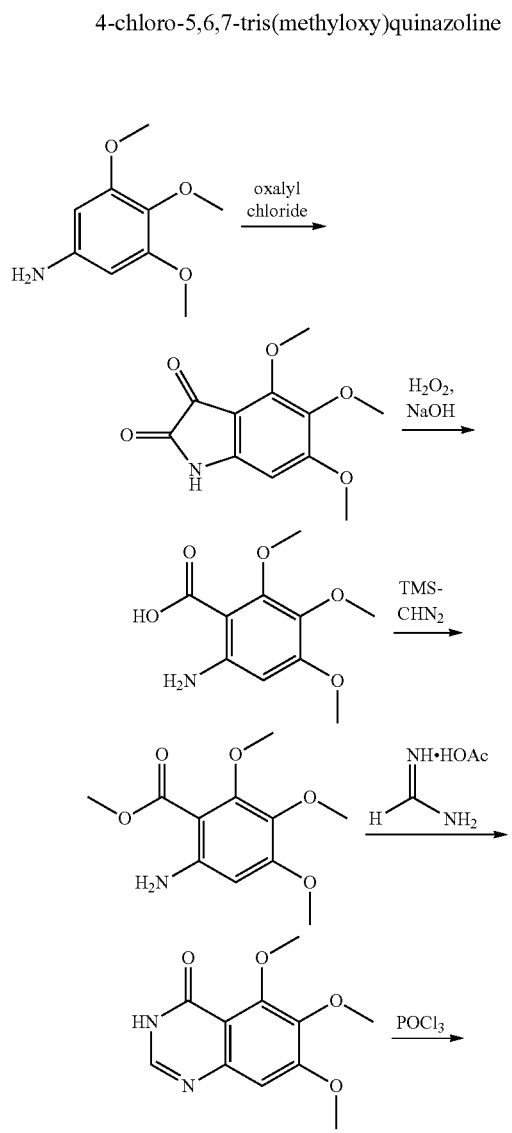

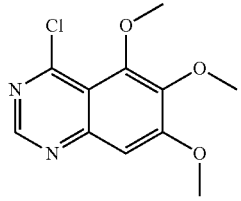

Step 1. 4,5,6-tris(methyloxy)-1H-indole-2,3-dione

A solution of 3,4,5-trimethoxyaniline (10 g, 54.6 mmol) in Et$_2$O (100 mL) was treated with a solution of 2M HCl in Et$_2$O (40.9 mL, 82 mmol) and the resulting light gray solid was collected and washed with ether to give the HCl salt of the aniline (11.5 g), which was treated with oxalyl chloride (16.72 mL, 191 mmol) and the mixture was heated at 170° C. for 1.5 hours before being cooled to room temperature and treated with MeOH. The resulting mixture was heated to boiling and filtered while hot to give a red solid, which was washed with MeOH and dried in air to give 4,5,6-tris(methyloxy)-1H-indole-2,3-dione (10.5 g, 81%) as a red-orange solid. MS (m/z) 238.0 (M+H$^+$).

Step 2. 6-amino-2,3,4-tris(methyloxy)benzoic acid

A solution of 4,5,6-tris(methyloxy)-1H-indole-2,3-dione (10 g, 42.2 mmol) in 33% aqueous NaOH (70.5 ml, 582 mmol) at 100° C. was treated with 30% aqueous hydrogen peroxide (12.9 ml, 126 mmol) dropwise over 30 min, at a rate to prevent the foaming mixture from overflowing the flask. After addition was complete, the mixture was stirred for 10 minutes before being cooled and diluted by the addition of ice. The mixture was adjusted to pH 8 by addition of concentrated HCl (70 mL) and then acidified to pH 3 with the addition of glacial acetic acid. The solid that formed was collected by filtration, washed with water, and dried under vacuum to give 6-amino-2,3,4-tris(methyloxy)benzoic acid (2.7 g, 28%) as a tan solid. MS (m/z) 228.0 (M+H$^+$).

Step 3. methyl 6-amino-2,3,4-tris(methyloxy)benzoate

A solution of 6-amino-2,3,4-tris(methyloxy)benzoic acid (2.7 g, 11.88 mmol) in THF (20 mL) and MeOH (20 mL) at 25° C. was treated with a solution of 2M TMS-diazomethane in Et$_2$O (14.85 mL, 29.7 mmol) and stirred for 10 minutes before being concentrated to give methyl 6-amino-2,3,4-tris(methyloxy)benzoate (2.87 g, 99%) as a brown solid. MS (m/z) 242.1 (M+H$^+$).

Step 4. 5,6,7-tris(methyloxy)-4(1H)-quinazolinone

A solution of methyl 6-amino-2,3,4-tris(methyloxy)benzoate (2.87 g, 11.90 mmol) and formamidine acetate (3.72 g, 35.7 mmol) in 2-methoxyethanol (25 mL) was stirred at 125° C. for 2 hrs before being concentrated. The residue was suspended in water and the solid was collected by filtration, washed with water, and dried under vacuum (45° C.) to give 5,6,7-tris(methyloxy)-4(1H)-quinazolinone (1 g, 34%) as a light brown solid. MS (m/z) 237.1 (M+H$^+$).

Step 5. 4-chloro-5,6,7-tris(methyloxy)quinazoline 5,6,7-tris(methyloxy)-4(1H)-quinazolinone (0.8 g, 3.39 mmol) was treated with POCl$_3$ (10 ml, 107 mmol) and one drop of DMF, and stirred at 100° C. for 1 hour before being concentrated. The residue was treated with saturated aqueous NaHCO$_3$ and extracted with CH$_2$Cl$_2$. The organic extracts were dried (sodium sulfate) and concentrated to give 4-chloro-5,6,7-tris(methyloxy)quinazoline (770 mg, 89%) as a tan solid. $^1$H NMR (400 MHz, DMSO-d$_6$) δ ppm 8.88 (s, 1 H), 7.37 (s, 1 H), 4.04 (s, 3 H), 3.94 (s, 3 H), 3.91 (s, 3 H). MS (m/z) 255.0 (M+H$^+$).

Preparation 16

N-methyl-3-({6-(methyloxy)-7-[(phenylmethyl)oxy]-4-quinazolinyl}amino)-4-[(2,2,2-trifluoroethyl)oxy]benzenesulfonamide

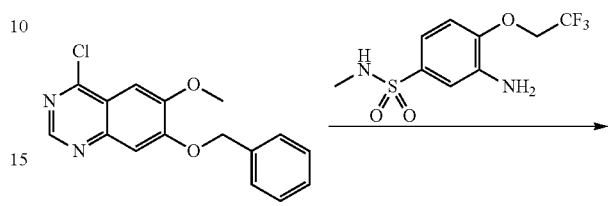

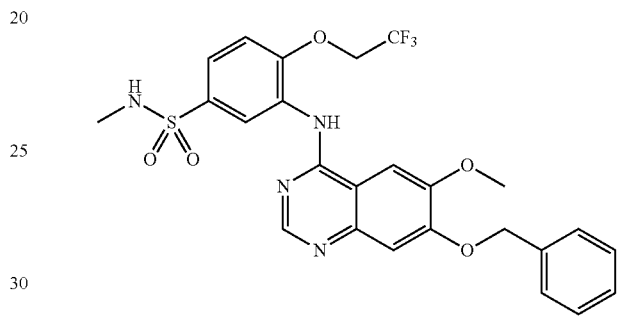

A solution of 3-amino-N-methyl-4-[(2,2,2-trifluoroethyl)oxy]benzenesulfonamide (3.0 g, 10.7 mmol) in i-PrOH (100 mL) was treated with 4-chloro-6-(methyloxy)-7-[(phenylmethyl)oxy]quinazoline (3.2 g, 10.7 mmol, prepared according to J. Med. Chem. (1999) 42 5369) and stirred at 80° C. for 2 hours before being concentrated. The residue was washed with petroleum ether and dried to give N-methyl-3-({6-(methyloxy)-7-[(phenylmethyl)oxy]-4-quinazolinyl}amino)-4-[(2,2,2-trifluoroethyl)oxy]benzenesulfonamide (4.2 g, 72%) as a brown solid. $^1$H NMR (400 MHz, DMSO-d$_6$) δ ppm 11.42 (br. s., 1 H), 8.75 (s, 1 H), 8.20 (s, 1 H), 7.80-7.84 (m, 2 H), 7.49-7.57 (m, 4 H), 7.35-7.49 (m, 4 H), 5.34 (s, 2 H), 4.91 (q, J=8.82 Hz, 2 H), 3.99 (s, 3 H), 2.45 (d, J=5.07 Hz, 3 H). MS (m/z) 549.1 (M+H$^+$).

The following compound was prepared with procedures analogous to that described in Preparation 16 using the specified quinazoline and aniline starting materials:

| Name | Structure | Quinazoline | Aniline |
|---|---|---|---|
| 4-(dimethylamino)-N-methyl-3-[(6-nitro-4-quinazolinyl)amino]benzenesulfonamide | 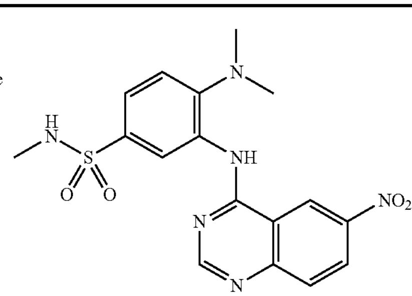 | 4-chloro-6-nitroquinazoline | 3-amino-4-(dimethylamino)-N-methylbenzenesulfonamide |

Example 1

3-{[6,7-bis(methyloxy)-4-quinazolinyl]amino}-4-(dimethylamino)-N-methylbenzenesulfonamide hydrochloride

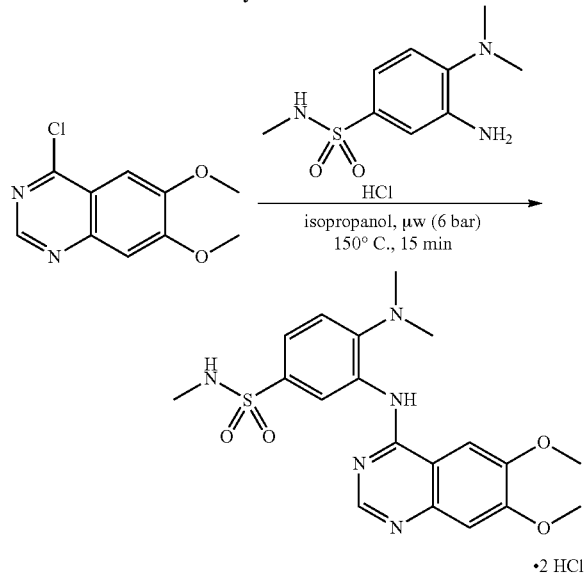

To a mixture of 3-amino-4-(dimethylamino)-N-methylbenzenesulfonamide (0.100 g, 0.434 mmol) and 4-chloro-6,7-bis(methyloxy)quinazoline (0.075 g, 0.334 mmol) in isopropanol (2 mL) was added HCl (0.334 mL, 0.334 mmol). The resulting mixture was then subjected to microwave irradiation (150° C., 6 bar) for 15 minutes. The mixture was then concentrated and purified via column chromatography (5-10% MeOH/$CH_2Cl_2$) to give an orange solid that was triturated with EtOAc and dried to afford 3-{[6,7-bis(methyloxy)-4-quinazolinyl]amino}-4-(dimethylamino)-N-methylbenzenesulfonamide (54 mg, 35% yield) as orange crystals.

The following compounds were prepared with procedures analogous to that described in Example 1 using 4-chloro-6,7-bis(methyloxy)quinazoline and the specified aniline as starting materials:

| Ex. | Name | Structure | Aniline |
|---|---|---|---|
| 2 | 3-{[6,7-bis(methyloxy)-4-quinazolinyl]amino}-N-methylbenzenesulfonamide hydrochloride | 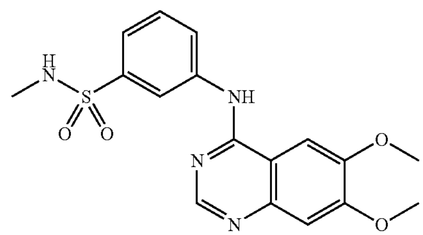 | 3-amino-N-methylbenzenesulfonamide |
| 3 | 3-{[6,7-bis(methyloxy)-4-quinazolinyl]amino}-N-methyl-4-(4-morpholinyl)benzenesulfonamide trifluoroacetate | 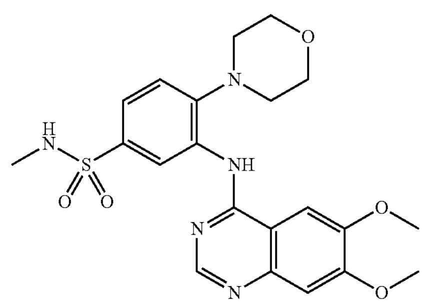 | 3-amino-N-methyl-4-(4-morpholinyl)benzenesulfonamide |
| 4 | 3-{[6,7-bis(methyloxy)-4-quinazolinyl]amino}-4-[ethyl(methyl)amino]-N-methylbenzenesulfonamide | 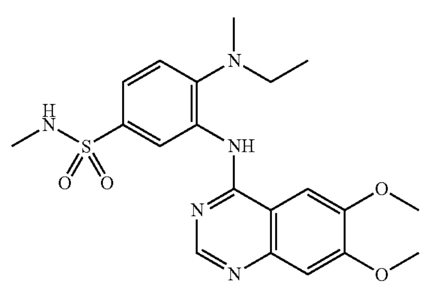 | 3-amino-4-[ethyl(methyl)amino]-N-methylbenzenesulfonamide |

-continued

| Ex. | Name | Structure | Aniline |
|---|---|---|---|
| 5 | 3-{[6,7-bis(methyloxy)-4-quinazolinyl]amino}-N-methyl-4-[(1-methylethyl)oxy]benzenesulfonamide | 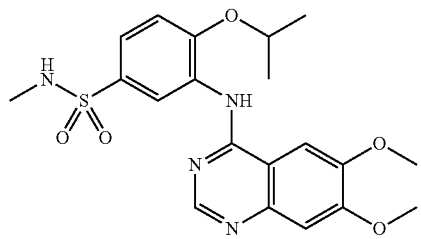 | 3-amino-N-methyl-4-[(1-methylethyl)oxy]benzenesulfonamide |
| 6 | 3-{[6,7-bis(methyloxy)-4-quinazolinyl]amino}-N-methyl-4-(methyloxy)benzenesulfonamide | 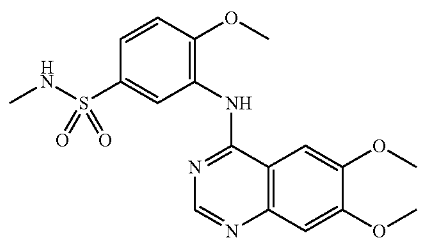 | 3-amino-N-methyl-4-(methyloxy)benzenesulfonamide |
| 7 | 3-{[6,7-bis(methyloxy)-4-quinazolinyl]amino}-N-methyl-4-(methylthio)benzenesulfonamide trifluoroacetate | 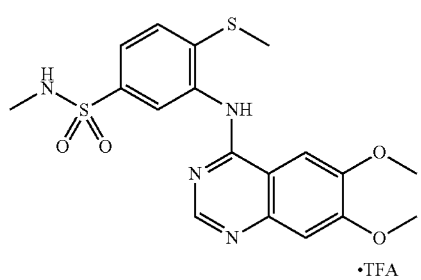 | 3-amino-N-methyl-4-(methylthio)benzenesulfonamide |

Example 8

4-(dimethylamino)-N-methyl-3-(4-quinazolinylamino)benzenesulfonamide trifluoroacetate

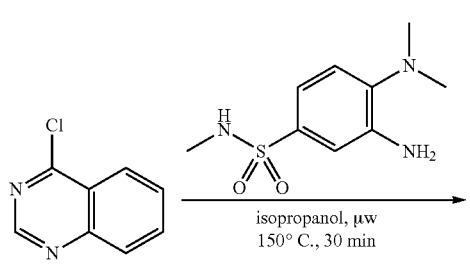

isopropanol, µw
150° C., 30 min

-continued

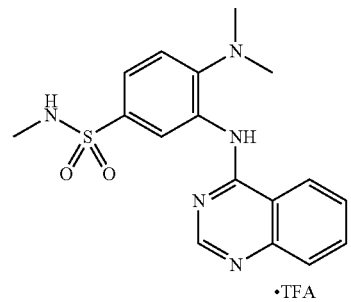

A mixture of 3-amino-4-(dimethylamino)-N-methylbenzenesulfonamide (136 mg, 0.59 mmol) and 4-chloroquinazoline (75 mg, 0.46 mmol) in i-PrOH (2 mL) was subjected to microwave irradiation (150° C., 6 bar) for 30 minutes before being filtered and subjected to reverse phase HPLC (10-50% MeCN/water/0.1% TFA; Sunfire C18 OBD 5 μM, 30×75 mm) to give an oil, which was dissolved in water and lyophilized to give 4-(dimethylamino)-N-methyl-3-(4-quinazolinylamino)benzenesulfonamide trifluoroacetate (30 mg, 13%) as an orange solid.

The following compounds were prepared with procedures analogous to that described in Example 8 using the specified quinazoline and aniline starting materials:

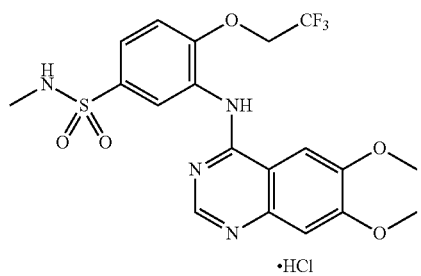

| Ex. | Name | Structure | Quinazoline | Aniline |
|---|---|---|---|---|
| 9 | 3-[(6-chloro-4-quinazolinyl)amino]-4-(dimethylamino)-N-methylbenzenesulfonamide | 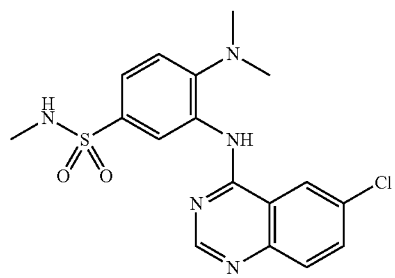 [SMILES: CNS(=O)(=O)c1ccc(N(C)C)c(Nc2ncnc3ccc(Cl)cc23)c1] | 4,6-dichloro-quinazoline | 3-amino-4-(dimethylamino)-N-methylbenzene-sulfonamide |
| 10 | 4-(dimethylamino)-N-methyl-3-{[6-(methyloxy)-4-quinazolinyl]amino}benzene sulfonamide trifluoroacetate | 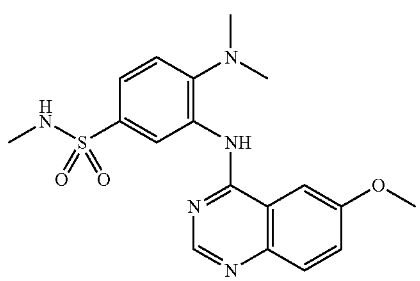 | 4-chloro-6-(methyloxy) quinazoline | 3-amino-4-(dimethylamino)-N-methylbenzene-sulfonamide |

Example 11

3-{[6,7-bis(methyloxy)-4-quinazolinyl]amino}-N-methyl-4-[(2,2,2-trifluoroethyl)oxy]benzenesulfonamide hydrochloride

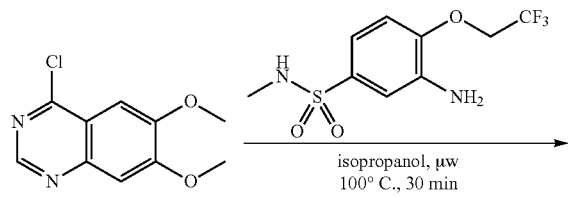

A mixture of 4-chloro-6,7-bis(methyloxy)quinazoline (100 mg, 0.445 mmol) and 3-amino-N-methyl-4-[(2,2,2-trifluoroethyl)oxy]benzenesulfonamide (139 mg, 0.490 mmol) in i-PrOH (2 mL) was subjected to microwave irradiation (100° C., 2 bar) for 30 minutes before being cooled to room temperature. The solid that formed was collected by filtration and washed with isopropanol to give 3-{[6,7-bis(methyloxy)-4-quinazolinyl]amino}-N-methyl-4-[(2,2,2-trifluoroethyl)oxy]benzenesulfonamide hydrochloride (160 mg, 70%) as a pale yellow solid.

The following compounds were prepared with procedures analogous to that described in Example 11 using the specified quinazoline and aniline starting materials:

| Ex. | Name | Structure | Quinazoline | Aniline |
|---|---|---|---|---|
| 12 | 3-[(6-chloro-4-quinazolinyl)amino]-N-methyl-4-[(2,2,2-trifluoroethyl)oxy]benzenesulfonamide | 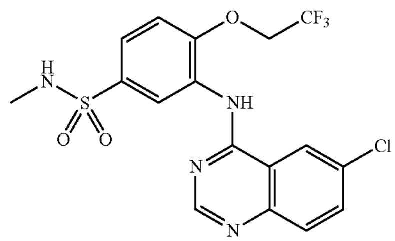 [SMILES: CNS(=O)(=O)c1ccc(OCC(F)(F)F)c(Nc2ncnc3ccc(Cl)cc23)c1] | 4,6-dichloro-quinazoline | 3-amino-N-methyl-4-[(2,2,2-trifluoroethyl)oxy]benzene-sulfonamide |
| 13 | 3-(7,8-dihydro[1,4]dioxino[2,3-g]quinazolin-4-ylamino)-4-(dimethylamino)-N-methylbenzenesulfonamide bis(trifluoroacetate) | 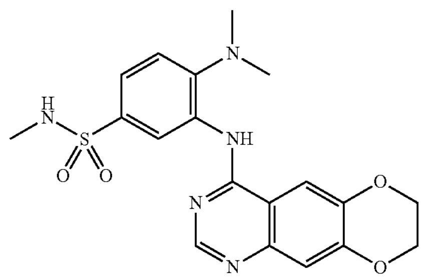 | 4-chloro-7,8-dihydro[1,4]dioxino[2,3-g]quinazoline | 3-amino-4-(dimethylamino)-N-methylbenzene sulfonamide |
| 14 | 3-{[6,7-bis(methyloxy)-4-quinazolinyl]amino}-4-(4,4-difluoro-1-piperidinyl)-N-methylbenzenesulfonamide trifluoroacetate | 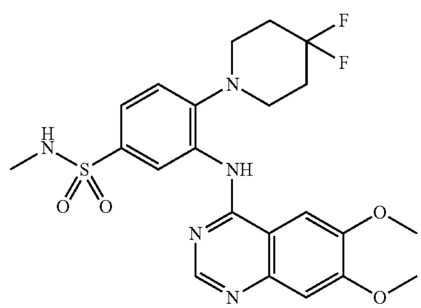 | 4-chloro-6,7-bis(methyloxy)quinazoline | 3-amino-4-(4,4-difluoro-1-piperidinyl)-N-methylbenzene sulfonamide |
| 15 | 3-[(6-chloro-4-quinazolinyl)amino]-4-(4,4-difluoro-1-piperidinyl)-N-methylbenzenesulfonamide trifluoroacetate | 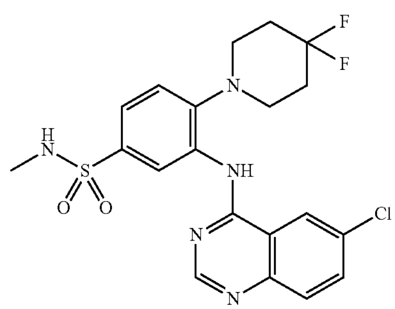 | 4,6-dichloro-quinazoline | 3-amino-4-(4,4-difluoro-1-piperidinyl)-N-methylbenzene sulfonamide |
| 16 | 3-({7-[(3-chloropropyl)oxy]-4-quinazolinyl}amino)-4-(dimethylamino)-N-methylbenzenesulfonamide | 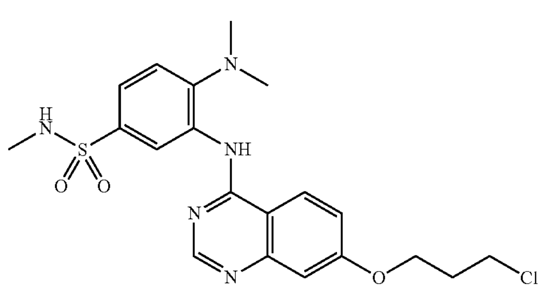 [SMILES: CNS(=O)(=O)c1ccc(N(C)C)c(Nc2ncnc3cc(OCCCCl)ccc23)c1] | 4-chloro-7-[(3-chloropropyl)oxy]quinazoline | 3-amino-4-(dimethylamino)-N-methylbenzene sulfonamide |

-continued

| Ex. | Name | Structure | Quinazoline | Aniline |
|---|---|---|---|---|
| 17 | 3-[(6,7-bis{[2-(methyloxy)ethyl]oxy}-4-quinazolinyl)amino]-4-(dimethylamino)-N-methylbenzenesulfonamide trifluoroacetate | 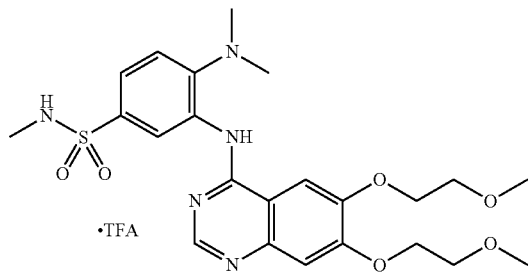 | 4-chloro-6,7-bis{[2-(methyloxy)ethyl]oxy} quinazoline | 3-amino-4-(dimethylamino)-N-methylbenzene sulfonamide |
| 18 | 3-[(6,7-bis{[2-(methyloxy)ethyl]oxy}-4-quinazolinyl)amino]-N-methyl-4-(methyloxy) benzenesulfonamide hydrochloride | 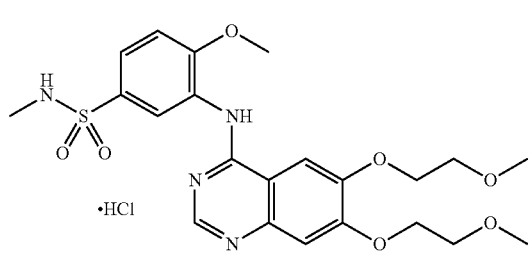 | 4-chloro-6,7-bis{[2-(methyloxy)ethyl]oxy} quinazoline | 3-amino-N-methyl-4-(methyloxy) benzene-sulfonamide |
| 19 | 3-[(6,7-bis{[2-(methyloxy)ethyl]oxy}-4-quinazolinyl)amino]-N-methyl-4-[(2,2,2-trifluoroethyl)oxy] benzenesulfonamide | 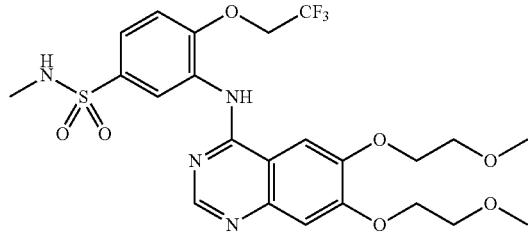 | 4-chloro-6,7-bis{[2-(methyloxy)ethyl]oxy} quinazoline | 3-amino-N-methyl-4-[(2,2,2-trifluoroethyl)oxy]benzene-sulfonamide |
| 20 | 3-[(6,7-bis{[2-(methyloxy)ethyl]oxy}-4-quinazolinyl)amino]-N-methyl-4-(methylthio) benzenesulfonamide | 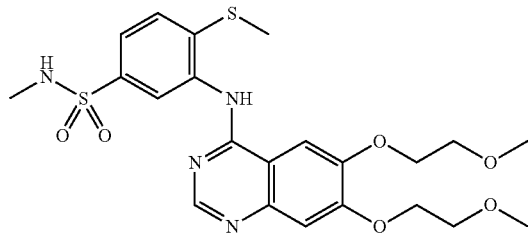 | 4-chloro-6,7-bis{[2-(methyloxy)ethyl]oxy} quinazoline | 3-amino-N-methyl-4-(methylthio) benzene-sulfonamide |
| 21 | 3-{[6,7-bis(methyloxy)-4-quinazolinyl]amino}-N-methyl-4-[(2R)-2-(trifluoromethyl)-1-pyrrolidinyl] benzenesulfonamide trifluoroacetate | 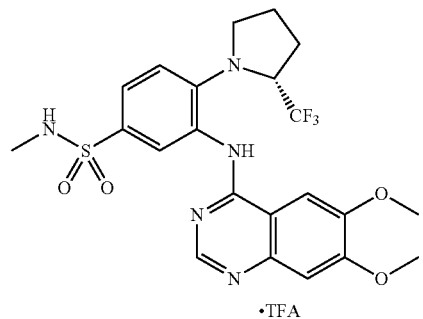 | 4-chloro-6,7-bis(methyloxy) quinazoline | 3-amino-N-methyl-4-[(2R)-2-(trifluoromethyl)-1-pyrrolidinyl] benzene-sulfonamide |

| Ex. | Name | Structure | Quinazoline | Aniline |
|---|---|---|---|---|
| 22 | 3-[(6-chloro-4-quinazolinyl)amino]-N-methyl-4-[(2R)-2-(trifluoromethyl)-1-pyrrolidinyl]benzenesulfonamide trifluoroacetate | 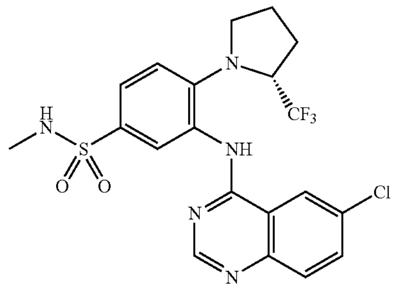 | 4,6-dichloroquinazoline | 3-amino-N-methyl-4-[(2R)-2-(trifluoromethyl)-1-pyrrolidinyl]benzenesulfonamide |
| 23 | 5-{[6,7-bis(methyloxy)-4-quinazolinyl]amino}-2-fluoro-N-methylbenzenesulfonamide hydrochloride | 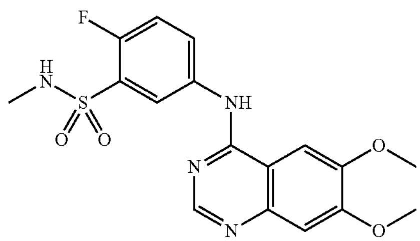 | 4-chloro-6,7-bis(methyloxy)quinazoline | 5-amino-2-fluoro-N-methylbenzenesulfonamide |
| 24 | 3-{[6,7-bis(methyloxy)-4-quinazolinyl]amino}-N-methyl-4-[(trifluoromethyl)oxy]benzenesulfonamide trifluoroacetate | 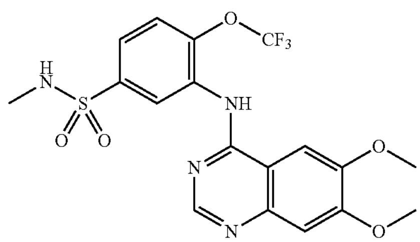 | 4-chloro-6,7-bis(methyloxy)quinazoline | 3-amino-N-methyl-4-[(trifluoromethyl)oxy]benzenesulfonamide |
| 25 | 3-{[6,7-bis(methyloxy)-4-quinazolinyl]amino}-N-methyl-4-(1-piperidinyl)benzenesulfonamide trifluoroacetate | 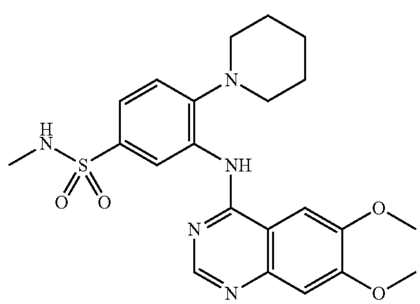 | 4-chloro-6,7-bis(methyloxy)quinazoline | 3-amino-N-methyl-4-(1-piperidinyl)benzenesulfonamide |
| 26 | 3-[(6-chloro-4-quinazolinyl)amino]-N-methyl-4-(1-piperidinyl)benzenesulfonamide trifluoroacetate | 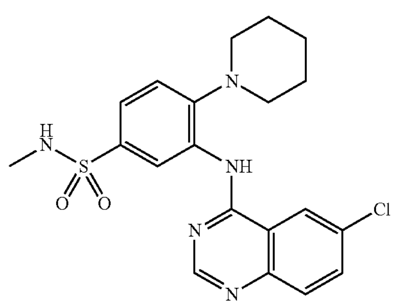 | 4,6-dichloroquinazoline | 3-amino-N-methyl-4-(1-piperidinyl)benzenesulfonamide |

-continued

| Ex. | Name | Structure | Quinazoline | Aniline |
|---|---|---|---|---|
| 27 | 3-{[6,7-bis(methyloxy)-4-quinazolinyl]amino}-4-(2,5-dimethyl-1-pyrrolidinyl)-N-methylbenzenesulfonamide trifluoroacetate | 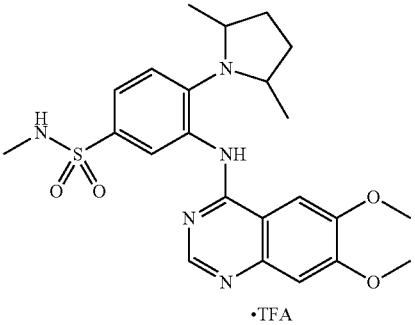 •TFA | 4-chloro-6,7-bis(methyloxy)quinazoline | 3-amino-4-(2,5-dimethyl-1-pyrrolidinyl)-N-methylbenzenesulfonamide |
| 28 | 3-[(6-chloro-4-quinazolinyl)amino]-4-(2,5-dimethyl-1-pyrrolidinyl)-N-methylbenzenesulfonamide trifluoroacetate | 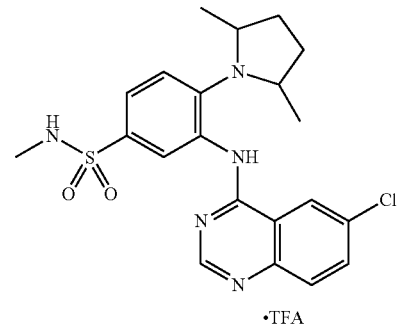 [SMILES: CNS(=O)(=O)c1ccc(N2C(C)CCC2C)c(Nc2ncnc3ccc(Cl)cc23)c1 ; "·TFA"] •TFA | 4,6-dichloro-quinazoline | 3-amino-4-(2,5-dimethyl-1-pyrrolidinyl)-N-methylbenzenesulfonamide |
| 29 | 3-{[6,7-bis(methyloxy)-4-quinazolinyl]amino}-N-methyl-4-[(2,2,2-trifluoroethyl)thio]benzenesulfonamide hydrochloride | 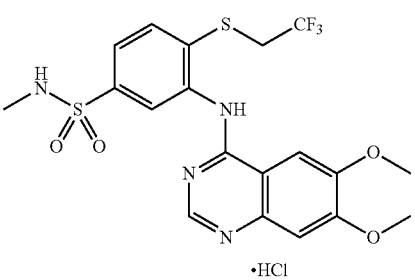 •HCl | 4-chloro-6,7-bis(methyloxy)quinazoline | 3-amino-N-methyl-4-[(2,2,2-trifluoroethyl)thio]benzene-sulfonamide |
| 30 | 3-{[5,7-bis(methyloxy)-4-quinazolinyl]amino}-N-methylbenzenesulfonamide hydrochloride | 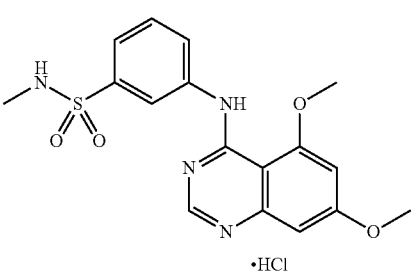 •HCl | 4-chloro-5,7-bis(methyloxy)quinazoline | 3-amino-N-methylbenzenesulfonamide |

Example 31

3-{[5,7-bis(methyloxy)-4-quinazolinyl]amino}-N-methyl-4-[(2,2,2-trifluoroethyl)oxy]benzenesulfonamide hydrochloride

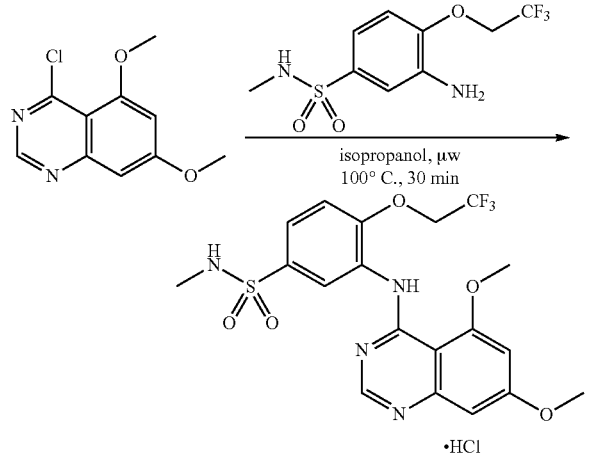

A mixture of 4-chloro-5,7-bis(methyloxy)quinazoline (75 mg, 0.334 mmol, prepared according to *J. Med. Chem.* (2006) 49 6465) and 3-amino-N-methyl-4-[(2,2,2-trifluoroethyl)oxy]benzenesulfonamide (95 mg, 0.334 mmol) in i-PrOH (2 mL) was subjected to microwave irradiation (100° C., 1 bar) for 30 minutes before being cooled to room temperature. The solid was collected by filtration, washed with i-PrOH, and dried under vacuum to give 3-{[5,7-bis(methyloxy)-4-quinazolinyl]amino}-N-methyl-4-[(2,2,2-trifluoroethyl)oxy]benzenesulfonamide hydrochloride (130 mg, 76%) as a yellow soid.

The following compounds were prepared with procedures analogous to that described in Example 31 using the specified quinazoline and aniline starting materials:

| Ex. | Name | Structure | Quinazoline | Aniline |
|---|---|---|---|---|
| 32 | 3-{[5,7-bis(methyloxy)-4-quinazolinyl]amino}-4-(dimethylamino)-N-methylbenzenesulfonamide | 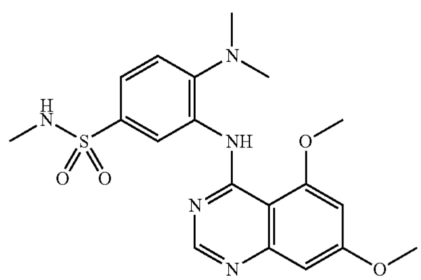 | 4-chloro-5,7-bis(methyloxy) quinazoline | 3-amino-4-(dimethylamino)-N-methylbenzene sulfonamide |
| 33 | 3-(5-chloro-6,7-dimethoxyquinazolin-4-ylamino)-N-methylbenzenesulfonamide trifluoroacetate | 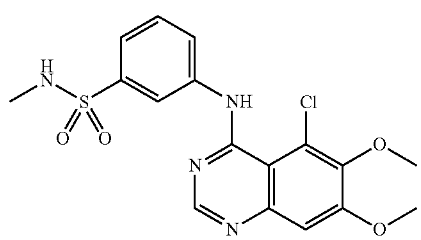 | 4,5-dichloro-6,7-bis(methyloxy) quinazoline | 3-amino-N-methylbenzene sulfonamide |
| 34 | 4-methoxy-3-(7-methoxy-6-(3-morpholinopropoxy) quinazolin-4-ylamino)-N-methylbenzenesulfonamide bis(trifluoroacetate) | 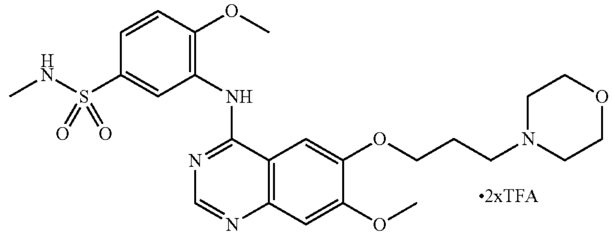 [SMILES: CNS(=O)(=O)c1ccc(OC)c(Nc2ncnc3cc(OC)c(OCCCN4CCOCC4)cc23)c1 ; "·2xTFA"] | 4-chloro-7-(methyloxy)-6-{[3-(4-morpholinyl) propyl]oxy} quinazoline (*J. Med. Chem.* (2004) 47 871) | 3-amino-N-methyl-4-(methyloxy) benzene-sulfonamide |

-continued

| Ex. | Name | Structure | Quinazoline | Aniline |
|---|---|---|---|---|
| 35 | 3-{[6,7-bis(methyloxy)-4-quinazolinyl]amino}-N-methyl-4-[methyl(2,2,2-trifluoroethyl)amino]benzenesulfonamide trifluoroacetate | 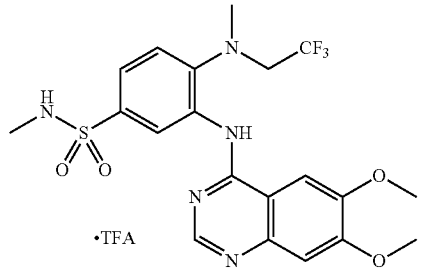 | 4-chloro-6,7-bis(methyloxy)quinazoline | 3-amino-N-methyl-4-[methyl(2,2,2-trifluoroethyl)amino]benzene-sulfonamide |
| 36 | 3-{[5,7-bis(methyloxy)-4-quinazolinyl]amino}-N-methyl-4-[methyl(2,2,2-trifluoroethyl)amino]benzenesulfonamide hydrochloride | 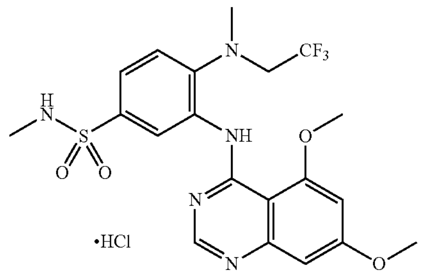 | 4-chloro-5,7-bis(methyloxy)quinazoline | 3-amino-N-methyl-4-[methyl(2,2,2-trifluoroethyl)amino]benzene-sulfonamide |
| 37 | 3-{[5,7-bis(methyloxy)-4-quinazolinyl]amino}-N-methyl-4-(methyloxy)benzenesulfonamide hydrochloride | 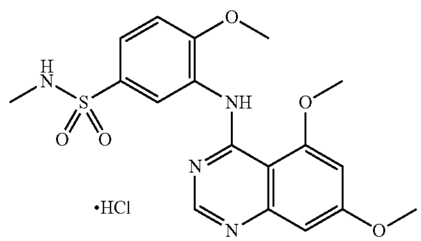 | 4-chloro-5,7-bis(methyloxy)quinazoline | 3-amino-N-methyl-4-(methyloxy)benzene-sulfonamide |
| 38 | 3-{[5,7-bis(methyloxy)-4-quinazolinyl]amino}-4-fluoro-N-methylbenzenesulfonamide hydrochloride | 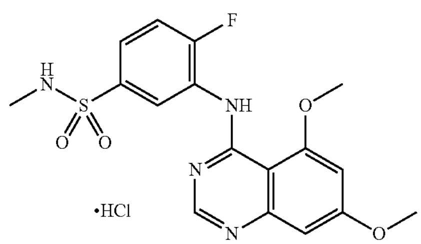 | 4-chloro-5,7-bis(methyloxy)quinazoline | 3-amino-4-fluoro-N-methylbenzene sulfonamide |
| 39 | 3-{[5,7-bis(methyloxy)-4-quinazolinyl]amino}-4-chloro-N-methylbenzenesulfonamide hydrochloride | 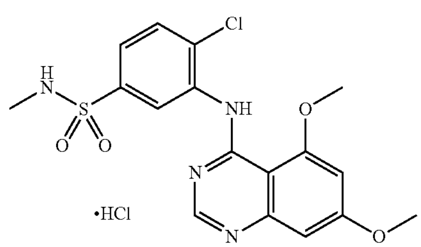 | 4-chloro-5,7-bis(methyloxy)quinazoline | 3-amino-4-chloro-N-methylbenzene sulfonamide |
| 40 | 3-{[5,7-bis(methyloxy)-4-quinazolinyl]amino}-N-methyl-4-(4-morpholinyl)benzenesulfonamide hydrochloride | 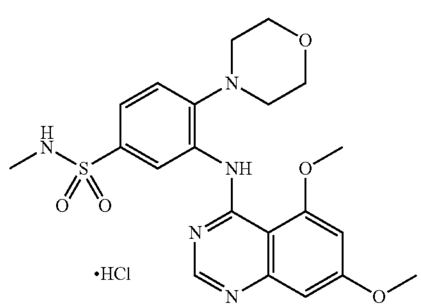 | 4-chloro-5,7-bis(methyloxy)quinazoline | 3-amino-N-methyl-4-(4-morpholinyl)benzene-sulfonamide |

-continued

| Ex. | Name | Structure | Quinazoline | Aniline |
|---|---|---|---|---|
| 41 | 5-{[6,7-bis(methyloxy)-4-quinazolinyl]amino}-2-fluoro-N-methyl-4-(methyloxy)benzenesulfonamide hydrochloride | 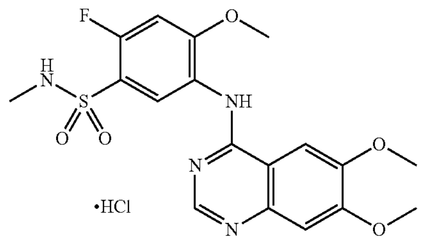 | 4-chloro-6,7-bis(methyloxy)quinazoline | 5-amino-2-fluoro-N-methyl-4-(methyloxy)benzene-sulfonamide |
| 42 | 3-{[6-(ethyloxy)-7-(methyloxy)-4-quinazolinyl]amino}-N-methyl-4-[(2,2,2-trifluoroethyl)oxy]benzenesulfonamide hydrochloride | 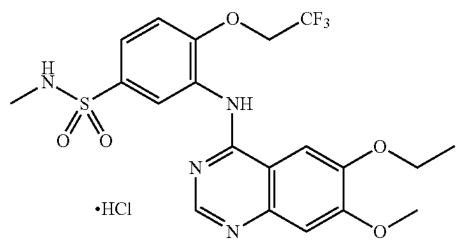 [SMILES: CCOc1cc2c(Nc3cc(S(=O)(=O)NC)ccc3OCC(F)(F)F)ncnc2cc1OC ; Cl] | 4-chloro-6-(ethyloxy)-7-(methyloxy)quinazoline | 3-amino-N-methyl-4-[(2,2,2-trifluoroethyl)oxy]benzene-sulfonamide |
| 43 | 4-(dimethylamino)-3-(7-methoxy-6-(3-morpholinopropoxy)quinazolin-4-ylamino)-N-methylbenzenesulfonamide bis(formate) | 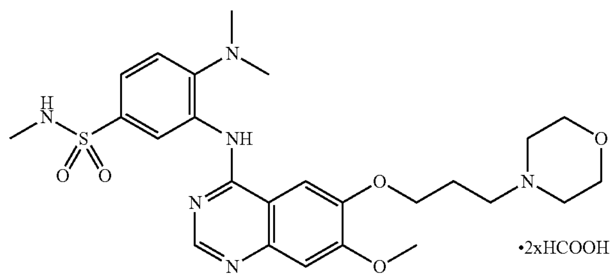 [SMILES: CNS(=O)(=O)c1ccc(N(C)C)c(Nc2ncnc3cc(OC)c(OCCCN4CCOCC4)cc23)c1 ; "·2xHCOOH"] | 4-chloro-7-(methyloxy)-6-{[3-(4-morpholinyl)propyl]oxy}quinazoline | 3-amino-4-(dimethylamino)-N-methylbenzenesulfonamide |
| 44 | N-methyl-3-{[6-[(1-methylethyl)oxy]-7-(methyloxy)-4-quinazolinyl]amino}-4-[(2,2,2-trifluoroethyl)oxy]benzenesulfonamide hydrochloride | 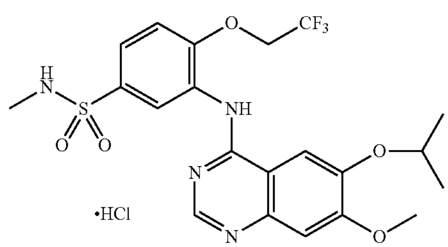 [SMILES: CNS(=O)(=O)c1ccc(OCC(F)(F)F)c(Nc2ncnc3cc(OC)c(OC(C)C)cc23)c1 ; Cl] | 4-chloro-6-[(1-methylethyl)oxy]-7-(methyloxy)quinazoline | 3-amino-N-methyl-4-[(2,2,2-trifluoroethyl)oxy]benzenesulfonamide |
| 45 | 3-({7-[(3-chloropropyl)oxy]-4-quinazolinyl}amino)-N-methyl-4-[(2,2,2-trifluoroethyl)oxy]benzenesulfonamide | 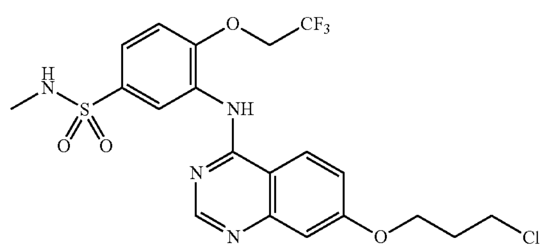 [SMILES: CNS(=O)(=O)c1ccc(OCC(F)(F)F)c(Nc2ncnc3cc(OCCCCl)ccc23)c1] | 4-chloro-7-[(3-chloropropyl)oxy]quinazoline | 3-amino-N-methyl-4-[(2,2,2-trifluoroethyl)oxy]benzene-sulfonamide |
| 46 | 3-{[5-(ethyloxy)-7-(methyloxy)-4-quinazolinyl]amino}-N-methyl-4-[(2,2,2-trifluoroethyl)oxy]benzenesulfonamide | 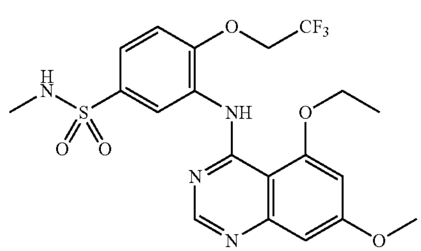 | 4-chloro-5-(ethyloxy)-7-(methyloxy)quinazoline | 3-amino-N-methyl-4-[(2,2,2-trifluoroethyl)oxy]benzene-sulfonamide |

-continued

| Ex. | Name | Structure | Quinazoline | Aniline |
|---|---|---|---|---|
| 47 | N-methyl-3-{[5-[(1-methylethyl)oxy]-7-(methyloxy)-4-quinazolinyl]amino}-4-[(2,2,2-trifluoroethyl)oxy]benzenesulfonamide | 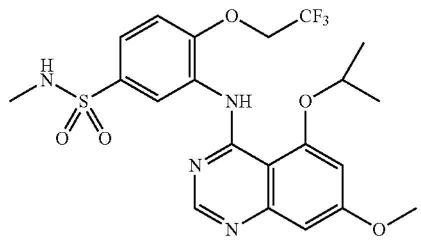 | 4-chloro-5-[(1-methylethyl)oxy]-7-(methyloxy)quinazoline | 3-amino-N-methyl-4-[(2,2,2-trifluoroethyl)oxy]benzenesulfonamide |
| 48 | N-methyl-4-[(2,2,2-trifluoroethyl)oxy]-3-{[5,6,7-tris(methyloxy)-4-quinazolinyl]amino}benzenesulfonamide hydrochloride | ·HCl | 4-chloro-5,6,7-tris(methyloxy)quinazoline | 3-amino-N-methyl-4-((2,2,2-trifluoroethyl)oxy]benzenesulfonamide |
| 49 | 3-{[5,7-bis(methyloxy)-4-quinazolinyl]amino}-N-methyl-4-[(2,2,2-trifluoro-1-methylethyl)oxy]benzenesulfonamide trifluoroacetate | ·TFA | 4-chloro-5,7-bis(methyloxy)quinazoline | 3-amino-N-methyl-4-[(2,2,2-trifluoro-1-methylethyl)oxy]benzenesulfonamide |
| 50 | 5-{[5,7-bis(methyloxy)-4-quinazolinyl]amino}-2-fluoro-N-methyl-4-[(2,2,2-trifluoroethyl)oxy]benzenesulfonamide trifluoroacetate | ·TFA | 4-chloro-5,7-bis(methyloxy)quinazoline | 5-amino-2-fluoro-N-methyl-4-[(2,2,2-trifluoroethyl)oxy]benzenesulfonamide |
| 51 | 5-{[5,7-bis(methyloxy)-4-quinazolinyl]amino}-2-fluoro-N-methyl-4-(methyloxy)benzenesulfonamide trifluoroacetate | ·TFA | 4-chloro-5,7-bis(methyloxy)quinazoline | 5-amino-2-fluoro-N-methyl-4-(methyloxy)benzenesulfonamide |
| 52 | 5-{[6,7-bis(methyloxy)-4-quinazolinyl]amino}-2-fluoro-N-methyl-4-[(2,2,2-trifluoroethyl)oxy]benzenesulfonamide hydrochloride | ·HCl | 4-chloro-6,7-bis(methyloxy)quinazoline | 5-amino-2-fluoro-N-methyl-4-[(2,2,2-trifluoroethyl)oxy]benzenesulfonamide |

| Ex. | Name | Structure | Quinazoline | Aniline |
|---|---|---|---|---|
| 53 | 3-{[5,7-bis(methyloxy)-4-quinazolinyl]amino}-N-methyl-4-(methylthio)benzenesulfonamide hydrochloride | 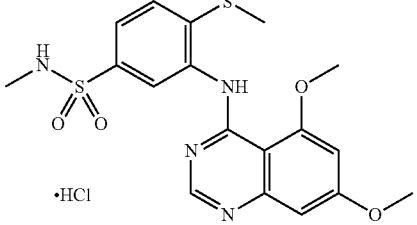 •HCl | 4-chloro-5,7-bis(methyloxy)quinazoline | 3-amino-N-methyl-4-(methylthio)benzene-sulfonamide |
| 54 | 3-{[5,7-bis(methyloxy)-4-quinazolinyl]amino}-N-methyl-4-[(trifluoromethyl)oxy]benzenesulfonamide hydrochloride | 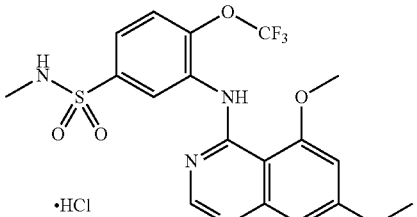 •HCl | 4-chloro-5,7-bis(methyloxy)quinazoline | 3-amino-N-methyl-4-[(trifluoromethyl)oxy]benzene-sulfonamide |
| 55 | N-methyl-4-[(trifluoromethyl)oxy]-3-{[5,6,7-tris(methyloxy)-4-quinazolinyl]amino}benzene sulfonamide trifluoroacetate | 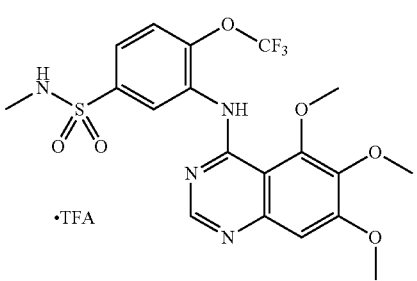 •TFA | 4-chloro-5,6,7-tris(methyloxy)quinazoline | 3-amino-N-methyl-4-[(trifluoromethyl)oxy]benzene-sulfonamide |
| 56 | 5-{[5,7-bis(methyloxy)-4-quinazolinyl]amino}-4-(dimethylamino)-2-fluoro-N-methylbenzenesulfonamide hydrochloride | 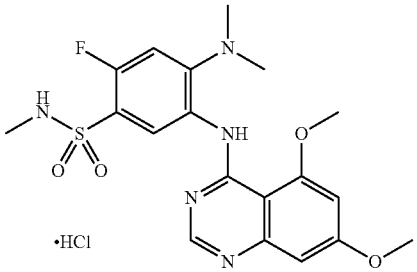 •HCl | 4-chloro-5,7-bis(methyloxy)quinazoline | 5-amino-4-(dimethylamino)-2-fluoro-N-methylbenzene sulfonamide |
| 57 | 5-{[6,7-bis(methyloxy)-4-quinazolinyl]amino}-4-(dimethylamino)-2-fluoro-N-methylbenzenesulfonamide hydrochloride | 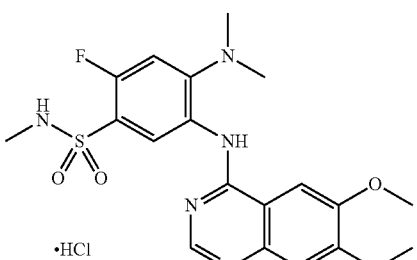 •HCl | 4-chloro-6,7-bis(methyloxy)quinazoline | 5-amino-4-(dimethylamino)-2-fluoro-N-methylbenzene sulfonamide |
| 58 | 2-fluoro-N-methyl-4-[(2,2,2-trifluoroethyl)oxy]-5-{[5,6,7-tris(methyloxy)-4-quinazolinyl]amino}benzene sulfonamide trifluoroacetate | 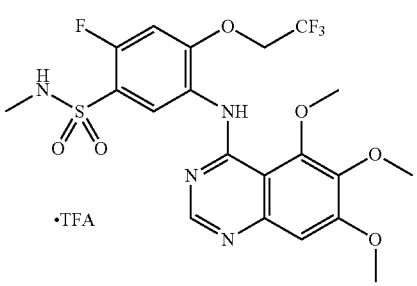 •TFA | 4-chloro 5,6,7-tris(methyloxy)quinazoline | 5-amino-2-fluoro-N-methyl-4-[(2,2,2-trifluoroethyl)oxy]benzene-sulfonamide |

-continued

| Ex. | Name | Structure | Quinazoline | Aniline |
|---|---|---|---|---|
| 59 | 4-chloro-N-methyl-3-{[5,6,7-tris(methyloxy)-4-quinazolinyl]amino}benzene sulfonamide trifluoroacetate | 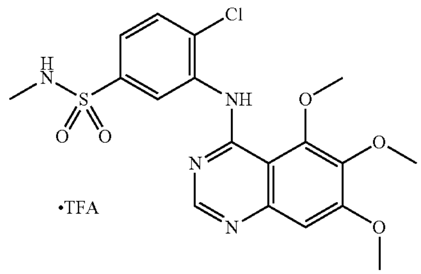 | 4-chloro-5,6,7-tris(methyloxy) quinazoline | 3-amino-4-chloro-N-methylbenzene sulfonamide |
| 60 | N-methyl-3-[(7-(methyloxy)-5-{[2-(methyloxy)ethyl]oxy}-4-quinazolinyl)amino]-4-[(2,2,2-trifluoroethyl)oxy]benzene-sulfonamide hydrochloride | 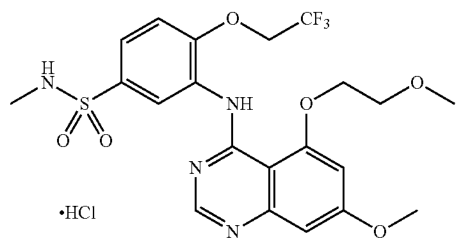 | 4-chloro-7-(methyloxy)-5-{[2-(methyloxy)ethyl]oxy} quinazoline | 3-amino-N-methyl-4-[(2,2,2-trifluoroethyl)oxy]benzene-sulfonamide |
| 61 | N-methyl-3-{[7-(methyloxy)-5-(tetrahydro-2H-pyran-4-yloxy)-4-quinazolinyl]amino}-4-[(2,2,2-trifluoroethyl)oxy]benzenesulfonamide | 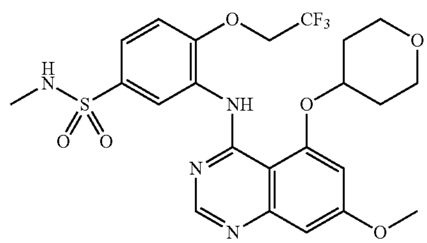 [SMILES: CNS(=O)(=O)c1ccc(OCC(F)(F)F)c(Nc2ncnc3cc(OC)cc(OC4CCOCC4)c23)c1] | 4-chloro-7-(methyloxy)-5-(tetrahydro-2H-pyran-4-yloxy) quinazoline | 3-amino-N-methyl-4-[(2,2,2-trifluoroethyl)oxy]benzene-sulfonamide |
| 62 | N-methyl-4-[(2,2,2-trifluoro-1-methylethyl)oxy]-3-{[5,6,7-tris(methyloxy)-4-quinazolinyl]amino}benzene sulfonamide trifluoroacetate | 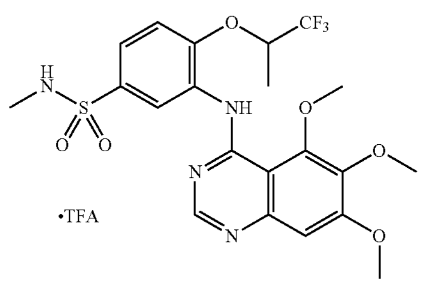 | 4-chloro-5,6,7-tris(methyloxy) quinazoline | 3-amino-N-methyl-4-[(2,2,2-trifluoro-1-methylethyl)oxy]benzene-sulfonamide |
| 63 | N-methyl-4-(methylsulfonyl)-3-{[5,6,7-tris(methyloxy)-4-quinazolinyl]amino}benzene sulfonamide trifluoroacetate | 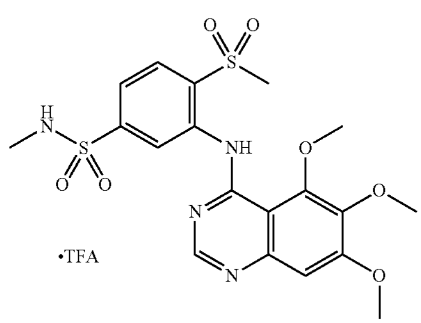 | 4-chloro-5,6,7-tris(methyloxy) quinazoline | 3-amino-N-methyl-4-(methylsulfonyl) benzene-sulfonamide |

-continued

| Ex. | Name | Structure | Quinazoline | Aniline |
|---|---|---|---|---|
| 64 | 3-{[5-(ethyloxy)-7-(methyloxy)-4-quinazolinyl]amino}-N-methyl-4-[(trifluoromethyl)oxy]benzenesulfonamide | 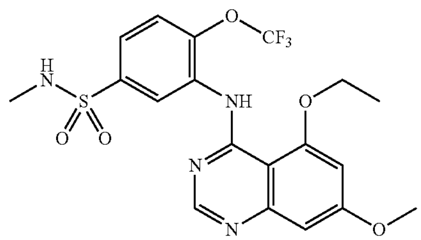 | 4-chloro-5-(ethyloxy)-7-(methyloxy)quinazoline | 3-amino-N-methyl-4-[(trifluoromethyl)oxy]benzene-sulfonamide |
| 65 | N-methyl-3-{[5-[(1-methylethyl)oxy]-7-(methyloxy)-4-quinazolinyl]amino}-4-[(trifluoromethyl)oxy]benzenesulfonamide | 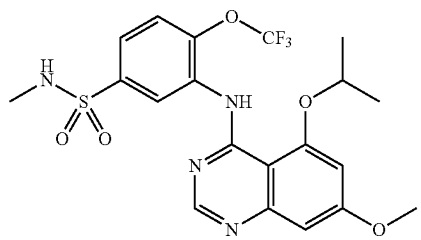 | 4-chloro-5-[(1-methylethyl)oxy]-7-(methyloxy)quinazoline | 3-amino-N-methyl-4-[(trifluoromethyl)oxy]benzenesulfonamide |
| 66 | 3-{[5-(ethyloxy)-7-(methyloxy)-4-quinazolinyl]amino}-N-methyl-4-[(2,2,2-trifluoro-1-methylethyl)oxy]benzenesulfonamide | 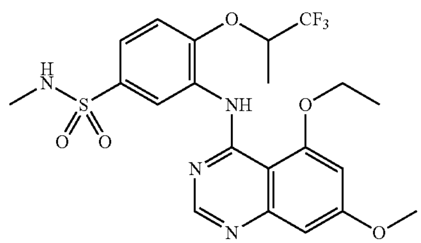 | 4-chloro-5-(ethyloxy)-7-(methyloxy)quinazoline | 3-amino-N-methyl-4-[(2,2,2-trifluoro-1-methylethyl)oxy]benzene-sulfonamide |
| 67 | N-methyl-3-{[5-[(1-methylethyl)oxy]-7-(methyloxy)-4-quinazolinyl]amino}-4-[(2,2,2-trifluoro-1-methylethyl)oxy]benzenesulfonamide | 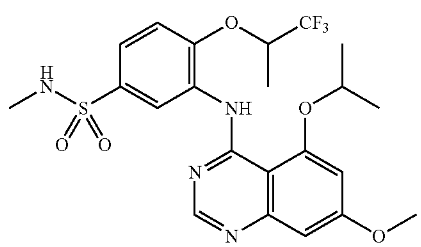 | 4-chloro-5-[(1-methylethyl)oxy]-7-(methyloxy)quinazoline | 3-amino-N-methyl-4-[(2,2,2-trifluoro-1-methylethyl)oxy]benzene-sulfonamide |
| 68 | 3-{[6,7-bis(methyloxy)-4-quinazolinyl]amino}-N-methyl-4-(methylsulfonyl)benzenesulfonamide trifluoroacetate | 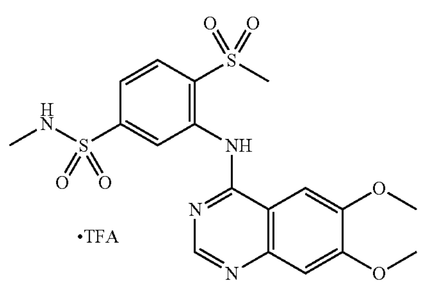 | 4-chloro-6,7-bis(methyloxy)quinazoline | 3-amino-N-methyl-4-(methylsulfonyl)benzene-sulfonamide |
| 69 | 3-{[6,7-bis(methyloxy)-4-quinazolinyl]amino}-N-methyl-4-[(2,2,2-trifluoro-1-methylethyl)oxy]benzenesulfonamide | 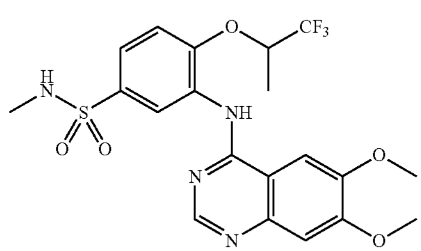 | 4-chloro-6,7-bis(methyloxy)quinazoline | 3-amino-N-methyl-4-[(2,2,2-trifluoro-1-methylethyl)oxy]benzene-sulfonamide |

-continued

| Ex. | Name | Structure | Quinazoline | Aniline |
|---|---|---|---|---|
| 70 | 3-{[6-iodo-7-(methyloxy)-4-quinazolinyl]amino}-N-methyl-4-[(2,2,2-trifluoroethyl)oxy]benzenesulfonamide | 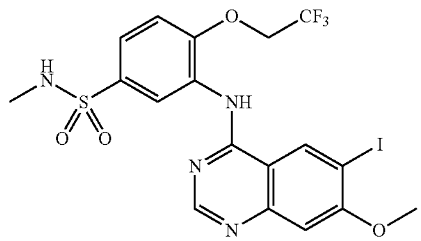 | 4-chloro-6-iodo-7-(methyloxy)quinazoline | 3-amino-N-methyl-4-[(2,2,2-trifluoroethyl)oxy]benzenesulfonamide |
| 71 | 3-{[6,7-bis(ethyloxy)-4-quinazolinyl]amino}-N-methyl-4-[(2,2,2-trifluoroethyl)oxy]benzenesulfonamide | 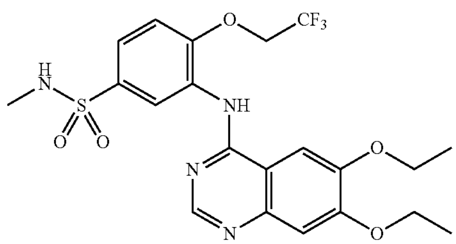 [SMILES: CCOc1cc2ncnc(Nc3cc(S(=O)(=O)NC)ccc3OCC(F)(F)F)c2cc1OCC] | 4-chloro-6,7-bis(ethyloxy)quinazoline (*J. Med. Chem.* (2005) 48 7445) | 3-amino-N-methyl-4-[(2,2,2-trifluoroethyl)oxy]benzenesulfonamide |
| 72 | 4-(dimethylamino)-N-methyl-3-((7-nitroquinazolin-4-yl)amino)benzenesulfonamide hydrochloride | 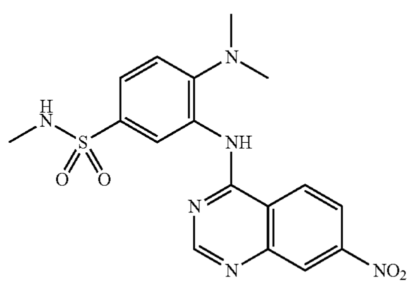 [SMILES: CNS(=O)(=O)c1ccc(N(C)C)c(Nc2ncnc3cc([N+](=O)[O-])ccc23)c1] | 4-chloro-7-nitroquinazoline | 3-amino-4-(dimethylamino)-N-methylbenzenesulfonamide |

Example 73

4-(dimethylamino)-N-methyl-3-[(7-{[3-(4-morpholinyl)propyl]oxy}-4-quinazolinyl)amino]benzenesulfonamide hydrochloride

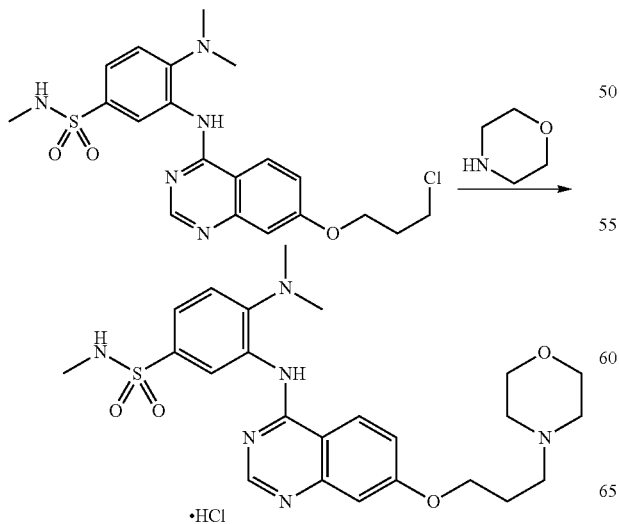

A mixture of 3-({7-[(3-chloropropyl)oxy]-4-quinazolinyl}amino)-4-(dimethylamino)-N-methylbenzenesulfonamide (50 mg, 0.111 mmol) and morpholine (0.048 mL, 0.556 mmol) in MeOH (1 mL) was stirred at 90° C. for 3 days before being cooled and concentrated. The residue was triturated with Et$_2$O-EtOAc and the resulting solid was collected by filtration, washed with Et$_2$O, and dried to give 4-(dimethylamino)-N-methyl-3-[(7-{[3-(4-morpholinyl)propyl]oxy}-4-quinazolinyl)amino]benzenesulfonamide hydrochloride (33 mg, 48%) as an off-white solid.

The following compound was prepared with procedures analogous to that described in Example 73 using the specified quinazoline starting material:

| Ex. | Name | Structure | Quinazoline SM |
|---|---|---|---|
| 74 | N-methyl-3-[(7-{[3-(4-morpholinyl)propyl]oxy}-4-quinazolinyl)amino]-4-[(2,2,2-trifluoroethyl)oxy]benzenesulfonamide trifluoroacetate | ·TFA | 3-({7-[(3-chloropropyl)oxy]-4-quinazolinyl}amino)-N-methyl-4-[(2,2,2-trifluoroethyl)oxy]benzenesulfonamide |

Example 75

N-methyl-3-[(7-{[3-(methyloxy)propyl]oxy}-4-quinazolinyl)amino]-4-[(2,2,2-trifluoroethyl)oxy]benzenesulfonamide

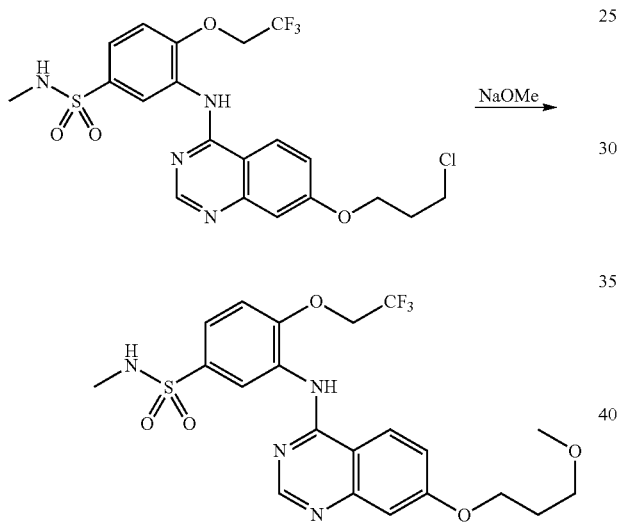

A mixture of 3-({7-[(3-chloropropyl)oxy]-4-quinazolinyl}amino)-N-methyl-4-[(2,2,2-trifluoroethyl)oxy]benzenesulfonamide (150 mg, 0.297 mmol) in MeOH (3 mL) was treated with a solution of 25% sodium methoxide in methanol (3 g, 13.88 mmol) and subjected to microwave irradiation (100° C.) for 10 minutes before being cooled and neutralized with the addition of concentrated HCl. The resulting solution was diluted with saturated aqueous NaHCO₃ and extracted with CH₂Cl₂. The organic extracts were dried (sodium sulfate), concentrated, and subjected to reverse phase HPLC (30-70% MeCN/aq. NH₄OH pH 10, XBridge C18 OBD 30×150 mm, 5 µm) to give N-methyl-3-[(7-{[3-(methyloxy)propyl]oxy}-4-quinazolinyl)amino]-4-[(2,2,2-trifluoroethyl)oxy]benzenesulfonamide (37 mg, 25%) as a white solid.

The following compound was prepared with procedures analogous to that described in Example 75 using the specified quinazoline starting material:

| Ex. | Name | Structure | Quinazoline SM |
|---|---|---|---|
| 76 | 4-(dimethylamino)-N-methyl-3-[(7-{[3-(methyloxy)propyl]oxy}-4-quinazolinyl)amino]benzenesulfonamide | 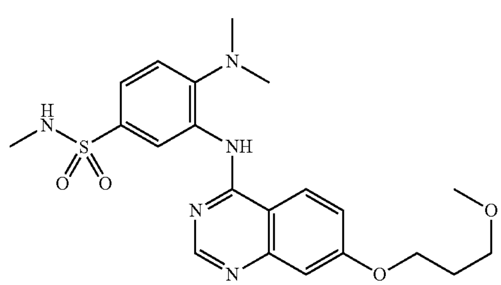 [SMILES: CNS(=O)(=O)c1ccc(N(C)C)c(Nc2ncnc3cc(OCCCOC)ccc23)c1] | 3-({7-[(3-chloropropyl)oxy]-4-quinazolinyl}amino)-4-(dimethylamino)-N-methyl-benzenesulfonamide |

Example 77

3-{[5,7-bis(methyloxy)-4-quinazolinyl]amino}-N-methyl-4-(methylsulfonyl)benzenesulfonamide trifluoroacetate

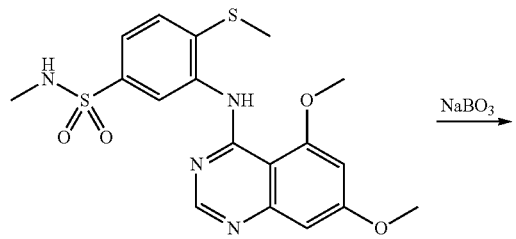

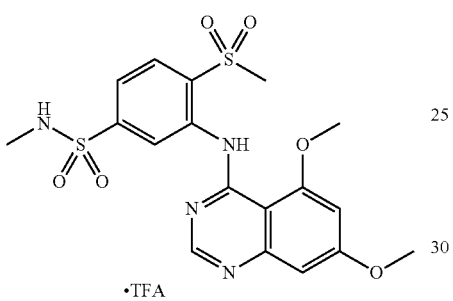

A mixture of 3-{[5,7-bis(methyloxy)-4-quinazolinyl]amino}-N-methyl-4-(methylthio)benzenesulfonamide (200 mg, 0.476 mmol) and sodium perborate tetrahydrate (220 mg, 1.427 mmol) in AcOH (1.902 ml) was heated at 50° C. for 2 hours before being filtered and extracted with EtOAc. The organic extract was washed with water, saturated aqueous NaHCO₃, and brine, then dried (sodium sulfate), concentrated, and subjected to reverse phase HPLC (Sunfire prep C18 OBD, 30×150 mm, 10-50% Water/CH₃CN+0.1% TFA) to give 3-{[5,7-bis(methyloxy)-4-quinazolinyl]amino}-N-methyl-4-(methylsulfonyl)benzenesulfonamide trifluoroacetate (28 mg, 10%) as a white solid.

Example 78

3-(7-hydroxy-6-methoxyquinazolin-4-ylamino)-N-methyl-4-(2,2,2-trifluoroethoxy)benzenesulfonamide

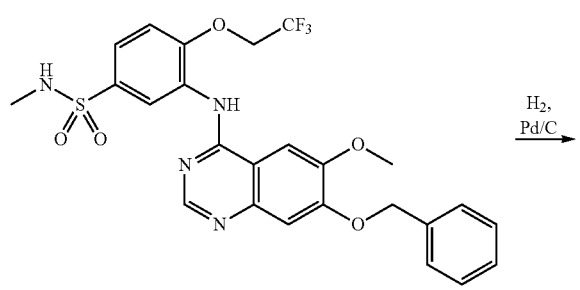

A mixture of N-methyl-3-({6-(methyloxy)-7-[(phenylmethyl)oxy]-4-quinazolinyl}amino)-4-[(2,2,2-trifluoroethyl)oxy]benzenesulfonamide (4.2 g, 7.66 mmol) in EtOAc (120 mL), MeOH (40 mL), and DMF (40 mL) was treated with 60% AcOH (0.4 mL) and Pd/C (400 mg) was stirred under H₂ (balloon) for 2 hours before being filtered and concentrated to give 3-(7-hydroxy-6-methoxyquinazolin-4-ylamino)-N-methyl-4-(2,2,2-trifluoroethoxy)benzenesulfonamide (3.2 g, 91%) as a yellow solid.

Example 79

3-(7-isopropoxy-6-methoxy-quinazolin-4-ylamino)-N-methyl-4-(2,2,2-trifluoro-ethoxy)-benzenesulfonamide

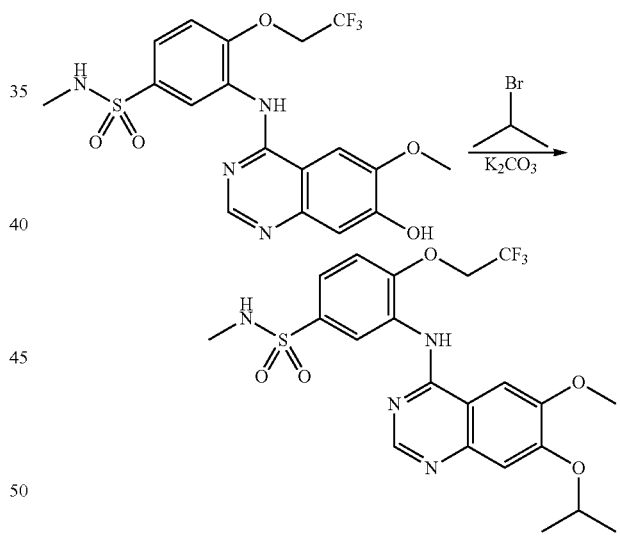

A solution of 3-{[7-hydroxy-6-(methyloxy)-4-quinazolinyl]amino}-N-methyl-4-[(2,2,2-trifluoroethyl)oxy]benzenesulfonamide (170 mg, 0.37 mmol) in DMF (5 mL) was treated with 2-bromopropane (181 mg, 1.48 mmol) and K₂CO₃ (154 mg, 1.11 mmol) and stirred at 60° C. for 16 hours before being poured into water. The precipitate that formed was collected by filtration, washed with MeOH, and dried to give 3-(7-isopropoxy-6-methoxy-quinazolin-4-ylamino)-N-methyl-4-(2,2,2-trifluoro-ethoxy)-benzenesulfonamide (80 mg, 43%) as an off-white solid.

The following compounds were prepared with procedures analogous to that described in Example 79 using the indicated alkyl halide:

| Ex. | Name | Structure | Alkyl Halide |
|---|---|---|---|
| 80 | 3-(7-ethoxy-6-methoxy-quinazolin-4-ylamino)-N-methyl-4-(2,2,2-trifluoro-ethoxy)-benzenesulfonamide trifluoroacetate | 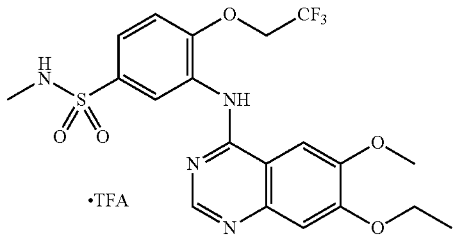 [SMILES: CCOc1cc2ncnc(Nc3cc(S(=O)(=O)NC)ccc3OCC(F)(F)F)c2cc1OC] | bromoethane |
| 81 | 3-[6-methoxy-7-(2-methoxy-ethoxy)-quinazolin-4-ylamino]-N-methyl-4-(2,2,2-trifluoro-ethoxy)-benzenesulfonamide trifluoroacetate | 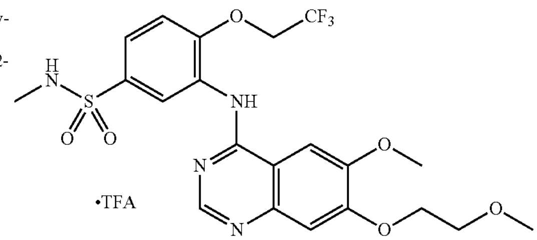 | 1-bromo-2-(methyloxy)ethane |

Examples 82 & 83

3-{[5,7-bis(methyloxy)-4-quinazolinyl]amino}-N-methyl-4-[(2,2,2-trifluoro-1-methylethyl)oxy]benzenesulfonamide hydrochloride (enantiomer 1) & 3-{[5,7-bis(methyloxy)-4-quinazolinyl]amino}-N-methyl-4-[(2,2,2-trifluoro-1-methylethyl)oxy]benzenesulfonamide hydrochloride (enantiomer 2)

A racemic mixture of 3-{[5,7-bis(methyloxy)-4-quinazolinyl]amino}-N-methyl-4-[(2,2,2-trifluoro-1-methylethyl)oxy]benzenesulfonamide hydrochloride (528 mg) was subjected to chiral SFC (Chiralpak OJ-H, 15% MeOH cosolvent) to provide 3-{[5,7-bis(methyloxy)-4-quinazolinyl]amino}-N-methyl-4-[(2,2,2-trifluoro-1-methylethyl)oxy]benzenesulfonamide hydrochloride (unassigned enantiomer 1, 33mg) & 3-{[5,7-bis(methyloxy)-4-quinazolinyl]amino}-N-methyl-4-[(2,2,2-trifluoro-1-methylethyl)oxy]benzenesulfonamide hydrochloride (unassigned enantiomer 2, 49 mg).

Example 84

3-((6-aminoquinazolin-4-yl)amino)-4-(dimethylamino)-N-methylbenzenesulfonamide

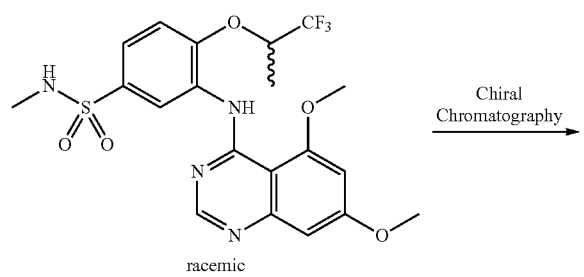
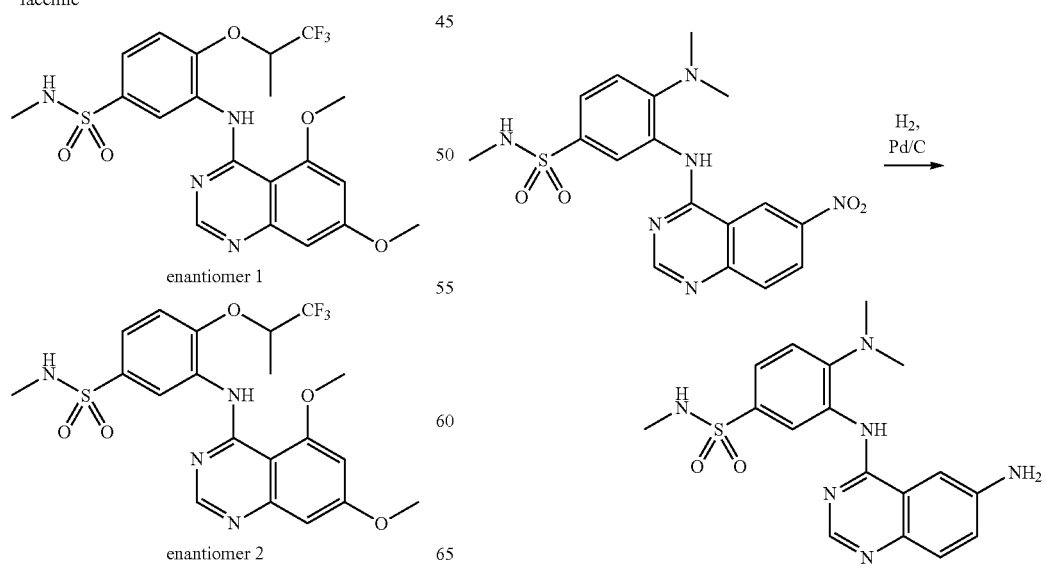

A mixture of 4-(dimethylamino)-N-methyl-3-((6-nitroquinazolin-4-yl)amino)benzene-sulfonamide (715 mg, 1.78 mmol) in MeOH (50 mL) was treated with 10% Pd/C (189 mg, 0.178 mmol) and stirred under $H_2$ (balloon) at 25° C. for 2.5 hours before being filtered through celite and concentrated. The residue was dissolved in $CH_2Cl_2$/MeOH, washed with saturated aqueous $NaHCO_3$, dried ($Na_2SO_4$), and concentrated to give 3-((6-aminoquinazolin-4-yl)amino)-4-(dimethylamino)-N-methylbenzenesulfonamide (433 mg, 59%) as a yellow solid.

The following compound was prepared with procedures analogous to that described in Example 84:

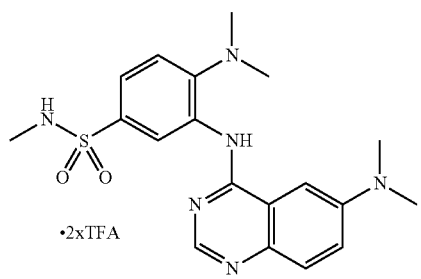

•2xTFA

| Ex. | Name | Structure | Quinazoline SM |
|---|---|---|---|
| 85 | 3-((7-aminoquinazolin-4-yl)amino)-4-(dimethylamino)-N-methylbenzenesulfonamide | 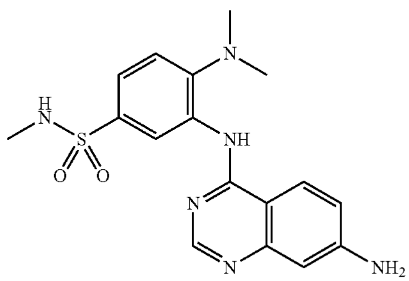 | 4-(dimethylamino)-N-methyl-3-[(7-nitro-4-quinazolinyl)amino]benzenesulfonamide |

Example 86

4-(dimethylamino)-3-((6-(dimethylamino)quinazolin-4-yl)amino)-N-methylbenzenesulfonamide bis(trifluoroacetate) &

Example 87

4-(dimethylamino)-N-methyl-3-((6-(methylamino)quinazolin-4-yl)amino)benzenesulfonamide bis(trifluoroacetate)

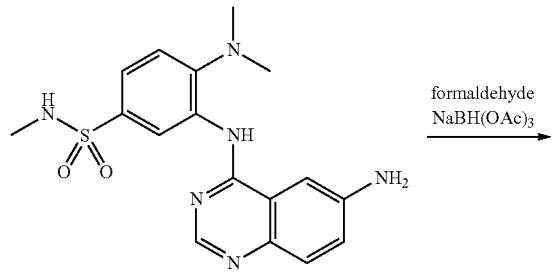

formaldehyde
NaBH(OAc)₃

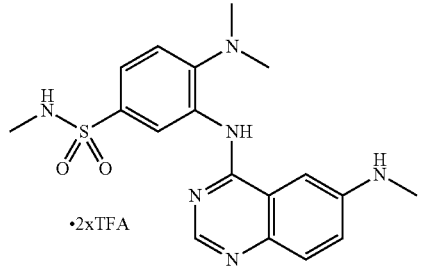

•2xTFA

A mixture of 3-((6-aminoquinazolin-4-yl)amino)-4-(dimethylamino)-N-methylbenzene-sulfonamide (129 mg, 0.346 mmol) in $CH_2Cl_2$ (3 mL) was treated with AcOH (0.022 mL, 0.381 mmol) and 37% aqueous formaldehyde (0.028 mL, 0.381 mmol) and stirred at 25° C. After 5 minutes, sodium triacetoxyborohydride (110 mg, 0.520 mmol) was added and the mixture was stirred for 2 hours before being quenched with the addition of saturated aqueous $NaHCO_3$ and extracted with a $CH_2Cl_2$/MeOH mixture. The organic extract was dried ($Na_2SO_4$), concentrated, and subjected to reverse phase HPLC (10-40% MeCN/$H_2O$/0.1% TFA on a Sunfire™ Prep C18 OBD™ 5 μm 30×150 mm column) to give 4-(dimethylamino)-N-methyl-3-((6-(methylamino)quinazolin-4-yl)amino)benzene-sulfonamide (3 mg, 1.4%) as a yellow solid and 4-(dimethylamino)-3-((6-(dimethylamino)quinazolin-4-yl)amino)-N-methylbenzenesulfonamide (3.6 mg, 1.6%) as a yellow solid.

The following compound was prepared with procedures analogous to that described in Examples 86 & 87:

| Ex. | Name | Structure | Quinazoline SM |
|---|---|---|---|
| 88 | 4-(dimethylamino)-N-methyl-3-((7-(methylamino)quinazolin-4-yl)amino) benzenesulfonamide | 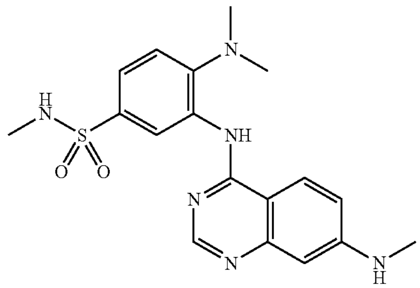 | 3-((7-aminoquinazolin-4-yl)amino)-4-(dimethylamino)-N-methylbenzene-sulfonamide |

Spectroscopic Data For Examples 1-88

| Ex. | Name | $t_R$ (min) | MS (m/z) | $^1$H NMR |
|---|---|---|---|---|
| 1 | 3-{[6,7-bis(methyloxy)-4-quinazolinyl]amino}-4-(dimethylamino)-N-methylbenzenesulfonamide hydrochloride | 2.06$^a$ | 418 | $^1$H NMR (400 MHz, DMSO-d$_6$) δ 11.38 (br. s., 1H), 8.81 (s, 1H), 8.29 (s, 1H), 7.59-7.71 (m, 2H), 7.31-7.39 (m, 2H), 7.23 (d, J = 9.54 Hz, 1H), 4.00 (s, 3H), 4.01 (s, 3H), 2.82 (s, 6H), 2.43 (d, J = 4.27 Hz, 3H) |
| 2 | 3-{[6,7-bis(methyloxy)-4-quinazolinyl]amino}-N-methylbenzenesulfonamide hydrochloride | 1.81$^a$ | 375.1 | $^1$H NMR (400 MHz, DMSO-d$_6$) δ 10.98 (br. s., 1H), 8.85 (s, 1H), 8.05-8.18 (m, 3H), 7.73 (t, J = 7.91 Hz, 1H), 7.67 (d, J = 7.78 Hz, 1H), 7.59 (q, J = 4.43 Hz, 1H), 7.29 (s, 1H), 4.02 (d, J = 3.76 Hz, 6H), 2.48 (s, 3H) |
| 3 | 3-{[6,7-bis(methyloxy)-4-quinazolinyl]amino}-N-methyl-4-(4-morpholinyl)benzene-sulfonamide trifluoroacetate | 1.78$^a$ | 459.9 | $^1$H NMR (400 MHz, DMSO-d$_6$) δ 10.66 (br. s., 1H), 8.76 (s, 1H), 8.05 (s, 1H), 7.92-7.98 (m, 1H), 7.71 (dd, J = 2.01, 8.53 Hz, 1H), 7.44 (q, J = 5.02 Hz, 1H), 7.37 (d, J = 8.53 Hz, 1H), 7.28 (s, 1H), 3.99 (s, 3H), 4.01 (s, 3H), 3.50-3.60 (m, 4H), 2.96-3.03 (m, 4H), 2.45 (d, J = 4.77 Hz, 3H) |
| 4 | 3-{[6,7-bis(methyloxy)-4-quinazolinyl]amino}-4-[ethyl(methyl)amino]-N-methylbenzenesulfonamide | 1.91$^a$ | 432.2 | $^1$H NMR (400 MHz, DMSO-d$_6$) δ 11.29 (br. s., 1H), 8.80 (s, 1H), 8.29 (s, 1H), 7.62-7.71 (m, 2H), 7.32-7.39 (m, 2H), 7.26 (d, J = 8.53 Hz, 1H), 3.99 (s, 3H), 4.01 (s, 3H), 3.07 (q, J = 6.94 Hz, 2H), 2.79 (s, 3H), 2.43 (d, J = 4.77 Hz, 3H), 0.96 (t, J = 7.03 Hz, 3H) |
| 5 | 3-{[6,7-bis(methyloxy)-4-quinazolinyl]amino}-N-methyl-4-(methyloxy)benzenesulfon-amide | 1.93$^a$ | 433.1 | $^1$H NMR (400 MHz, DMSO-d$_6$) δ 11.09 (br. s., 1H), 8.76 (s, 1H), 8.12 (s, 1H), 7.78-7.85 (m, 2H), 7.40-7.49 (m, 2H), 7.30 (s, 1H), 4.00 (d, J = 7.55 Hz, 6H), 3.89 (s, 3H), 2.45 (d, J = 4.78 Hz, 3H) |
| 6 | 3-{[6,7-bis(methyloxy)-4-quinazolinyl]amino}-N-methyl-4-[(1-methylethyl)oxy]benzene-sulfonamide | 1.75$^a$ | 405 | $^1$H NMR (400 MHz, DMSO-d$_6$) δ 10.93 (br. s., 1H), 8.77 (s, 1H), 8.05 (s, 1H), 7.80-7.85 (m, 1H), 7.76 (dd, J = 2.27, 8.81 Hz, 1H), 7.39-7.49 (m, 2H), 7.29 (s, 1H), 4.78 (quin, J = 5.98 Hz, 1H), 4.01 (s, 3H), 3.99 (s, 3H), 2.45 (d, J = 5.04 Hz, 3H), 1.21 (s, 3H), 1.19 (s, 3H) |
| 7 | 3-{[6,7-bis(methyloxy)-4-quinazolinyl]amino}-N-methyl-4-(methylthio)ben-zenesulfonamide trifluoroacetate | 1.80$^a$ | 421.1 | $^1$H NMR (400 MHz, methanol-d$_4$) δ 7.08 (s, 1H), 6.41 (s, 1H), 6.32-6.37 (m, 1H), 6.30 (d, J = 1.76 Hz, 1H), 6.10 (d, J = 8.53 Hz, 1H), 5.73 (s, 1H), 2.54 (s, 3H), 2.56 (s, 3H), 1.05 (s, 3H), 1.02 (s, 3H) |
| 8 | 4-(dimethylamino)-N-methyl-3-(4-quinazolinylamino)benzene-sulfonamide trifluoroacetate | 1.67$^a$ | 358.1 | $^1$H NMR (400 MHz, DMSO-d$_6$) δ ppm 10.77 (br. s., 1 H), 8.78-8.87 (m, 1 H), 8.75 (s, 1 H), 8.06 (dd, J = 8.91, 1.88 Hz, 1 H), 7.87 (d, J = 9.04 Hz, 1 H), 7.74 (d, J = 2.01 Hz, 1 H), 7.63 (dd, J = 8.78, 2.26 Hz, 1 H), 7.32 (q, J = 5.02 Hz, 1 H), 7.23 (d, J = 8.78 Hz, 1 H), 2.80 (s, 6 H), 2.43 (d, J = 5.02 Hz, 3 H) |
| 9 | 3-[(6-chloro-4-quinazolinyl)amino]-4-(dimethylamino)-N-methylbenzenesulfonamide | 1.89$^a$ | 392.0 | $^1$H NMR (400 MHz, DMSO-d$_6$) δ ppm 11.32 (br. s., 1 H), 8.85 (s, 1 H), 8.19 (d, J = 2.51 Hz, 1 H), 7.87 (d, J = 9.29 Hz, 1 H), 7.77 (dd, J = 9.29, 2.51 Hz, 1 H), 7.72 (d, J = 2.26 Hz, 1 H), 7.67 (dd, J = 8.53, 2.26 Hz, 1 H), 7.33 (q, J = 4.94 Hz, 1 H), 7.25 (d, |

-continued

| Ex. | Name | $t_R$ (min) | MS (m/z) | $^1$H NMR |
|---|---|---|---|---|
| | | | | J = 8.78 Hz, 1 H), 3.97 (s, 3 H), 2.82 (s, 6 H), 2.39-2.47 (m, 3 H) |
| 10 | 4-(dimethylamino)-N-methyl-3-{[6-(methyloxy)-4-quinazolinyl]amino}benzene-sulfonamide trifluoroacetate | 1.89$^a$ | 388.1 | $^1$H NMR (400 MHz, DMSO-d$_6$) δ ppm 9.41 (s, 1 H), 8.36 (s, 1 H), 7.97 (d, J = 2.26 Hz, 1 H), 7.73 (s, 1 H), 7.68 (dd, J = 8.78, 2.26 Hz, 1 H), 7.40-7.50 (m, 2 H), 7.20 (s, 1 H), 4.88 (q, J = 8.78 Hz, 2 H), 3.95 (s, 3 H), 3.94 (s, 3 H), 2.46 (d, J = 4.77 Hz, 3 H) |
| 11 | 3-{[6,7-bis(methyloxy)-4-quinazolinyl]amino}-N-methyl-4-[(2,2,2-trifluoro-ethyl)oxy]benzenesulfonamide hydrochloride | 2.10$^a$ | 473.0 | $^1$H NMR (400 MHz, DMSO-d$_6$) δ ppm 9.91 (br. s., 1 H), 8.57 (br. s., 1 H), 8.49 (s, 1 H), 7.77-7.95 (m, 3 H), 7.67-7.77 (m, 1 H), 7.47 (d, J = 8.28 Hz, 2 H), 4.88 (q, J = 8.70 Hz, 2 H), 2.46 (d, J = 4.77 Hz, 3 H) |
| 12 | 3-[(6-chloro-4-quinazolinyl)amino]-N-methyl-4-[(2,2,2-trifluoroethyl)oxy]benzene-sulfonamide | 2.14$^a$ | 447.0 | $^1$H NMR (400 MHz, DMSO-d$_6$) δ ppm 11.05 (br. s., 1 H), 8.78 (s, 1 H), 8.24 (s, 1 H), 7.69 (d, J = 2.26 Hz, 1 H), 7.63-7.68 (m, 1 H), 7.29-7.35 (m, 2 H), 7.23 (d, J = 8.78 Hz, 1 H), 4.41-4.59 (m, 4 H), 2.80 (s, 6 H), 2.43 (d, J = 5.02 Hz, 3 H) |
| 13 | 3-(7,8-dihydro[1,4]dioxino[2,3-g]quinazolin-4-ylamino)-4-(dimethylamino)-N-methylbenzenesulfonamide bis(trifluoroacetate) | 1.87$^a$ | 416.1 | $^1$H NMR (400 MHz, DMSO-d$_6$) δ ppm 10.63 (br. s., 1 H), 8.77 (s, 1 H), 8.07 (s, 1 H), 7.97 (d, J = 2.01 Hz, 1 H), 7.69 (dd, J = 8.53, 2.01 Hz, 1 H), 7.38-7.51 (m, 2 H), 7.30 (s, 1 H), 4.02 (s, 3 H), 3.98 (s, 3 H), 3.12 (t, J = 5.14 Hz, 4 H), 2.45 (d, J = 5.02 Hz, 3 H), 1.87-2.05 (m, 4 H) |
| 14 | 3-{[6,7-bis(methyloxy)-4-quinazolinyl]amino}-4-(4,4-difluoro-1-piperidinyl)-N-methylbenzenesulfonamide trifluoroacetate | 2.14$^a$ | 494.1 | $^1$H NMR (400 MHz, DMSO-d$_6$) δ ppm 10.57 (br. s., 1 H), 8.67-8.86 (m, 2 H), 8.06 (dd, J = 8.91, 2.13 Hz, 1 H), 7.93-8.01 (m, 1 H), 7.89 (d, J = 9.04 Hz, 1 H), 7.67 (dd, J = 8.53, 2.26 Hz, 1 H), 7.36-7.49 (m, 2 H), 3.12 (t, J = 5.27 Hz, 4 H), 2.46 (d, J = 4.77 Hz, 3 H), 1.89-2.03 (m, 4 H) |
| 15 | 3-[(6-chloro-4-quinazolinyl)amino]-4-(4,4-difluoro-1-piperidinyl)-N-methylbenzenesulfonamide trifluoroacetate | 2.24$^a$ | 468.0 | $^1$H NMR (400 MHz, DMSO-d$_6$) δ ppm 9.45 (br. s., 1 H), 8.44 (s, 1 H), 8.38 (d, J = 9.03 Hz, 1 H), 7.88-7.95 (m, 1 H), 7.54 (dd, J = 8.53, 2.01 Hz, 1 H), 7.13-7.36 (m, 4 H), 4.28 (t, J = 6.02 Hz, 2 H), 3.85 (t, J = 6.53 Hz, 2 H), 2.77 (s, 6 H), 2.43 (s, 3 H), 2.26 (quin, J = 6.21 Hz, 2 H) |
| 16 | 3-({7-[(3-chloropropyl)oxy]-4-quinazolinyl}amino)-4-(dimethylamino)-N-methylbenzenesulfonamide | 2.15$^a$ | 450.1 | $^1$H NMR (400 MHz, DMSO-d$_6$) δ ppm 9.95 (br. s., 1 H), 8.76 (br. s., 1 H), 8.60 (d, J = 9.29 Hz, 1 H), 7.76 (d, J = 2.01 Hz, 1 H), 7.64 (dd, J = 8.66, 2.13 Hz, 1 H), 7.44 (d, J = 8.78 Hz, 1 H), 7.33 (q, J = 5.19 Hz, 1 H), 7.20-7.29 (m, 2 H), 4.30 (t, J = 5.77 Hz, 2 H), 4.01 (br. s., 2 H), 3.68 (t, J = 12.55 Hz, 2 H), 3.57 (s, 3 H), 3.52 (br. s., 2 H), 3.34 (br. s., 2 H), 3.14 (br. s., 2 H), 2.80 (s, 6 H), 2.40-2.46 (m, 3 H), 2.23 (d, J = 9.03 Hz, 2 H) |
| 17 | 3-[(6,7-bis{[2-(methyloxy)ethyl]oxy}-4-quinazolinyl)amino]-4-(dimethylamino)-N-methylbenzenesulfonamide trifluoroacetate | 1.96$^a$ | 506.2 | $^1$H NMR (400 MHz, DMSO-d$_6$) δ ppm 11.12 (br. s., 1 H), 8.75 (s, 1 H), 8.19 (s, 1 H), 7.78-7.84 (m, 2 H), 7.41-7.49 (m, 2 H), 7.36 (s, 1 H), 4.35 (q, J = 4.85 Hz, 4 H), 3.89 (s, 3 H), 3.76-3.83 (m, 4 H), 3.37 (s, 3 H), 3.37 (s, 3 H), 2.46 (d, J = 5.02 Hz, 3 H) |
| 18 | 3-[(6,7-bis{[2-(methyloxy)ethyl]oxy}-4-quinazolinyl)amino]-N-methyl-4-(methyloxy)benzene-sulfonamide hydrochloride | 1.90$^a$ | 493.1 | $^1$H NMR (400 MHz, DMSO-d$_6$) δ ppm 9.39 (br. s., 1 H), 8.35 (s, 1 H), 7.96 (d, J = 2.01 Hz, 1 H), 7.77 (s, 1 H), 7.68 (dd, J = 8.53, 2.26 Hz, 1 H), 7.39-7.51 (m, 2 H), 7.23 (s, 1 H), 4.88 (q, J = 8.70 Hz, 2 H), 4.22-4.32 (m, 4 H), 3.70-3.82 (m, 4 H), 3.37 (s, 3 H), 3.36 (s, 3 H), 2.46 (s, 3 H) |
| 19 | 3-[(6,7-bis{[2-(methyloxy)ethyl]oxy}-4-quinazolinyl)amino]-N-methyl-4-[(2,2,2-trifluoro-ethyl)oxy]benzenesulfonamide | 2.08$^a$ | 561.1 | $^1$H NMR (400 MHz, DMSO-d$_6$) δ ppm 9.58 (br. s., 1 H), 8.29 (s, 1 H), 7.85 (s, 1 H), 7.62-7.74 (m, 2 H), 7.56 (d, J = 8.28 Hz, 1 H), 7.42-7.51 (m, 1 H), 7.22 (s, 1 H), 4.22-4.33 (m, 4 H), 3.71-3.81 (m, 4 H), 3.38 (s, 3 H), 3.36 (s, 3 H), 2.46 (s, 6 H) |
| 20 | 3-[(6,7-bis{[2-(methyloxy)ethyl]oxy}-4-quinazolinyl)amino]-N-methyl-4-(methylthio)benzene-sulfonamide | 1.97$^a$ | 509.1 | $^1$H NMR (400 MHz, DMSO-d$_6$) δ ppm 11.06 (br. s., 1 H), 8.74 (s, 1 H), 8.06 (s, 1 H), 7.69 (d, J = 2.01 Hz, 1 H), 7.64 (dd, J = 8.78, 2.26 Hz, 1 H), 7.54 (d, J = 9.03 Hz, 1 H), 7.36 (q, J = 4.94 Hz, 1 H), 7.31 (s, 1 H), 4.91-5.04 (m, 1 H), 4.01 (s, 3 H), 3.98 (s, 3 H), 3.32-3.43 (m, 1 H), 3.15- |

-continued

| Ex. | Name | $t_R$ (min) | MS (m/z) | $^1$H NMR |
|---|---|---|---|---|
| | | | | 3.24 (m, 1 H), 2.44 (d, J = 5.02 Hz, 3 H), 2.10-2.23 (m, 1 H), 1.70-1.94 (m, 3 H) |
| 21 | 3-{[6,7-bis(methyloxy)-4-quinazolinyl]amino}-N-methyl-4-[(2R)-2-(trifluoromethyl)-1-pyrrolidinyl]benzenesulfonamide trifluoroacetate | 2.14$^a$ | 512.1 | $^1$H NMR (400 MHz, DMSO-d$_6$) δ ppm 10.85 (br. s., 1 H), 8.73 (br. s., 2 H), 8.01-8.10 (m, 1 H), 7.87 (d, J = 9.03 Hz, 1 H), 7.71 (br. s., 1 H), 7.60 (dd, J = 8.78, 2.01 Hz, 1 H), 7.52 (d, J = 8.78 Hz, 1 H), 7.33 (q, J = 4.94 Hz, 1 H), 4.96 (br. s., 1 H), 3.36-3.47 (m, 1 H), 3.14-3.25 (m, 1 H), 2.44 (d, J = 5.02 Hz, 3 H), 2.09-2.23 (m, 1 H), 1.68-1.95 (m, 3H) |
| 22 | 3-[(6-chloro-4-quinazolinyl)amino]-N-methyl-4-[(2R)-2-(trifluoromethyl)-1-pyrrolidinyl]benzenesulfonamide trifluoroacetate | 2.25$^a$ | 486.0 | $^1$H NMR (400 MHz, DMSO-d$_6$) δ ppm 11.53 (br. s., 1 H), 8.89 (s, 1 H), 8.34 (s, 1 H), 8.06-8.21 (m, 2 H), 7.89 (q, J = 4.77 Hz, 1 H), 7.61 (t, J = 9.29 Hz, 1 H), 7.37 (s, 1 H), 4.04 (s, 3 H), 4.01 (s, 3 H), 2.57 (d, J = 4.77 Hz, 3 H) |
| 23 | 5-{[6,7-bis(methyloxy)-4-quinazolinyl]amino}-2-fluoro-N-methylbenzenesulfonamide hydrochloride | 1.85$^a$ | 393.1 | $^1$H NMR (400 MHz, DMSO-d$_6$) δ ppm 10.86 (br. s., 1 H), 8.72 (s, 1 H), 8.05 (d, J = 2.01 Hz, 1 H), 7.98 (s, 1 H), 7.89 (dd, J = 8.66, 2.13 Hz, 1 H), 7.79-7.86 (m, 1 H), 7.73 (q, J = 5.10 Hz, 1 H), 7.29 (s, 1 H), 4.00-4.04 (m, 3 H), 3.97-4.00 (m, 3 H), 2.5 (d, 3H, obscured by DMSO) |
| 24 | 3-{[6,7-bis(methyloxy)-4-quinazolinyl]amino}-N-methyl-4-[(trifluoromethyl)oxy]benzenesulfonamide trifluoroacetate | 2.05$^a$ | 459.1 | $^1$H NMR (400 MHz, DMSO-d$_6$) δ ppm 10.72 (br. s., 1 H), 8.79 (s, 1 H), 8.09 (s, 1 H), 7.92 (d, J = 1.76 Hz, 1 H), 7.69 (dd, J = 8.53, 2.26 Hz, 1 H), 7.41 (q, J = 5.19 Hz, 1 H), 7.34 (d, J = 8.78 Hz, 1 H), 7.29 (s, 1 H), 4.02 (s, 3 H), 3.98 (s, 3 H), 2.95 (br. s., 4 H), 2.45 (d, J = 5.02 Hz, 3 H), 1.46 (br. s., 6 H) |
| 25 | 3-{[6,7-bis(methyloxy)-4-quinazolinyl]amino}-N-methyl-4-(1-piperidinyl)benzenesulfonamide trifluoroacetate | 2.16$^a$ | 458.1 | $^1$H NMR (400 MHz, DMSO-d$_6$) δ ppm 10.68 (br. s., 1 H), 8.78 (s, 2 H), 8.07 (dd, J = 8.91, 2.13 Hz, 1 H), 7.95 (d, J = 2.01 Hz, 1 H), 7.89 (d, J = 9.03 Hz, 1 H), 7.67 (dd, J = 8.41, 2.13 Hz, 1 H), 7.40 (q, J = 4.94 Hz, 1 H), 7.33 (d, J = 8.53 Hz, 1 H), 2.95 (br. s., 4 H), 2.45 (d, J = 5.02 Hz, 3 H), 1.47 (br. s., 6 H) |
| 26 | 3-[(6-chloro-4-quinazolinyl)amino]-N-methyl-4-(1-piperidinyl)benzenesulfonamide trifluoroacetate | 2.30$^a$ | 432.1 | $^1$H NMR (500 MHz, DMSO-d$_6$) δ ppm 10.97 (br. s., 1 H), 8.83 (s, 1 H), 7.97 (br. s., 1 H), 7.72 (br. s., 1 H), 7.59 (dd, J = 9.03, 2.20 Hz, 1 H), 7.28 (s, 1 H), 7.18-7.26 (m, 1 H), 7.15 (d, J = 9.03 Hz, 1 H), 4.01 (s, 3 H), 3.96 (s, 3 H), 3.77-3.84 (m, 2 H), 2.40 (d, J = 4.88 Hz, 3 H), 1.88-2.01 (m, 2 H), 1.56-1.67 (m, 2 H), 1.12 (d, J = 6.10 Hz, 6 H) |
| 27 | 3-{[6,7-bis(methyloxy)-4-quinazolinyl]amino}-4-(2,5-dimethyl-1-pyrrolidinyl)-N-methylbenzenesulfonamide trifluoroacetate | 2.21$^a$ | 472.1 | $^1$H NMR (400 MHz, DMSO-d$_6$) δ ppm 10.96 (br. s., 1 H), 8.83 (s, 1 H), 8.64 (s, 1 H), 8.09 (dd, J = 8.91, 2.13 Hz, 1 H), 7.89 (d, J = 9.03 Hz, 1 H), 7.80 (d, J = 2.01 Hz, 1 H), 7.58 (dd, J = 8.91, 2.38 Hz, 1 H), 7.24 (d, J = 4.77 Hz, 1 H), 7.18 (d, J = 9.03 Hz, 1 H), 3.82 (br. s., 2 H), 2.42 (d, J = 4.77 Hz, 3 H), 1.89-2.03 (m, 2 H), 1.57-1.69 (m, 2 H), 1.12 (d, 6 H) |
| 28 | 3-[(6-chloro-4-quinazolinyl)amino]-4-(2,5-dimethyl-1-pyrrolidinyl)-N-methylbenzenesulfonamide trifluoroacetate | 2.38$^a$ | 446.1 | $^1$H NMR (400 MHz, DMSO-d$_6$) δ ppm 10.83 (br. s., 1 H), 8.61 (br. s., 1 H), 8.03 (s, 1 H), 7.96 (d, J = 8.03 Hz, 1 H), 7.72-7.80 (m, 2 H), 7.61 (q, J = 4.94 Hz, 1 H), 7.29 (s, 1 H), 4.14 (q, J = 10.21 Hz, 2 H), 3.99 (s, 3 H), 3.99 (s, 3 H), 2.47 (d, J = 5.02 Hz, 3 H) |
| 29 | 3-{[6,7-bis(methyloxy)-4-quinazolinyl]amino}-N-methyl-4-[(2,2,2-trifluoroethyl)thio]benzenesulfonamide hydrochloride | 2.08$^a$ | 489.0 | $^1$H NMR (400 MHz, DMSO-d$_6$) δ ppm 9.97 (s, 1 H), 8.48 (s, 1 H), 8.39 (t, J = 1.76 Hz, 1 H), 7.94-8.00 (m, 1 H), 7.55-7.65 (m, 1 H), 7.45-7.55 (m, 2 H), 6.83 (d, J = 2.26 Hz, 1 H), 6.75 (d, J = 2.26 Hz, 1 H), 4.10 (s, 3 H), 3.92 (s, 3 H), 2.44-2.49 (m, 3 H) |
| 30 | 3-{[5,7-bis(methyloxy)-4-quinazolinyl]amino}-N-methylbenzenesulfonamide hydrochloride | 1.86$^a$ | 375.1 | $^1$H NMR (400 MHz, DMSO-d$_6$) δ ppm 10.79 (s, 1 H), 8.83 (s, 1 H), 8.60 (br. s., 1 H), 7.73 (dd, J = 8.66, 2.13 Hz, 1 H), 7.48-7.60 (m, 2 H), 6.98 (d, J = 2.26 Hz, 1 H), 6.92 (d, J = 2.26 Hz, 1 H), 5.08 (q, J = 8.78 |

-continued

| Ex. | Name | $t_R$ (min) | MS (m/z) | $^1$H NMR |
|---|---|---|---|---|
| | | | | Hz, 2 H), 4.14 (s, 3 H), 3.99 (s, 3 H), 2.47 (d, J = 5.02 Hz, 3 H) |
| 31 | 3-{[5,7-bis(methyloxy)-4-quinazolinyl]amino}-N-methyl-4-[(2,2,2-trifluoroethyl)oxy]benzenesulfonamide hydrochloride | 2.08$^a$ | 473 | $^1$H NMR (400 MHz, DMSO-d$_6$) δ ppm 10.92 (s, 1 H), 9.30 (d, J = 2.01 Hz, 1 H), 8.57 (s, 1 H), 7.42-7.49 (m, 2 H), 7.40 (q, J = 5.02 Hz, 1 H), 6.85 (d, J = 2.26 Hz, 1 H), 6.79 (d, J = 2.26 Hz, 1 H), 4.08-4.13 (m, 3 H), 3.93 (s, 3 H), 2.77 (s, 6 H), 2.46 (d, J = 5.02 Hz, 3 H) |
| 32 | 3-{[5,7-bis(methyloxy)-4-quinazolinyl]amino}-4-(dimethylamino)-N-methylbenzenesulfonamide | 2.01$^a$ | 418.1 | $^1$H NMR (400 MHz, DMSO-d$_6$) δ ppm 9.87 (br. s., 1 H), 8.57 (s, 1 H), 8.17 (s, 1 H), 7.92 (d, J = 8.82 Hz, 1 H), 7.57-7.64 (m, 1 H), 7.48-7.56 (m, 2 H), 7.34 (s, 1 H), 4.01 (s, 3 H), 3.85 (s, 3 H), 2.45 (d, J = 4.85 Hz, 3 H) |
| 33 | 3-(5-chloro-6,7-dimethoxyquinazolin-4-ylamino)-N-methylbenzenesulfonamide trifluoroacetate | 0.97$^b$ | 409.0 | $^1$H NMR (400 MHz, DMSO-d$_6$) δ ppm 10.87 (br. s., 1 H), 10.24 (br. s., 1 H), 8.70 (s, 1 H), 8.10 (br. s., 1 H), 7.73-7.84 (m, 2 H), 7.35-7.48 (m, 2 H), 7.32 (d, J = 2.21 Hz, 1 H), 4.25 (t, J = 5.51 Hz, 2 H), 3.93-4.04 (m, 5 H), 3.85 (s, 3 H), 3.65-3.74 (m, 2 H), 3.48 (d, J = 6.62 Hz, 2 H), 3.30 (br. s., 2 H), 3.11 (br. s., 2 H), 2.42 (d, J = 4.85 Hz, 3 H), 2.23-2.34 (m, 2 H) |
| 34 | 4-methoxy-3-(7-methoxy-6-(3-morpholinopropoxy)quinazolin-4-ylamino)-N-methylbenzenesulfonamide bis(trifluoroacetate) | 0.86$^b$ | 518.1 | $^1$H NMR (400 MHz, DMSO-d$_6$) δ ppm 10.93 (br. s., 1 H), 8.78 (s, 1 H), 8.05 (s, 1 H), 7.78 (d, J = 2.01 Hz, 1 H), 7.72 (dd, J = 8.66, 2.13 Hz, 1 H), 7.51 (d, J = 8.78 Hz, 1 H), 7.44 (q, J = 5.02 Hz, 1 H), 7.28 (s, 1 H), 4.02 (s, 3 H), 3.93 (s, 3 H), 3.88-3.97 (m, 2 H), 2.96 (s, 3 H), 2.44 (d, J = 5.02 Hz, 3 H) |
| 35 | 3-{[6,7-bis(methyloxy)-4-quinazolinyl]amino}-N-methyl-4-[methyl (2,2,2-trifluoroethyl)amino]benzenesulfonamide trifluoroacetate | 1.94$^a$ | 486.1 | $^1$H NMR (400 MHz, DMSO-d$_6$) δ ppm 11.02-11.20 (m, 1 H), 8.85 (s, 1 H), 8.79 (br. s., 1 H), 7.61-7.77 (m, 2 H), 7.52 (q, J = 5.02 Hz, 1 H), 6.98 (d, J = 1.76 Hz, 1 H), 6.88 (d, J = 2.26 Hz, 1 H), 4.16 (s, 3 H), 4.07 (q, J = 9.54 Hz, 2 H), 3.99 (s, 3 H), 2.92 (s, 3 H), 2.48 (d, J = 5.02 Hz, 3 H) |
| 36 | 3-{[5,7-bis(methyloxy)-4-quinazolinyl]amino}-N-methyl-4-[methyl (2,2,2-trifluoroethyl)amino]benzenesulfonamide hydrochloride | 2.05$^a$ | 486.1 | $^1$H NMR (400 MHz, DMSO-d$_6$) δ ppm 11.09 (s, 1 H), 8.88 (s, 1 H), 8.78 (br. s., 1 H), 7.69 (dd, J = 8.66, 2.13 Hz, 1 H), 7.47 (q, J = 4.94 Hz, 1 H), 7.41 (d, J = 8.78 Hz, 1 H), 6.98 (d, J = 1.76 Hz, 1 H), 6.91 (d, J = 2.01 Hz, 1 H), 4.18 (s, 3 H), 4.04 (s, 3 H), 3.99 (s, 3 H), 2.45 (d, J = 5.02 Hz, 3 H) |
| 37 | 3-{[5,7-bis(methyloxy)-4-quinazolinyl]amino}-N-methyl-4-(methyloxy)benzenesulfonamide hydrochloride | 1.86$^a$ | 405.1 | $^1$H NMR (400 MHz, DMSO-d$_6$) δ ppm 10.73 (s, 1 H), 8.78 (s, 1 H), 8.21 (br. s., 1 H), 7.78-7.87 (m, 1 H), 7.62-7.73 (m, 2 H), 6.96 (d, J = 2.26 Hz, 1 H), 6.90 (d, J = 2.26 Hz, 1 H), 4.13 (s, 3 H), 3.99 (s, 3 H), 2.49 (d, J = 5.02 Hz, 3 H) |
| 38 | 3-{[5,7-bis(methyloxy)-4-quinazolinyl]amino}-4-fluoro-N-methylbenzenesulfonamide hydrochloride | 1.84$^a$ | 393.0 | $^1$H NMR (400 MHz, DMSO-d$_6$) δ ppm 10.92 (s, 1 H), 8.79 (s, 1 H), 8.41 (br. s., 1 H), 7.92 (d, J = 8.28 Hz, 1 H), 7.70-7.77 (m, 2 H), 6.97 (d, J = 2.26 Hz, 1 H), 6.92 (d, J = 2.26 Hz, 1 H), 4.16 (s, 3 H), 3.99 (s, 3 H), 2.49 (s, 3 H) |
| 39 | 3-{[5,7-bis(methyloxy)-4-quinazolinyl]amino}-4-chloro-N-methylbenzenesulfonamide hydrochloride | 1.92$^a$ | 409.0 | $^1$H NMR (400 MHz, DMSO-d$_6$) δ ppm 10.81 (br. s., 1 H), 8.85 (s, 1 H), 8.52 (s, 1 H), 7.67 (dd, J = 8.41, 2.13 Hz, 1 H), 7.44-7.53 (m, 2 H), 7.00 (d, J = 2.01 Hz, 1 H), 6.92 (d, J = 2.01 Hz, 1 H), 4.23 (s, 3 H), 4.00 (s, 3 H), 3.67-3.75 (m, 4 H), 2.95-3.02 (m, 4 H), 2.46 (d, J = 5.02 Hz, 3 H) |
| 40 | 3-{[5,7-bis(methyloxy)-4-quinazolinyl]amino}-N-methyl-4-(4-morpholinyl)benzenesulfonamide hydrochloride | 1.84$^a$ | 460.1 | $^1$H NMR (400 MHz, DMSO-d$_6$) δ ppm 11.07 (br. s., 1 H), 8.76 (s, 1 H), 8.13 (s, 1 H), 7.78 (d, J = 7.78 Hz, 1 H), 7.74 (q, J = 4.77 Hz, 1 H), 7.43 (d, J = 12.05 Hz, 1 H), 7.31 (s, 1 H), 4.01 (s, 3 H), 3.99 (s, 3 H), 3.90 (s, 3 H), 2.53 (d, J = 5.27 Hz, 3 H) |
| 41 | 5-{[6,7-bis(methyloxy)-4-quinazolinyl]amino}-2-fluoro-N-methyl-4-(methyloxy)benzenesulfonamide hydrochloride | 1.72$^a$ | 423.0 | $^1$H NMR (400 MHz, DMSO-d$_6$) δ ppm 11.19 (br. s., 1 H), 8.76 (s, 1 H), 8.10 (s, 1 H), 7.79-7.91 (m, 2 H), 7.50-7.59 (m, 2 H), 7.34 (s, 1 H), 4.93 (q, J = 8.78 Hz, 2 H), 4.26 (q, J = 6.86 Hz, 2 H), 4.02 (s, 3 H), |

-continued

| Ex. | Name | $t_R$ (min) | MS (m/z) | $^1$H NMR |
|---|---|---|---|---|
| 42 | 3-{[6-(ethyloxy)-7-(methyloxy)-4-quinazolinyl]amino}-N-methyl-4-[(2,2,2-trifluoroethyl)oxy]benzene-sulfonamide hydrochloride | 1.97$^a$ | 487.1 | 2.47 (d, J = 5.02 Hz, 3 H), 1.46 (t, J = 7.03 Hz, 3 H) $^1$H NMR (400 MHz, METHANOL-d$_4$) δ ppm 8.44 (br. s., 2 H), 8.38 (s, 1 H), 8.12 (d, J = 2.21 Hz, 1 H), 7.69 (s, 1 H), 7.63 (dd, J = 8.38, 2.21 Hz, 1 H), 7.27 (d, J = 8.38 Hz, 1 H), 7.20 (s, 1 H), 4.27 (t, J = 5.73 Hz, 2 H), 4.01 (s, 3 H), 3.77 (t, J = 4.63 Hz, 4 H), 2.79-2.85 (m, 8 H), 2.74 (br. s., 4 H), 2.57 (s, 3 H), 2.13-2.22 (m, 2 H) |
| 43 | 4-(dimethylamino)-3-(7-methoxy-6-(3-morpholinopropoxy)quinazolin-4-ylamino)-N-methylbenzenesulfonamide bis(formate) | 0.89$^b$ | 531.2 | $^1$H NMR (400 MHz, DMSO-d$_6$) δ ppm 11.27 (br. s., 1 H), 8.77 (s, 1 H), 8.15 (s, 1 H), 7.88 (d, J = 2.26 Hz, 1 H), 7.84 (dd, J = 8.66, 2.38 Hz, 1 H), 7.53-7.59 (m, 2 H), 7.35 (s, 1 H), 4.84-5.00 (m, 3 H), 4.01 (s, 3 H), 2.47 (d, J = 5.02 Hz, 3 H), 1.40 (d, J = 6.02 Hz, 6 H) |
| 44 | N-methyl-3-{[6-[(1-methylethyl)oxy]-7-(methyloxy)-4-quinazolinyl]amino}-4-[(2,2,2-trifluoroethyl)oxy]benzene-sulfonamide hydrochloride | 2.04$^a$ | 501.1 | $^1$H NMR (400 MHz, DMSO-d$_6$) δ ppm 9.58 (s, 1 H), 8.19-8.38 (m, 2 H), 7.95 (br. s., 1 H), 7.56 (br. s., 1 H), 7.37 (br. s., 2 H), 7.11 (br. s., 2 H), 4.86 (q, J = 8.95 Hz, 2 H), 4.26 (t, J = 5.77 Hz, 2 H), 3.85 (t, J = 6.53 Hz, 2 H), 2.45 (s, 3 H), 2.25 (quin, J = 6.27 Hz, 2 H) |
| 45 | 3-({7-[(3-chloropropyl)oxy]-4-quinazolinyl}amino)-N-methyl-4-[(2,2,2-trifluoroethyl)oxy]benzene-sulfonamide | 2.09$^a$ | 505.0 | $^1$H NMR (400 MHz, DMSO-d$_6$) δ ppm 10.18 (s, 1 H), 9.14 (d, J = 2.01 Hz, 1 H), 8.53 (s, 1 H), 7.48-7.56 (m, 2 H), 7.45 (q, J = 4.85 Hz, 1 H), 6.86 (d, J = 2.26 Hz, 1 H), 6.80 (d, J = 2.51 Hz, 1 H), 5.12 (q, J = 8.95 Hz, 2 H), 4.44 (q, J = 6.94 Hz, 2 H), 3.92 (s, 3 H), 2.47 (d, J = 5.02 Hz, 3 H), 1.46 (t, J = 6.90 Hz, 3 H) |
| 46 | 3-{[5-(ethyloxy)-7-(methyloxy)-4-quinazolinyl]amino}-N-methyl-4-[(2,2,2-trifluoroethyl)oxy]benzene-sulfonamide | 2.08$^a$ | 487.0 | $^1$H NMR (400 MHz, DMSO-d$_6$) δ ppm 10.00 (s, 1 H), 8.91 (s, 1 H), 8.48 (s, 1 H), 7.51-7.59 (m, 2 H), 7.44 (q, J = 5.02 Hz, 1 H), 6.84 (d, J = 2.26 Hz, 1 H), 6.81 (d, J = 2.26 Hz, 1 H), 5.10 (q, J = 8.87 Hz, 2 H), 5.00 (dt, J = 12.17, 5.96 Hz, 1 H), 3.92 (s, 3 H), 2.48 (d, J = 5.02 Hz, 3 H), 1.44 (d, J = 6.02 Hz, 6 H) |
| 47 | N-methyl-3-{[5-[(1-methylethyl)oxy]-7-(methyloxy)-4-quinazolinyl]amino}-4-[(2,2,2-trifluoro-ethyl)oxy]benzenesulfonamide | 2.13$^a$ | 501.1 | $^1$H NMR (400 MHz, DMSO-d$_6$) δ ppm 9.59 (s, 1 H), 8.40 (s, 1 H), 8.30 (d, J = 9.03 Hz, 1 H), 7.94 (d, J = 2.26 Hz, 1 H), 7.69 (dd, J = 8.78, 2.26 Hz, 1 H), 7.45 (d, J = 8.78 Hz, 2 H), 7.26 (dd, J = 9.16, 2.38 Hz, 1 H), 7.17 (d, J = 2.51 Hz, 1 H), 4.88 (q, J = 8.78 Hz, 2 H), 4.21 (t, J = 6.27 Hz, 2 H), 3.52 (t, J = 6.27 Hz, 2 H), 3.28 (s, 3 H), 2.46 (d, J = 4.52 Hz, 3 H), 2.03 (quin, J = 6.34 Hz, 2 H) |
| 48 | N-methyl-4-[(2,2,2-trifluoroethyl)oxy]-3-{[5,6,7-tris(methyloxy)-4-quinazolinyl]amino}benzene-sulfonamide hydrochloride | 2.23$^a$ | 503.1 | $^1$H NMR (500 MHz, DMSO-d$_6$) δ ppm 10.59 (br. s., 1 H), 8.75 (s, 2 H), 7.63-7.70 (m, 1 H), 7.52-7.63 (m, 1 H), 7.47 (q, J = 4.64 Hz, 1 H), 6.93 (s, 1 H), 6.86 (d, J = 1.95 Hz, 1 H), 5.49-5.68 (m, 1 H), 4.12 (s, 3 H), 3.97 (s, 3 H), 2.47 (d, J = 4.88 Hz, 3 H), 1.52 (d, J = 6.35 Hz, 3 H) |
| 49 | 3-{[5,7-bis(methyloxy)-4-quinazolinyl]amino}-N-methyl-4-[(2,2,2-trifluoro-1-methylethyl)oxy]benzene-sulfonamide trifluoroacetate | 2.08$^a$ | 487.0 | $^1$H NMR (400 MHz, DMSO-d$_6$) δ ppm 11.14 (s, 1 H), 8.76 (s, 1 H), 8.6 (s, 1 H), 8.21 (d, J = 8.28 Hz, 1 H), 7.83-7.93 (m, 2 H), 6.94 (d, J = 2.01 Hz, 1 H), 6.90 (d, J = 2.01 Hz, 1 H), 4.11 (s, 3 H), 3.99 (s, 3 H), 3.35 (s, 3 H), 2.54 (d, J = 4.77 Hz, 3 H) |
| 50 | 5-{[5,7-bis(methyloxy)-4-quinazolinyl]amino}-2-fluoro-N-methyl-4-[(2,2,2-trifluoroethyl)oxy]benzene-sulfonamide trifluoroacetate | 2.03$^a$ | 491.1 | $^1$H NMR (400 MHz, DMSO-d$_6$) δ ppm 10.81 (br. s., 1 H), 8.77 (s, 2 H), 7.65-7.74 (m, 1 H), 7.39 (d, J = 11.80 Hz, 1 H), 6.92 (d, J = 2.01 Hz, 1 H), 6.83 (d, J = 2.26 Hz, 1 H), 4.15 (s, 3 H), 4.04 (s, 3 H), 3.97 (s, 3 H), 2.52 (br. s., 3 H) |
| 51 | 5-{[5,7-bis(methyloxy)-4-quinazolinyl]amino}-2-fluoro-N-methyl-4-(methyloxy)benzene-sulfonamide trifluoroacetate | 1.89$^a$ | 423.1 | $^1$H NMR (400 MHz, DMSO-d$_6$) δ ppm 11.23 (br. s., 1 H), 8.78 (s, 1 H), 8.12 (s, 1 H), 7.81-7.88 (m, 2 H), 7.61 (d, J = 11.80 Hz, 1 H), 7.33 (s, 1 H), 4.96 (q, J = 8.78 Hz, 2 H), 4.02 (s, 3 H), 4.00 (s, 3 H), 2.54 (d, J = 4.77 Hz, 3 H) |
| 52 | 5-{[6,7-bis(methyloxy)-4-quinazolinyl]amino}-2-fluoro- | 1.90$^a$ | 491.0 | $^1$H NMR (400 MHz, DMSO-d$_6$) δ ppm 10.80 (s, 1 H), 8.74 (s, 1 H), 7.91 (d, |

| Ex. | Name | $t_R$ (min) | MS (m/z) | $^1$H NMR |
|---|---|---|---|---|
| | N-methyl-4-[(2,2,2-trifluoroethyl)oxy]benzenesulfonamide hydrochloride | | | J = 1.51 Hz, 1 H), 7.77 (dd, J = 8.41, 1.88 Hz, 1 H), 7.57-7.66 (m, 2 H), 6.94-6.98 (m, 2 H), 4.14 (s, 3 H), 3.99 (s, 3 H), 2.54 (s, 3 H), 2.47 (d, J = 5.02 Hz, 3 H) |
| 53 | 3-{[5,7-bis(methyloxy)-4-quinazolinyl]amino}-N-methyl-4-(methylthio)benzenesulfonamide hydrochloride | 1.92$^a$ | 421.0 | $^1$H NMR (400 MHz, DMSO-d$_6$) δ ppm 10.84 (s, 1 H), 8.84 (s, 1 H), 8.37-8.44 (m, 1 H), 7.86-7.91 (m, 1 H), 7.79-7.86 (m, 2 H), 6.98-7.03 (m, 2 H), 4.14 (s, 3 H), 3.99 (s, 3 H), 2.49-2.53 (m, 3 H) |
| 54 | 3-{[5,7-bis(methyloxy)-4-quinazolinyl]amino}-N-methyl-4-[(trifluoromethyl)oxy]benzenesulfonamide hydrochloride | 2.06$^a$ | 459.0 | $^1$H NMR (400 MHz, DMSO-d$_6$) δ ppm 10.75 (br. s., 1 H), 8.92 (br. s., 1 H), 8.76 (s, 1 H), 7.68-7.88 (m, 3 H), 7.17 (s, 1 H), 4.18 (s, 3 H), 4.03 (s, 3 H), 3.91 (s, 3 H), 2.53 (br. s., 3 H) |
| 55 | N-methyl-4-[(trifluoromethyl)oxy]-3-{[5,6,7-tris(methyloxy)-4-quinazolinyl]amino}benzenesulfonamide trifluoroacetate | 2.14$^a$ | 489.0 | $^1$H NMR (400 MHz, DMSO-d$_6$) δ ppm 10.95 (s, 1 H), 8.83 (s, 1 H), 8.20 (d, J = 7.78 Hz, 1 H), 7.63 (q, J = 4.77 Hz, 1 H), 7.17 (d, J = 12.55 Hz, 1 H), 6.97 (d, J = 2.01 Hz, 1 H), 6.91 (d, J = 2.26 Hz, 1 H), 4.14 (s, 3 H), 3.98 (s, 3 H), 2.85 (s, 6 H), 2.50 (br. s., 3 H) |
| 56 | 5-{[5,7-bis(methyloxy)-4-quinazolinyl]amino}-4-(dimethylamino)-2-fluoro-N-methylbenzenesulfonamide hydrochloride | 1.93$^a$ | 436.0 | $^1$H NMR (400 MHz, DMSO-d$_6$) δ ppm 11.21 (br. s., 1 H), 8.79 (s, 1 H), 8.22 (s, 1 H), 7.50-7.63 (m, 2 H), 7.32 (s, 1 H), 7.00 (d, J = 13.30 Hz, 1 H), 4.01 (s, 3 H), 3.99 (s, 3 H), 2.85 (s, 6 H), 2.49 (d, J = 4.77 Hz, 3 H) |
| 57 | 5-{[6,7-bis(methyloxy)-4-quinazolinyl]amino}-4-(dimethylamino)-2-fluoro-N-methylbenzenesulfonamide hydrochloride | 1.78$^a$ | 436.1 | $^1$H NMR (400 MHz, DMSO-d$_6$) δ ppm 10.69 (s, 1 H), 8.97 (br. s., 1 H), 8.75 (s, 1 H), 7.77 (q, J = 4.77 Hz, 1 H), 7.58 (d, J = 11.54 Hz, 1 H), 7.13 (s, 1 H), 5.12 (q, J = 8.70 Hz, 2 H), 4.13 (s, 3 H), 4.02 (s, 3 H), 3.90 (s, 3 H), 2.54 (d, J = 4.77 Hz, 3 H) |
| 58 | 2-fluoro-N-methyl-4-[(2,2,2-trifluoroethyl)oxy]-5-{[5,6,7-tris(methyloxy)-4-quinazolinyl]amino}benzenesulfonamide trifluoroacetate | 2.09$^a$ | 521.1 | $^1$H NMR (400 MHz, DMSO-d$_6$) δ ppm 10.76 (s, 1 H), 9.03 (br. s., 1 H), 8.69 (s, 1 H), 7.87 (d, J = 8.28 Hz, 1 H), 7.64-7.72 (m, 1 H), 7.60 (dd, J = 8.28, 1.76 Hz, 1 H), 7.15 (s, 1 H), 4.21 (s, 3 H), 4.02 (s, 3 H), 3.90 (s, 3 H), 2.50 (br. s., 3 H) |
| 59 | 4-chloro-N-methyl-3-{[5,6,7-tris(methyloxy)-4-quinazolinyl]amino}benzenesulfonamide trifluoroacetate | 2.01$^a$ | 439.0 | $^1$H NMR (400 MHz, DMSO-d$_6$) δ ppm 9.34 (br. s., 1 H), 8.32 (s, 1 H), 7.97 (d, J = 1.32 Hz, 1 H), 7.68 (s, 1 H), 7.64 (dd, J = 8.49, 1.87 Hz, 1 H), 7.43 (d, J = 8.60 Hz, 2 H), 7.16 (s, 1 H), 4.74-4.94 (m, 4 H), 3.90 (s, 3 H), 2.44 (s, 3 H), 1.34 (d, J = 5.95 Hz, 6 H) |
| 60 | N-methyl-3-[(7-(methyloxy)-5-{[2-(methyloxy)ethyl]oxy}-4-quinazolinyl)amino]-4-[(2,2,2-trifluoroethyl)oxy]benzenesulfonamide hydrochloride | 2.04$^a$ | 517.1 | $^1$H NMR (400 MHz, DMSO-d$_6$) δ ppm 11.03 (br. s., 1 H), 10.26 (br. s., 1 H), 8.47 (s, 1 H), 7.88 (s, 2 H), 7.71 (dd, J = 8.71, 2.32 Hz, 1 H), 7.38-7.54 (m, 2 H), 7.16 (s, 1 H), 4.87 (q, J = 8.75 Hz, 2 H), 3.93 (s, 3 H), 2.42 (d, J = 4.85 Hz, 3 H) |
| 61 | N-methyl-3-{[7-(methyloxy)-5-(tetrahydro-2H-pyran-4-yloxy)-4-quinazolinyl]amino}-4-[(2,2,2-trifluoroethyl)oxy]benzenesulfonamide | 2.03$^a$ | 543.1 | $^1$H NMR (400 MHz, METHANOL-d$_4$) δ ppm 9.02 (d, J = 2.26 Hz, 1 H), 8.69 (s, 1 H), 7.66 (dd, J = 8.78, 2.26 Hz, 1 H), 7.40 (d, J = 9.03 Hz, 1 H), 7.00 (s, 1 H), 5.32 (dt, J = 12.74, 6.31 Hz, 1 H), 4.18 (s, 3 H), 4.00 (s, 3 H), 3.89 (s, 3 H), 2.49 (s, 3 H), 1.53 (d, J = 6.27 Hz, 3 H) |
| 62 | N-methyl-4-[(2,2,2-trifluoro-1-methylethyl)oxy]-3-{[5,6,7-tris(methyloxy)-4-quinazolinyl]amino}benzenesulfonamide trifluoroacetate | 2.14$^a$ | 517.1 | $^1$H NMR (400 MHz, DMSO-d$_6$) δ ppm 10.93 (s, 1 H), 8.61-8.73 (m, 2 H), 8.19 (d, J = 8.28 Hz, 1 H), 7.75-7.91 (m, 2 H), 7.16 (s, 1 H), 4.19 (s, 3 H), 4.03 (s, 3 H), 3.89 (s, 3 H), 3.36 (s, 3 H), 2.55 (d, J = 5.02 Hz, 3 H) |
| 63 | N-methyl-4-(methylsulfonyl)-3-{[5,6,7-tris(methyloxy)-4-quinazolinyl]amino}benzenesulfonamide trifluoroacetate | 1.94$^a$ | 483.0 | $^1$H NMR (400 MHz, DMSO-d$_6$) δ ppm 9.83 (br. s., 1 H), 8.71 (br. s., 1 H), 8.48 (s, 1 H), 7.85-7.93 (m, 1 H), 7.80 (dd, J = 8.66, 1.88 Hz, 1 H), 7.48-7.60 (m, 2 H), 7.24-7.31 (m, 1 H), 4.92 (q, J = 8.70 Hz, 2 H), 4.30 (t, J = 5.77 Hz, 2 H), 4.02 (br. s., 2 H), 3.68 (br. s., 2 H), 3.51 (br. s., 2 H), 3.34 (br. s., 2 H), 3.15 (br. s., 2 H), 2.47 (d, J = 5.02 Hz, 3 H), 2.23 (d, J = 9.03 Hz, 2 H) |
| 64 | 3-{[5-(ethyloxy)-7-(methyloxy)-4-quinazolinyl]amino}-N-methyl-4- | 2.15$^a$ | 473.1 | $^1$H NMR (400 MHz, DMSO-d$_6$) δ ppm 10.16 (s, 1 H), 9.04 (d, J = 2.26 Hz, 1 H), 8.53 (s, 1 H), 7.76 (dd, J = 8.53, 1.51 Hz, 1 H), 7.68 (br. s., 1 H), 7.63 (dd, J = 8.66, |

| Ex. | Name | $t_R$ (min) | MS (m/z) | $^1$H NMR |
|---|---|---|---|---|
|  | [(trifluoromethyl)oxy]benzene-sulfonamide |  |  | 2.38 Hz, 1 H), 6.88 (d, J = 2.26 Hz, 1 H), 6.85 (d, J = 2.26 Hz, 1 H), 5.05 (dt, J = 12.05, 6.02 Hz, 1 H), 3.93 (s, 3 H), 2.52 (br. s., 3 H), 1.46 (d, J = 6.27 Hz, 6 H) |
| 65 | N-methyl-3-{[5-[(1-methylethyl)oxy]-7-(methyloxy)-4-quinazolinyl]amino}-4-[(trifluoromethyl)oxy]benzene-sulfonamide | 2.21$^a$ | 487.1 | $^1$H NMR (400 MHz, DMSO-d$_6$) δ ppm 10.05 (s, 1 H), 9.01 (d, J = 2.01 Hz, 1 H), 8.51 (s, 1 H), 7.49-7.60 (m, 2 H), 7.44 (q, J = 5.02 Hz, 1 H), 6.86 (d, J = 2.26 Hz, 1 H), 6.80 (d, J = 2.26 Hz, 1 H), 5.53 (dt, J = 12.99, 6.43 Hz, 1 H), 4.44 (q, J = 6.94 Hz, 2 H), 3.92 (s, 3 H), 2.48 (d, J = 5.02 Hz, 3 H), 1.54 (d, J = 6.27 Hz, 3 H), 1.46 (t, J = 7.03 Hz, 3 H) |
| 66 | 3-{[5-(ethyloxy)-7-(methyloxy)-4-quinazolinyl]amino}-N-methyl-4-[(2,2,2-trifluoro-1-methylethyl)oxy]benzene-sulfonamide | 2.14$^a$ | 501.1 | $^1$H NMR (400 MHz, DMSO-d$_6$) δ ppm 9.84 (s, 1 H), 8.73 (d, J = 1.76 Hz, 1 H), 8.45 (s, 1 H), 7.50-7.60 (m, 2 H), 7.40-7.49 (m, 1 H), 6.84 (d, J = 2.26 Hz, 1 H), 6.80 (d, J = 2.26 Hz, 1 H), 5.41-5.55 (m, 1 H), 4.92-5.02 (m, 1 H), 3.93 (s, 3 H), 2.49 (d, J = 5.02 Hz, 3 H), 1.52 (d, J = 6.27 Hz, 3 H), 1.44 (dd, J = 6.02, 2.26 Hz, 6 H) |
| 67 | N-methyl-3-{[5-[(1-methylethyl)oxy]-7-(methyloxy)-4-quinazolinyl]amino}-4-[(2,2,2-trifluoro-1-methyl-ethyl)oxy]benzenesulfonamide | 2.20$^a$ | 515.1 | $^1$H NMR (400 MHz, METHANOL-d$_4$) δ ppm 8.81 (s, 1 H), 8.72 (s, 1 H), 8.35 (d, J = 8.28 Hz, 1 H), 8.02 (dd, J = 8.28, 1.76 Hz, 1 H), 7.78 (s, 1 H), 7.30 (s, 1 H), 4.12 (s, 3 H), 4.10 (s, 3 H), 3.24 (s, 3 H), 2.67 (s, 3 H) |
| 68 | 3-{[6,7-bis(methyloxy)-4-quinazolinyl]amino}-N-methyl-4-(methylsulfonyl)benzenesulfon-amide trifluoroacetate | 1.78$^a$ | 453.0 | $^1$H NMR (400 MHz, DMSO-d$_6$) δ ppm 9.62 (br. s., 1 H), 8.43 (s, 1 H), 8.00 (d, J = 2.01 Hz, 1 H), 7.78 (s, 1 H), 7.69 (dd, J = 8.78, 2.26 Hz, 1 H), 7.53 (d, J = 8.78 Hz, 1 H), 7.42-7.50 (m, 1 H), 7.22 (s, 1 H), 5.39 (dt, J = 12.80, 6.40 Hz, 1 H), 3.96 (s, 3 H), 3.95 (s, 3 H), 2.47 (d, J = 5.02 Hz, 3 H), 1.36 (d, J = 6.27 Hz, 3 H) |
| 69 | 3-{[6,7-bis(methyloxy)-4-quinazolinyl]amino}-N-methyl-4-[(2,2,2-trifluoro-1-methylethyl)oxy]benzenesulfon-amide | 1.96$^a$ | 487.1 | $^1$H NMR (400 MHz, DMSO-d$_6$) δ ppm 9.45 (br. s., 1 H), 8.44 (s, 1 H), 8.37 (d, J = 9.03 Hz, 1 H), 7.90 (d, J = 1.76 Hz, 1 H), 7.54 (dd, J = 8.53, 2.26 Hz, 1 H), 7.15-7.37 (m, 4 H), 4.20 (t, J = 6.27 Hz, 2 H), 3.52 (t, J = 6.27 Hz, 2 H), 3.29 (s, 3 H), 2.77 (s, 6 H), 2.43 (s, 3 H), 2.03 (quin, J = 6.27 Hz, 2 H) |
| 70 | 3-{[6-iodo-7-(methyloxy)-4-quinazolinyl]amino}-N-methyl-4-[(2,2,2-trifluoroethyl)oxy]benzene-sulfonamide | 2.06$^a$ | 568.7 | $^1$H NMR (400 MHz, DMSO-d$_6$) δ ppm 9.38 (br. s., 1 H), 8.34 (s, 1 H), 7.97 (d, J = 2.26 Hz, 1 H), 7.72 (s, 1 H), 7.67 (dd, J = 8.66, 2.13 Hz, 1 H), 7.39-7.52 (m, 2 H), 7.17 (s, 1 H), 4.88 (q, J = 8.95 Hz, 2 H), 4.08-4.29 (m, 4 H), 2.46 (s, 3 H), 1.43 (q, J = 7.03 Hz, 6 H) |
| 71 | 3-{[6,7-bis(ethyloxy)-4-quinazolinyl]amino}-N-methyl-4-[(2,2,2-trifluoro-ethyl)oxy]benzenesulfonamide | 2.02$^a$ | 500.9 | $^1$H NMR (400 MHz, DMSO-d$_6$) δ ppm 8.91 (d, J = 9.04 Hz, 1 H), 8.77 (s, 1 H), 8.59 (d, J = 2.26 Hz, 1 H), 8.46 (dd, J = 9.04, 2.26 Hz, 1 H), 7.77 (d, J = 2.01 Hz, 1 H), 7.63 (dd, J = 8.53, 2.26 Hz, 1 H), 7.34 (q, J = 4.77 Hz, 1 H), 7.24 (d, J = 8.78 Hz, 1 H), 2.79 (s, 6 H), 2.43 (d, J = 4.77 Hz, 3 H) |
| 72 | 4-(dimethylamino)-N-methyl-3-((7-nitroquinazolin-4-yl)amino)benzenesulfonamide hydrochloride | 2.05$^a$ | 403.0 | $^1$H NMR (400 MHz, DMSO-d$_6$) δ ppm 9.03 (s, 1 H), 8.28 (s, 1 H), 8.02-8.09 (m, 2 H), 7.50 (dd, J = 8.53, 2.26 Hz, 1 H), 7.30 (q, J = 4.68 Hz, 1 H), 7.22 (d, J = 8.53 Hz, 1 H), 6.91 (dd, J = 8.78, 2.26 Hz, 1 H), 6.72 (d, J = 2.26 Hz, 1 H), 6.07 (s, 2 H), 2.76 (s, 6 H), 2.43 (d, J = 4.77 Hz, 3 H) |
| 73 | 4-(dimethylamino)-N-methyl-3-[(7-{[3-(4-morpholinyl)propyl]oxy}-4-quinazolinyl)amino]benzene-sulfonamide hydrochloride | 1.68$^a$ | 501.2 | $^1$H NMR (400 MHz, DMSO-d$_6$) δ ppm 11.00 (br. s., 1 H), 8.79 (s, 1 H), 8.15 (s, 1 H), 7.69 (d, J = 2.26 Hz, 1 H), 7.65 (dd, J = 8.78, 2.26 Hz, 1 H), 7.27-7.35 (m, 2 H), 7.24 (d, J = 8.78 Hz, 1 H), 4.29-4.40 (m, 4 H), 3.75-3.83 (m, 4 H), 3.37 (s, 3 H), 3.37 (s, 3 H), 2.81 (s, 6 H), 2.43 (d, J = 5.02 Hz, 3 H) |
| 74 | N-methyl-3-[(7-{[3-(4-morpholinyl)propyl]oxy}-4-quinazolinyl)amino]-4-[(2,2,2-trifluoroethyl)oxy]benzene-sulfonamide trifluoroacetate | 1.63$^a$ | 556.1 | $^1$H NMR (400 MHz, DMSO-d$_6$) δ ppm 10.20 (s, 1 H), 9.13 (d, J = 2.26 Hz, 1 H), 8.56 (s, 1 H), 7.75 (dd, J = 8.66, 1.63 Hz, 1 H), 7.68 (s, 1 H), 7.62 (dd, J = 8.53, 2.26 Hz, 1 H), 6.89 (d, J = 2.26 Hz, 1 H), 6.83 (d, J = 2.26 Hz, 1 H), 4.43 (q, J = 7.03 Hz, 2 H), |

-continued

| Ex. | Name | $t_R$ (min) | MS (m/z) | ¹H NMR |
|---|---|---|---|---|
| | | | | 3.93 (s, 3 H), 2.52 (s, 3 H), 1.50 (t, J = 6.90 Hz, 3 H) |
| 75 | N-methyl-3-[(7-{[3-(methyloxy)propyl]oxy}-4-quinazolinyl)amino]-4-[(2,2,2-trifluoroethyl)oxy]benzene-sulfonamide | 1.97ᵃ | 501.1 | ¹H NMR (400 MHz, DMSO-d₆) δ ppm 10.99 (s, 1 H), 8.82-8.92 (m, 2 H), 7.70 (dd, J = 8.78, 2.26 Hz, 1 H), 7.50-7.61 (m, 2 H), 7.22 (s, 1 H), 5.12 (q, J = 8.78 Hz, 2 H), 4.17 (s, 3 H), 4.04 (s, 3 H), 3.92 (s, 3 H), 2.47 (d, J = 4.77 Hz, 3 H) |
| 76 | 4-(dimethylamino)-N-methyl-3-[(7-{[3-(methyl-oxy)propyl]oxy}-4-quin-azolinyl)amino]benzenesulfon-amide | 1.38ᵃ | 446.2 | ¹H NMR (400 MHz, METHANOL-d₄) δ ppm 9.02 (d, J = 2.01 Hz, 1 H), 8.54 (s, 1 H), 7.59 (dd, J = 8.78, 2.26 Hz, 1 H), 7.36 (d, J = 8.78 Hz, 1 H), 6.79 (d, J = 2.01 Hz, 1 H), 6.70-6.76 (m, 1 H), 5.28 (dt, J = 12.55, 6.27 Hz, 1 H), 4.08 (s, 3 H), 3.90 (s, 3 H), 2.50 (s, 3 H), 1.52 (d, J = 6.27 Hz, 3 H) |
| 77 | 3-{[5,7-bis(methyloxy)-4-quinazolinyl]amino}-N-methyl-4-(methylsulfonyl)benzene-sulfonamide trifluoroacetate | 1.87ᵃ | 453.1 | ¹H NMR (400 MHz, DMSO-d₆) δ ppm 10.57 (br. s., 1 H), 8.76 (s, 1 H), 8.63 (br. s., 1 H), 7.79 (q, J = 4.68 Hz, 1 H), 7.59 (d, J = 11.54 Hz, 1 H), 6.93 (d, J = 2.01 Hz, 1 H), 6.85 (d, J = 2.26 Hz, 1 H), 5.08 (q, J = 8.78 Hz, 2 H), 4.11 (s, 3 H), 3.98 (s, 3 H), 2.54 (d, J = 4.77 Hz, 3 H) |
| 78 | 3-(7-hydroxy-6-methoxyquinazolin-4-ylamino)-N-methyl-4-(2,2,2-trifluoro-ethoxy)benzenesulfonamide | 0.80ᵇ | 458.9 | ¹H NMR (400 MHz, DMSO-d₆) δ ppm 10.66 (br. s., 1 H), 8.64 (s, 1 H), 7.91 (br. s., 1 H), 7.86 (br. s., 1 H), 7.77 (d, J = 10.58 Hz, 1 H), 7.45-7.57 (m, 2 H), 7.23-7.32 (m, 1 H), 4.81-4.96 (m, 2 H), 4.17-4.31 (m, 2 H), 3.95 (s, 3 H), 2.44 (d, J = 4.63 Hz, 3 H), 1.42 (t, J = 6.73 Hz, 3 H) |
| 79 | 3-(7-isopropoxy-6-methoxy-quinazolin-4-ylamino)-N-methyl-4-(2,2,2-trifluoro-ethoxy)-benzenesulfonamide | 0.94ᵇ | 501.0 | ¹H NMR (400 MHz, DMSO-d₆) δ ppm 10.64 (br. s., 1 H), 8.80 (s, 1 H), 8.34 (br. s., 1 H), 7.76 (dd, J = 8.66, 2.13 Hz, 1 H), 7.48-7.61 (m, 2 H), 7.09 (d, J = 2.01 Hz, 1 H), 6.91 (d, J = 2.01 Hz, 1 H), 5.05 (q, J = 8.78 Hz, 2 H), 4.55-4.63 (m, 2 H), 3.98 (s, 3 H), 3.77-3.83 (m, 2 H), 3.23 (s, 3 H), 2.47 (d, J = 5.02 Hz, 3 H), 1.04 (d, J = 6.02 Hz, 3 H) |
| 80 | 3-(7-ethoxy-6-methoxy-quinazolin-4-ylamino)-N-methyl-4-(2,2,2-trifluoro-ethoxy)-benzenesulfonamide trifluoroacetate | 1.03ᵇ | 487.1 | ¹H NMR (400 MHz, DMSO-d₆) δ ppm 11.17 (br. s., 1 H), 8.75 (s, 1 H), 8.02 (s, 1 H), 7.76-7.89 (m, 2 H), 7.51-7.58 (m, 2 H), 7.39 (s, 2 H), 4.90 (q, J = 8.60 Hz, 2 H), 4.26-4.34 (m, 2 H), 3.97 (s, 3 H), 3.72-3.78 (m, 2 H), 3.32 (s, 3 H), 2.45 (d, J = 4.85 Hz, 3 H) |
| 81 | 3-[6-methoxy-7-(2-methoxy-ethoxy)-quinazolin-4-ylamino]-N-methyl-4-(2,2,2-trifluoro-ethoxy)-benzenesulfonamide trifluoroacetate | 1.00ᵇ | 517.1 | ¹H NMR (400 MHz, DMSO-d₆) δ ppm 9.91 (s, 1 H), 8.87 (d, J = 1.76 Hz, 1 H), 8.48 (s, 1 H), 7.48-7.58 (m, 2 H), 7.44 (q, J = 4.77 Hz, 1 H), 6.95 (d, J = 2.26 Hz, 1 H), 6.87 (d, J = 2.26 Hz, 1 H), 5.09 (q, J = 8.78 Hz, 2 H), 4.98 (dt, J = 9.54, 5.02 Hz, 1 H), 3.86-3.95 (m, 5 H), 3.45-3.56 (m, 2 H), 2.48 (d, J = 4.77 Hz, 3 H), 2.09-2.19 (m, 2 H), 1.69-1.85 (m, 2 H) |
| 82 | 3-{[5,7-bis(methyloxy)-4-quinazolinyl]amino}-N-methyl-4-[(2,2,2-trifluoro-1-methylethyl)oxy]benzene-sulfonamide hydrochloride | 2.07ᵃ | 487.1 | ¹H NMR (400 MHz, METHANOL-d₄) δ ppm 9.23 (d, J = 2.26 Hz, 1 H), 8.46 (s, 1 H), 7.52 (dd, J = 8.78, 2.26 Hz, 1 H), 7.32 (d, J = 8.78 Hz, 1 H), 6.71 (dd, J = 9.16, 2.13 Hz, 2 H), 5.27 (dt, J = 12.61, 6.37 Hz, 1 H), 4.04 (s, 3 H), 3.86 (s, 3 H), 2.50 (s, 3 H), 1.53 (d, J = 6.27 Hz, 3 H) |
| 83 | 3-{[5,7-bis(methyloxy)-4-quinazolinyl]amino}-N-methyl-4-[(2,2,2-trifluoro-1-methylethyl)oxy]benzene-sulfonamide hydrochloride | 2.07ᵃ | 487.1 | ¹H NMR (400 MHz, DMSO-d₆) δ ppm 9.78 (s, 1 H), 8.93 (s, 1 H), 8.42 (s, 1 H), 7.85 (d, J = 2.26 Hz, 1 H), 7.70 (dd, J = 8.66, 2.13 Hz, 1 H), 7.45 (d, J = 8.53 Hz, 2 H), 7.21 (s, 1 H), 4.87 (q, J = 8.78 Hz, 2 H), 4.00 (s, 3 H), 2.46 (d, J = 4.77 Hz, 3 H) |
| 84 | 3-((6-aminoquinazolin-4-yl)amino)-4-(dimethylamino)-N-methylbenzenesulfonamide | 1.54ᵃ | 372.9 | ¹H NMR (400 MHz, DMSO-d₆) δ ppm 9.05 (br. s., 1 H), 8.31 (s, 1 H), 8.03-8.11 (m, 2 H), 7.50 (dd, J = 8.66, 1.88 Hz, 1 H), 7.22 (d, J = 8.53 Hz, 1 H), 6.94 (dd, J = 8.91, 1.88 Hz, 1 H), 6.60-6.69 (m, 1 H), 6.55 (d, J = 2.01 Hz, 1 H), 2.80 (d, J = 4.77 Hz, 3 H), 2.76 (s, 6 H), 2.43 (s, 3 H) |
| 85 | 3-((7-aminoquinazolin-4-yl)amino)-4- | 1.61ᵃ | 373.0 | ¹H NMR (400 MHz, DMSO-d₆) δ ppm 8.95 (s, 1 H), 8.46 (d, J = 2.26 Hz, 1 H), 8.33 (s, |

| Ex. | Name | $t_R$ (min) | MS (m/z) | $^1$H NMR |
|---|---|---|---|---|
|  | (dimethylamino)-N-methylbenzenesulfonamide |  |  | 1 H), 7.56 (d, J = 8.78 Hz, 1 H), 7.50 (dd, J = 8.28, 2.26 Hz, 1 H), 7.29-7.39 (m, 2 H), 7.26 (dd, J = 8.78, 2.26 Hz, 1 H), 7.14 (d, J = 2.26 Hz, 1 H), 5.76 (s, 2 H), 2.79 (s, 6 H), 2.45 (d, J = 5.02 Hz, 3 H) |
| 86 | 4-(dimethylamino)-3-((6-(dimethylamino)quinazolin-4-yl)amino)-N-methylbenzenesulfonamide bis(trifluoroacetate) | 1.80$^a$ | 401.0 | $^1$H NMR (400 MHz, DMSO-d$_6$) δ ppm 10.97 (br. s., 1 H), 8.65 (s, 1 H), 7.59-7.71 (m, 3 H), 7.46 (dd, J = 9.03, 2.26 Hz, 1 H), 7.38 (s, 1 H), 7.28-7.35 (m, 1 H), 7.21-7.26 (m, 1 H), 2.85 (s, 3 H), 2.81 (s, 6 H), 2.42 (d, J = 5.27 Hz, 3 H) |
| 87 | 4-(dimethylamino)-N-methyl-3-((6-(methylamino)quinazolin-4-yl)amino)benzenesulfonamide bis(trifluoroacetate) | 1.71$^a$ | 387.0 | $^1$H NMR (400 MHz, DMSO-d$_6$) δ ppm 10.77 (br. s., 1 H), 8.78-8.87 (m, 1 H), 8.75 (s, 1 H), 8.06 (dd, J = 8.91, 1.88 Hz, 1 H), 7.87 (d, J = 9.04 Hz, 1 H), 7.74 (d, J = 2.01 Hz, 1 H), 7.63 (dd, J = 8.78, 2.26 Hz, 1 H), 7.32 (q, J = 5.02 Hz, 1 H), 7.23 (d, J = 8.78 Hz, 1 H), 2.80 (s, 6 H), 2.43 (d, J = 5.02 Hz, 3 H) |
| 88 | 4-(dimethylamino)-N-methyl-3-((7-(methylamino)quinazolin-4-yl)amino)benzenesulfonamide | 1.71$^a$ | 387.0 | $^1$H NMR (400 MHz, DMSO-d$_6$) δ ppm 11.14 (br. s., 1 H), 8.71 (s, 1 H), 7.72-7.77 (m, 1 H), 7.60-7.72 (m, 4 H), 7.33 (q, J = 5.19 Hz, 1 H), 7.24 (d, J = 8.53 Hz, 1 H), 3.13 (s, 6 H), 2.81 (s, 6 H), 2.42 (d, J = 5.27 Hz, 3 H) |

$^a$LCMS Method: Agilent 1100 Series LC/MSD SL or VL using electrospray positive [ES + ve to give M + H$^+$] equipped with a Sunfire C18 5.0 μm column (3.0 mm × 50 mm, i.d.), eluting with 0.05% TFA in water (solvent A) and 0.05% TFA in acetonitrile (solvent B), using the following elution gradient: 10%-100% (solvent B) over 2.5 minutes and holding at 100% for 1.7 minutes at a flow rate of 1.0 ml/minutes.
$^b$LCMS Method: Agilent 1200 Series LC/MSD VL using electrospray positive [ES + ve to give M + H$^+$] equipped with a shim-pack XR-ODS 2.2 μm column (3.0 mm × 30 mm, 3.0 mm i.d.) eluting with 0.0375% TFA in water (solvent A) and 0.01875% TFA in acetonitrile (solvent B), using the following elution gradient 10-80% (solvent B) over 0.9 minutes and holding at 80% for 0.6 minutes at a flow rate of 1.2 mL/minutes.

Pharmaceutical Compositions

Example A

Tablets are prepared using conventional methods and are formulated as follows:

| Ingredient | Amount per tablet |
|---|---|
| Compound of Example 1 | 5 mg |
| Microcrystalline cellulose | 100 mg |
| Lactose | 100 mg |
| Sodium starch glycollate | 30 mg |
| Magnesium stearate | 2 mg |
| Total | 237 mg |

Example B

Capsules are prepared using conventional methods and are formulated as follows:

| Ingredient | Amount per tablet |
|---|---|
| Compound of Example 3 | 15 mg |
| Dried starch | 178 mg |
| Magnesium stearate | 2 mg |
| Total | 195 mg |

Biological Assay(s)

Materials: His-MBP-TEV-Full length human TNNI3K (hTNNI3K) was expressed in Baculokinase system and purified from amylase affinity column followed by Superdex200. The fluorescent ligand 5-({[2-({[3-({4-[(5-hydroxy-2-methylphenyl)amino]-2-pyrimidinyl}amino)phenyl]carbonyl}amino)ethyl]amino}carbonyl)-2-(6-hydroxy-3-oxo-3H-xanthen-9-yl)benzoic acid was used. The preparation of this fluorescent ligand is disclosed in U.S. Provisional Patent Application No. 61/237,815 filed Aug. 28, 2009, the disclosure of which is incorporated by reference herein. The other buffer components, including MgCl$_2$ (Catalog Number M1028), Bis-Tris (Catalog Number B7535), DTT (Catalog Number D9779) and Chaps (Catalog Number C3023) were purchased from Sigma-Aldrich.

Biological Assay Method I:

A fluorescent polarization assay was used to determine does response of compound inhibition on hTNNI3K ATP binding. The binding of 5-({[2-({[3-({4-[(5-hydroxy-2-methylphenyl)amino]-2-pyrimidinyl}amino)phenyl]carbonyl}amino)ethyl]amino}carbonyl)-2-(6-hydroxy-3-oxo-3H-xanthen-9-yl)benzoic acid to the hTNNI3K ATP binding pocket results in increase of fluorescent polarization and the displacement of 5-({[2-({[3-({4-[(5-hydroxy-2-methylphenyl)amino]-2-pyrimidinyl}amino)phenyl]carbonyl}amino)ethyl]amino}carbonyl)-2-(6-hydroxy-3-oxo-3H-xanthen-9-yl)benzoic acid by a competitive compound leads to fluorescent polarization decrease.

Solution 1: Ten (10) mL of a 5 nM 5-({[2-({[3-({4-[(5-hydroxy-2-methylphenyl)amino]-2-pyrimidinyl}amino)phenyl]carbonyl}amino)ethyl]amino}carbonyl)-2-(6-hydroxy-3-oxo-3H-xanthen-9-yl)benzoic acid solution (Solution 1) was prepared by mixing 5 μL of 1M DTT and 80 μL of 10% (w/v) Chaps and 5 μL of a 10 μM 5-({[2-({[3-({4-[(5-hydroxy-2-methylphenyl)amino]-2-pyrimidinyl}amino)phenyl]carbonyl}amino) ethyl]amino}carbonyl)-2-(6-hydroxy-3-oxo-3H-xanthen-9-yl)benzoic acid stock solution into 9910 μL buffer (20 mM Tris, 15 mM MgCl$_2$, pH 7.5). (Stock solution: 10 μM solution of 5-({[2-({[3-({4-[(5-hydroxy-2-methylphenyl)amino]-2-pyrimidinyl}amino)phenyl]carbonyl}amino)ethyl]amino}carbonyl)-2-(6-hydroxy-3-oxo-3H-xanthen-9-yl)benzoic acid in 100% DMSO)

Solution 2 was formed by mixing 53.8 μL of 2.6 μM hTNNI3K with a 6946.2 μL aliquot of Solution 1 (the above 5-({[2-({[3-({4-[(5-hydroxy-2-methylphenyl)amino]-2-pyrimidinyl}amino)phenyl]carbonyl}amino)ethyl]amino}carbonyl)-2-(6-hydroxy-3-oxo-3H-xanthen-9-yl)benzoic acid solution) to make up a 7 mL of mixture of hTNNI3K and 5-({[2-({[3-({4-[(5-hydroxy-2-methylphenyl)amino]-2-pyrimidinyl}amino)phenyl]carbonyl}amino)ethyl]amino}carbonyl)-2-(6-hydroxy-3-oxo-3H-xanthen-9-yl)benzoic acid (Solution 2).

Fifty (50) nL of inhibitors in DMSO (or DMSO controls) were stamped into a 384-well low volume Greiner black plate, followed by addition of 5 μL of Solution 1 to column 18 and 5 μL Solution 2 to columns 1-17 and 19-24 of the plate. The plate was then spun at 500 rpm for 30 seconds and incubated at room temperature for 60 minutes. After that, the fluorescent polarization was measured on Analyst (ex/em: 485/530 nm, Dichroic: 505). For dose response experiments, normalized data were fit by ABASE/$XC_{50}$ and $pXC_{50}$=(log((b−y)/(y−a)))/d−log(x), where x is the compound concentration and y is the % activity at specified compound concentration, a is the minimum % activity, b is the maximum % activity, and d is the Hill slope.

The $pXC_{50}$s are averaged to determine a mean value, for a minimum of 2 experiments. As determined using the above method, the compounds of Examples 1-88 exhibited a $pXC_{50}$ greater than or equal to 6.0. Preferred compounds of the invention, including the compounds of Examples 1, 3, 4, 5, 10, 11, 14, 16, 17, 18, 19, 20, 22, 26, 28, 30, 36, 38, 39, 40, 42, 44, 45, 47, 50, 51, 53, 55, 58, 59, 60, 61, 64, 65, 67, 69, 70, 74, 75, 77, 80, 81, 84, 85, 86, 87, and 88, exhibited a $pXC_{50}$ of between approximately 7.0 and approximately 8.0. For instance, the compound of Example 3 inhibited hTNNI3K in the above method with a mean $pXC_{50}$ of approximately 7.1. More preferred compounds of the invention, including the compounds of Examples 21, 25, 27, 31, 32, 35, 37, 46, 48, 49, 54, 56, 62, 66, 68, 71, 73, 76, 82, and 83, exhibited a $pXC_{50}$ of between approximately 8.0 and approximately 9.0. For instance, the compound of Example 68 inhibited hTNNI3K in the above method with a mean $pXC_{50}$ of approximately 8.4.

What is claimed is:

1. A compound according to Formula I:

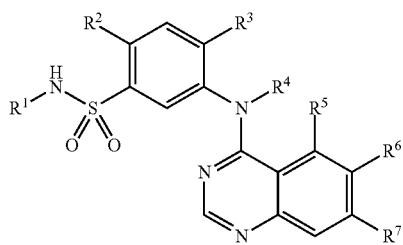

wherein:
$R^1$ is ($C_1$-$C_4$)alkyl;
$R^2$ is H or halogen;
$R^3$ is H, halogen, ($C_1$-$C_8$)alkyl, ($C_1$-$C_8$)haloalkyl, hydroxyl, hydroxy($C_1$-$C_8$)alkyl-, ($C_1$-$C_8$)alkoxy, ($C_3$-$C_8$)cycloalkyloxy, ($C_1$-$C_8$)haloalkoxy, ($C_1$-$C_8$)alkylthio-, ($C_1$-$C_8$)haloalkylthio-, ($C_3$-$C_8$)cycloalkylthio-, ($C_1$-$C_8$)alkylsulfonyl, ($C_1$-$C_8$)haloalkylsulfonyl, ($C_3$-$C_8$)cycloalkylsulfonyl, phenyl, 5-membered heteroaryl, or —N($R^a$)($R^b$), wherein said phenyl or heteroaryl is optionally substituted one to three times, independently, by halogen, ($C_1$-$C_6$)alkyl, ($C_1$-$C_4$)haloalkyl, ($C_1$-$C_6$)alkoxy, ($C_1$-$C_4$)haloalkoxy, hydroxy($C_1$-$C_4$)alkyl-, or —N($R^a$)($R^b$);
each $R^a$ is independently ($C_1$-$C_4$)alkyl, wherein said ($C_1$-$C_4$)alkyl is optionally substituted one to three times, independently, by halogen, hydroxyl, ($C_1$-$C_6$)alkoxy, amino, ($C_1$-$C_6$)alkylamino, (($C_1$-$C_6$)alkyl)(($C_1$-$C_6$)alkyl)amino, —$CO_2$H, —$CO_2$($C_1$-$C_6$)alkyl, —$CONH_2$, —$CONH$($C_1$-$C_6$)alkyl, or —$CON$(($C_1$-$C_6$)alkyl)(($C_1$-$C_6$)alkyl), and
$R^b$ is ($C_1$-$C_4$)alkyl;
or $R^a$ and $R^b$ taken together with the nitrogen atom to which they are attached form a 5-membered or 6-membered heterocyclic ring, optionally containing one additional heteroatom selected from nitrogen, oxygen and sulfur, wherein said ring is optionally substituted one or two times, independently, by halogen, ($C_1$-$C_4$)alkyl, ($C_1$-$C_4$)haloalkyl, amino, ($C_1$-$C_4$)alkylamino, (($C_1$-$C_4$)alkyl)(($C_1$-$C_4$)alkyl)amino, hydroxyl, hydroxy($C_1$-$C_4$)alkyl-, oxo, ($C_1$-$C_4$)alkoxy,($C_1$-$C_4$)haloalkoxy, or ($C_1$-$C_4$)alkoxy($C_1$-$C_4$)alkyl;
$R^4$ is H;
$R^5$, $R^6$, and $R^7$ are each, independently, H, halogen, nitro, amino, ($C_1$-$C_4$)alkylamino, (($C_1$-$C_4$)alkyl)(($C_1$-$C_4$)alkyl)amino, hydroxyl, or $OR^c$; and
each $R^c$ is, independently, ($C_1$-$C_8$)alkyl or a 5-6 membered heterocycloalkyl, wherein said ($C_1$-$C_8$)alkyl is optionally substituted one to three times, independently, by halogen, hydroxyl, ($C_1$-$C_4$)alkoxy, amino, ($C_1$-$C_4$)alkylamino, or —N($R^a$)($R^b$);
or $R^6$ and $R^7$ taken together represent —O($C_1$-$C_2$)alkylO—;
or a salt thereof.

2. The compound or salt according to claim 1, wherein $R^3$ is H, halogen, ($C_1$-$C_6$)alkyl, ($C_1$-$C_6$)haloalkyl, ($C_1$-$C_6$)alkoxy, ($C_5$-$C_6$)cycloalkyloxy, ($C_1$-$C_6$)haloalkoxy, ($C_1$-$C_6$)alkylthio-, ($C_5$-$C_6$)cycloalkylthio-, ($C_1$-$C_6$)haloalkylthio-, ($C_1$-$C_6$)alkylsulfonyl, ($C_1$-$C_6$)haloalkylsulfonyl, ($C_5$-$C_6$)cycloalkylsulfonyl, phenyl, 5-membered heteroaryl, or —N($R^a$)($R^b$), wherein said heteroaryl contains one heteroatom selected from N, O and S, or contains one nitrogen atom and optionally contains 1 additional heteroatom selected from N, O and S, or contains two nitrogen atoms and optionally contains 1 additional heteroatom selected from N, O and S; and said phenyl or heteroaryl is optionally substituted one to three times, independently, by halogen, ($C_1$-$C_6$)alkyl, ($C_1$-$C_4$)haloalkyl, or —N($R^a$)($R^b$).

3. The compound or salt according to claim 1, wherein $R^3$ is H, halogen, ($C_1$-$C_8$)alkyl, ($C_1$-$C_8$)haloalkyl, hydroxyl, hydroxy($C_1$-$C_8$)alkyl-, ($C_1$-$C_8$)alkoxy, ($C_3$-$C_8$)cycloalkyloxy, ($C_1$-$C_8$)haloalkoxy, ($C_1$-$C_8$)alkylthio-, ($C_1$-$C_8$)haloalkylthio-, ($C_3$-$C_8$)cycloalkylthio-, phenyl, 5-membered heteroaryl, or —N($R^a$)($R^b$), wherein said phenyl or heteroaryl is optionally substituted one to three times, independently, by halogen, ($C_1$-$C_6$)alkyl, ($C_1$-$C_4$)haloalkyl, ($C_1$-$C_6$)alkoxy, ($C_1$-$C_4$)haloalkoxy, hydroxy($C_1$-$C_4$)alkyl-, or —N($R^a$)($R^b$).

4. The compound or salt according to claim 1, wherein $R^3$ is H, halogen, $C_1$-$C_6$ alkyl, $C_1$-$C_6$ haloalkyl, hydroxy$C_1$-$C_6$ alkyl-, $C_1$-$C_6$ alkoxy, ($C_3$-$C_6$)cycloalkyloxy, $C_1$-$C_6$ haloalkoxy, $C_1$-$C_6$ alkylthio-, ($C_3$-$C_6$)cycloalkylthio-, $C_1$-$C_6$ haloalkylthio-, phenyl, 5-membered heteroaryl, or —N($R^a$)($R^b$), wherein said heteroaryl contains one heteroatom selected from N, O and S, or contains one nitrogen atom and optionally contains 1 additional heteroatom selected from N, O and S, or contains two nitrogen atoms and optionally contains 1 additional heteroatom selected from N, O and S; and said phenyl or heteroaryl is optionally substituted one to three times, independently, by halogen, $(C_1\text{-}C_6)$alkyl, $(C_1\text{-}C_4)$haloalkyl, or —N($R^a$)($R^b$).

5. The compound or salt according to claim 1, wherein $R^3$ is H, halogen, $(C_1\text{-}C_4)$alkoxy, $(C_5\text{-}C_6)$cycloalkyloxy, $(C_1\text{-}C_4)$haloalkoxy, $(C_1\text{-}C_4)$alkylthio-, $(C_1\text{-}C_4)$haloalkylthio-, $(C_5\text{-}C_6)$cycloalkylthio-, $(C_1\text{-}C_4)$alkylsulfonyl, $(C_1\text{-}C_4)$haloalkylsulfonyl, $(C_5\text{-}C_6)$cycloalkylsulfonyl, or —N($R^a$)($R^b$).

6. The compound or salt according to claim 1, wherein:
each $R^a$ is independently —$CH_3$, —$CH_2CH_3$, or —$CH_2CF_3$; and
$R^b$ is —$CH_3$;
or $R^a$ and $R^b$ taken together with the nitrogen to which they are attached represent pyrrolidin-1-yl, piperidin-1-yl, or morpholin-4-yl, wherein said pyrrolidin-1-yl, piperidin-1-yl, or morpholin-4-yl is optionally substituted one or two times, independently, by F, —$CH_3$, or —$CF_3$.

7. The compound or salt according to claim 1, wherein:
$R^5$, $R^6$, and $R^7$ are each, independently, H, halogen, nitro, amino, $(C_1\text{-}C_4)$alkylamino, $((C_1\text{-}C_4)$alkyl$)((C_1\text{-}C_4)$alkyl)amino, hydroxyl, or $OR^c$, and each $R^c$ is, independently, $(C_1\text{-}C_4)$alkyl, pyrrolidinyl, tetrahydrofuranyl, tetrahydrothienyl, piperidinyl, piperazinyl, morpholinyl, tetrahydropyranyl, tetrahydro-4H-1,4-thiazinyl, or 1,4-dioxanyl, wherein said $(C_1\text{-}C_4)$alkyl is optionally substituted by halogen, hydroxyl, trifluoromethyl, $(C_1\text{-}C_4)$alkoxy, amino, $(C_1\text{-}C_4)$alkylamino, $((C_1\text{-}C_4)$alkyl$)((C_1\text{-}C_4)$alkyl)amino, pyrrolidinyl, piperidinyl, piperazinyl, or morpholinyl;
or $R^6$ and $R^7$ taken together represent —O$(C_1\text{-}C_2)$alkylO—.

8. The compound or salt according to claim 1, wherein $R^6$ is H.

9. The compound or salt according to claim 1, wherein:
$R^6$ and $R^7$ are each $OR^c$; and
each $R^c$ is, independently, $(C_1\text{-}C_8)$alkyl, optionally substituted one to three times, independently, by halogen, hydroxyl, $(C_1\text{-}C_4)$alkoxy, amino, $(C_1\text{-}C_4)$alkylamino, or $((C_1\text{-}C_4)$alkyl$)((C_1\text{-}C_4)$alkyl)amino.

10. The compound or salt according to claim 1, wherein:
$R^1$ is $(C_1\text{-}C_4)$alkyl;
$R^2$ is H or halogen;
$R^3$ is H, halogen, $(C_1\text{-}C_4)$alkoxy, $(C_5\text{-}C_6)$cycloalkyloxy, $(C_1\text{-}C_4)$haloalkoxy, $(C_1\text{-}C_4)$alkylthio-, $(C_1\text{-}C_4)$haloalkylthio-, $(C_5\text{-}C_6)$cycloalkylthio-, $(C_1\text{-}C_4)$alkylsulfonyl, $(C_1\text{-}C_4)$haloalkylsulfonyl, $(C_5\text{-}C_6)$cycloalkylsulfonyl, or —N($R^a$)($R^b$);
each $R^a$ is independently $(C_1\text{-}C_4)$alkyl, wherein said $(C_1\text{-}C_4)$alkyl is optionally substituted one to three times, independently, by halogen, hydroxyl, $(C_1\text{-}C_4)$alkoxy, amino, $(C_1\text{-}C_4)$alkylamino, $((C_1\text{-}C_4)$alkyl$)((C_1\text{-}C_4)$alkyl)amino, —$CO_2H$, —$CO_2(C_1\text{-}C_4)$alkyl, —$CONH_2$, —$CONH(C_1\text{-}C_4)$alkyl, or —$CON((C_1\text{-}C_4)$alkyl$)((C_1\text{-}C_4)$alkyl), and
$R^b$ is $(C_1\text{-}C_4)$alkyl;
or $R^a$ and $R^b$ taken together with the nitrogen atom to which they are attached form a 5-membered or 6-membered heterocyclic ring, optionally containing one additional heteroatom selected from nitrogen, oxygen and sulfur, wherein said ring is optionally substituted one or two times, independently, by halogen, $(C_1\text{-}C_4)$alkyl, $(C_1\text{-}C_4)$haloalkyl, amino, $(C_1\text{-}C_4)$alkylamino, $((C_1\text{-}C_4)$alkyl$)((C_1\text{-}C_4)$alkyl)amino, hydroxyl, hydroxy$(C_1\text{-}C_4)$alkyl-, oxo, $(C_1\text{-}C_4)$alkoxy, $(C_1\text{-}C_4)$haloalkoxy, or $(C_1\text{-}C_4)$alkoxy$(C_1\text{-}C_4)$alkyl;
$R^4$ is H;
$R^5$, $R^6$, and $R^7$ are each, independently, H, halogen, nitro, amino, $(C_1\text{-}C_4)$alkylamino, $((C_1\text{-}C_4)$alkyl$)((C_1\text{-}C_4)$alkyl)amino, hydroxyl, or $OR^c$; and
each $R^c$ is, independently, $(C_1\text{-}C_4)$alkyl, pyrrolidinyl, tetrahydrofuranyl, tetrahydrothienyl, piperidinyl, piperazinyl, morpholinyl, tetrahydropyranyl, tetrahydro-4H-1,4-thiazinyl, or 1,4-dioxanyl, wherein said $(C_1\text{-}C_4)$alkyl is optionally substituted by halogen, hydroxyl, trifluoromethyl, $(C_1\text{-}C_4)$alkoxy, amino, $(C_1\text{-}C_4)$alkylamino, $((C_1\text{-}C_4)$alkyl$)((C_1\text{-}C_4)$alkyl)amino, pyrrolidinyl, piperidinyl, piperazinyl, or morpholinyl,
or $R^6$ and $R^7$ taken together represent —O$(C_1\text{-}C_2)$alkylO—.

11. The compound or salt according to claim 1, wherein:
$R^1$ is $(C_1\text{-}C_3$ alkyl);
$R^2$ is H;
$R^3$ is H, halogen, $C_1\text{-}C_6$ alkyl, $C_1\text{-}C_6$ haloalkyl, hydroxy$C_1\text{-}C_6$ alkyl-, $C_1\text{-}C_6$ alkoxy, $(C_3\text{-}C_6)$cycloalkyloxy, $C_1\text{-}C_6$ haloalkoxy, $C_1\text{-}C_6$ alkylthio-, $(C_3\text{-}C_6)$cycloalkylthio-, $C_1\text{-}C_6$ haloalkylthio-, phenyl, 5-membered heteroaryl, or —N($R^a$)($R^b$),
wherein said heteroaryl contains one heteroatom selected from N, O and S, or contains one nitrogen atom and optionally contains 1 additional heteroatom selected from N, O and S, or contains two nitrogen atoms and optionally contains 1 additional heteroatom selected from N, O and S; and said phenyl or heteroaryl is optionally substituted one to three times, independently, by halogen, $(C_1\text{-}C_6)$alkyl, $(C_1\text{-}C_4)$haloalkyl, or —N($R^a$)($R^b$);
each $R^a$ is independently $(C_1\text{-}C_4)$alkyl, wherein said $(C_1\text{-}C_4)$alkyl is optionally substituted by hydroxyl, trifluoromethyl, $(C_1\text{-}C_6)$alkoxy, amino, $(C_1\text{-}C_6)$alkylamino, or $((C_1\text{-}C_6)$alkyl$)((C_1\text{-}C_6)$alkyl)amino, and
$R^b$ is $(C_1\text{-}C_4)$alkyl;
or $R^a$ and $R^b$ taken together with the nitrogen atom to which they are attached form a 5-membered or 6-membered heterocyclic ring, optionally containing one additional heteroatom selected from nitrogen, oxygen and sulfur, wherein said ring is optionally substituted one or two times, independently, by $(C_1\text{-}C_4)$alkyl, $(C_1\text{-}C_4)$haloalkyl, hydroxy$(C_1\text{-}C_4)$alkyl-, oxo, or $(C_1\text{-}C_4)$alkoxy$(C_1\text{-}C_4)$alkyl;
$R^4$ is H;
$R^5$ is H;
$R^6$ and $R^7$ are each $OR^c$ and
each $R^c$ is, independently, $(C_1\text{-}C_4)$alkyl, optionally substituted one to three times, independently, by halogen.

12. A compound selected from:
3-{[6,7-bis(methyloxy)-4-quinazolinyl]amino}-4-(dimethylamino)-N-methylbenzenesulfonamide;
3-{[6,7-bis(methyloxy)-4-quinazolinyl]amino}-N-methylbenzenesulfonamide;
3-{[6,7-bis(methyloxy)-4-quinazolinyl]amino}-N-methyl-4-(4-morpholinyl)benzenesulfonamide;
3-{[6, 7-bis (methyloxy)-4-quinazolinyl]amino}-4-[ethyl(methyl)amino]-N-methylbenzenesulfonamide;
3-{[6,7-bis(methyloxy)-4-quinazolinyl]amino}-N-methyl-4-[(1-methylethyl ) oxy]benzenesulfonamide;
3-{[6,7-bis(methyloxy)-4-quinazolinyl]amino}-N-methyl-4-(methyloxy)benzenesulfonamide;
3-{[6,7-bis(methyloxy)-4-quinazolinyl]amino}-N-methyl-4-(methylthio)benzenesulfonamide;
4-(dimethylamino)-N-methyl-3-(4-quinazolinylamino) benzenesulfonamide;
3-[(6-chloro-4-quinazolinyl)amino]-4-(dimethylamino)-N-methylbenzenesulfonamide;

4-(dimethylamino)-N-methyl-3-{[6-(methyloxy)-4-quinazolinyl]amino}benzenesulfonamide;

3-{[6,7-bis(methyloxy)-4-quinazolinyl]amino}-N-methyl-4-[(2,2,2-trifluoroethyl)oxy]benzenesulfonamide;

3-[(6-chloro-4-quinazolinyl)amino]-N-methyl-4-[(2,2,2-trifluoroethyl)oxy]benzenesulfonamide;

3-(7,8-dihydro[1,4]dioxino[2,3-g]quinazolin-4-ylamino)-4-(dimethylamino)-N-methylbenzenesulfonamide;

3-{[6,7-bis(methyloxy)-4-quinazolinyl]amino}-4-(4,4-difluoro-1-piperidinyl)-N-methylbenzenesulfonamide;

3-[(6-chloro-4-quinazolinyl)amino]-4-(4,4-difluoro-1-piperidinyl)-N-methylbenzenesulfonamide;

3-({7-[(3-chloropropyl)oxy]-4-quinazolinyl}amino)-4-(dimethylamino)-N-methylbenzenesulfonamide;

3-[(6,7-bis{[2-(methyloxy)ethyl]oxy}-4-quinazolinyl)amino]-4-(dimethylamino)-N-methylbenzenesulfonamide;

3-[(6,7-bis{[2-(methyloxy)ethyl]oxy}-4-quinazolinyl)amino]-N-methyl-4-(methyloxy)benzenesulfonamide;

3-[(6,7-bis{[2-(methyloxy)ethyl]oxy}-4-quinazolinyl)amino]-N-methyl-4-[(2,2,2-trifluoroethyl)oxy]benzenesulfonamide;

3-[(6,7-bis{[2-(methyloxy)ethyl]oxy}-4-quinazolinyl)amino]-N-methyl-4-(methylthio)benzenesulfonamide;

3-{[6,7-bis(methyloxy)-4-quinazolinyl]amino}-N-methyl-4-[(2R)-2-(trifluoromethyl)-1-pyrrolidinyl]benzenesulfonamide;

3-[(6-chloro-4-quinazolinyl)amino]-N-methyl-4-[(2R)-2-(trifluoromethyl)-1-pyrrolidinyl]benzenesulfonamide;

5-{[6,7-bis(methyloxy)-4-quinazolinyl]amino}-2-fluoro-N-methylbenzenesulfonamide;

3-{[6,7-bis(methyloxy)-4-quinazolinyl]amino}-N-methyl-4-[(trifluoromethyl)oxy]benzenesulfonamide;

3-{[6,7-bis(methyloxy)-4-quinazolinyl]amino}-N-methyl-4-(1-piperidinyl)benzenesulfonamide;

3-[(6-chloro-4-quinazolinyl)amino]-N-methyl-4-(1-piperidinyl)benzenesulfonamide;

3-{[6,7-bis(methyloxy)-4-quinazolinyl]amino}-4-(2,5-dimethyl-1-pyrrolidinyl)-N-methylbenzenesulfonamide;

3-[(6-chloro-4-quinazolinyl)amino]-4-(2,5-dimethyl-1-pyrrolidinyl)-N-methylbenzenesulfonamide;

3-{[6,7-bis(methyloxy)-4-quinazolinyl]amino}-N-methyl-4-[(2,2,2-trifluoroethyl)thio]benzenesulfonamide;

3-{[5,7-bis(methyloxy)-4-quinazolinyl]amino}-N-methylbenzenesulfonamide;

3-{[5,7-bis(methyloxy)-4-quinazolinyl]amino}-N-methyl-4-[(2,2,2-trifluoroethyl)oxy]benzenesulfonamide;

3-{[5,7-bis(methyloxy)-4-quinazolinyl]amino}-4-(dimethylamino)-N-methylbenzenesulfonamide;

3-(5-chloro-6,7-dimethoxyquinazolin-4-ylamino)-N-methylbenzenesulfonamide;

4-methoxy-3-(7-methoxy-6-(3-morpholinopropoxy)quinazolin-4-ylamino)-N-methylbenzenesulfonamide;

3-{[6,7-bis(methyloxy)-4-quinazolinyl]amino}-N-methyl-4-[methyl(2,2,2-trifluoroethyl)amino]benzenesulfonamide;

3-{[5,7-bis(methyloxy)-4-quinazolinyl]amino}-N-methyl-4-[methyl(2,2,2-trifluoroethyl)amino]benzenesulfonamide;

3-{[5,7-bis(methyloxy)-4-quinazolinyl]amino}-N-methyl-4-(methyloxy)benzenesulfonamide;

3-{[5,7-bis(methyloxy)-4-quinazolinyl]amino}-4-fluoro-N-methylbenzenesulfonamide;

3-{[5,7-bis(methyloxy)-4-quinazolinyl]amino}-4-chloro-N-methylbenzenesulfonamide;

3-{[5,7-bis(methyloxy)-4-quinazolinyl]amino}-N-methyl-4-(4-morpholinyl)benzenesulfonamide;

5-{[6,7-bis(methyloxy)-4-quinazolinyl]amino}-2-fluoro-N-methyl-4-(methyloxy)benzenesulfonamide;

3-{[6-(ethyloxy)-7-(methyloxy)-4-quinazolinyl]amino}-N-methyl-4-[(2,2,2-trifluoroethyl)oxy]benzenesulfonamide;

4-(dimethylamino)-3-(7-methoxy-6-(3-morpholinopropoxy)quinazolin-4-ylamino)-N-methylbenzenesulfonamide;

N-methyl-3-{[6-[(1-methylethyl)oxy]-7-(methyloxy)-4-quinazolinyl]amino}-4-[(2,2,2-trifluoroethyl)oxy]benzenesulfonamide;

3-({7-[(3-chloropropyl)oxy]-4-quinazolinyl}amino)-N-methyl-4-[(2,2,2-trifluoroethyl)oxy]benzenesulfonamide;

3-{[5-(ethyloxy)-7-(methyloxy)-4-quinazolinyl]amino}-N-methyl-4-[(2,2,2-trifluoroethyl)oxy]benzenesulfonamide;

N-methyl-3-{[5-[(1-methylethyl)oxy]-7-(methyloxy)-4-quinazolinyl]amino}-4-[(2,2,2-trifluoroethyl)oxy]benzenesulfonamide;

N-methyl-4-[(2,2,2-trifluoroethyl)oxy]-3-{[5,6,7-tris(methyloxy)-4-quinazolinyl]amino}benzenesulfonamide;

3-{[5,7-bis(methyloxy)-4-quinazolinyl]amino}-N-methyl-4-[(2,2,2-trifluoro-1-methylethyl)oxy]benzenesulfonamide;

5-{[5,7-bis(methyloxy)-4-quinazolinyl]amino}-2-fluoro-N-methyl-4-[(2,2,2-trifluoroethyl)oxy]benzenesulfonamide;

5-{[5,7-bis(methyloxy)-4-quinazolinyl]amino}-2-fluoro-N-methyl-4-(methyloxy)benzenesulfonamide;

5-{[6,7-bis(methyloxy)-4-quinazolinyl]amino}-2-fluoro-N-methyl-4-[(2,2,2-trifluoroethyl)oxy]benzenesulfonamide;

3-{[5,7-bis(methyloxy)-4-quinazolinyl]amino}-N-methyl-4-(methylthio)benzenesulfonamide;

3-{[5,7-bis(methyloxy)-4-quinazolinyl]amino}-N-methyl-4-[(trifluoromethyl)oxy]benzenesulfonamide;

N-methyl-4-[(trifluoromethyl)oxy]-3-{[5,6,7-tris(methyloxy)-4-quinazolinyl]amino}benzenesulfonamide;

5-{[5,7-bis(methyloxy)-4-quinazolinyl]amino}-4-(dimethylamino)-2-fluoro-N-methylbenzenesulfonamide;

5-{[6,7-bis(methyloxy)-4-quinazolinyl]amino}-4-(dimethylamino)-2-fluoro-N-methylbenzenesulfonamide;

2-fluoro-N-methyl-4-[(2,2,2-trifluoroethyl)oxy]-5-{[5,6,7-tris(methyloxy)-4-quinazolinyl]amino}benzenesulfonamide;

4-chloro-N-methyl-3-{[5,6,7-tris(methyloxy)-4-quinazolinyl]amino}benzenesulfonamide;

N-methyl-3-[(7-(methyloxy)-5-{[2-(methyloxy)ethyl]oxy}-4-quinazolinyl)amino]-4-[(2,2,2-trifluoroethyl)oxy]benzenesulfonamide;

N-methyl-3-{[7-(methyloxy)-5-(tetrahydro-2H-pyran-4-yloxy)-4-quinazolinyl]amino}-4-[(2,2,2-trifluoroethyl)oxy]benzenesulfonamide;

N-methyl-4-[(2,2,2-trifluoro-1-methylethyl)oxy]-3-{[5,6,7-tris(methyloxy)-4-quinazolinyl]amino}benzenesulfonamide;

N-methyl-4-(methylsulfonyl)-3-{[5,6,7-tris(methyloxy)-4-quinazolinyl]amino}benzenesulfonamide;

3-{[5-(ethyloxy)-7-(methyloxy)-4-quinazolinyl]amino}-N-methyl-4-[(trifluoromethyl)oxy]benzenesulfonamide;

N-methyl-3-{[5-[(1-methylethyl)oxy]-7-(methyloxy)-4-quinazolinyl]amino}-4-[(trifluoromethyl)oxy]benzenesulfonamide;

3-{[5-(ethyloxy)-7-(methyloxy)-4-quinazolinyl]amino}-N-methyl-4-[(2,2,2-trifluoro-1-methylethyl)oxy]benzenesulfonamide;

N-methyl-3-{[5-[(1-methylethyl)oxy]-7-(methyloxy)-4-quinazolinyl]amino}-4-[(2,2,2-trifluoro-1-methylethyl)oxy]benzenesulfonamide;

3-{[6,7-bis(methyloxy)-4-quinazolinyl]amino}-N-methyl-4-(methylsulfonyl)benzenesulfonamide;

3-{[6,7-bis(methyloxy)-4-quinazolinyl]amino}-N-methyl-4-[(2,2,2-trifluoro-1-methylethyl)oxy]benzenesulfonamide;

3-{[6-iodo-7-(methyloxy)-4-quinazolinyl]amino}-N-methyl-4-[(2,2,2-trifluoroethyl)oxy]benzenesulfonamide;

3-{[6,7-bis(ethyloxy)-4-quinazolinyl]amino}-N-methyl-4-[(2,2,2-trifluoroethyl)oxy]benzenesulfonamide;

4-(dimethylamino)-N-methyl-3-((7-nitroquinazolin-4-yl)amino)benzenesulfonamide;

4-(dimethylamino)-N-methyl-3-[(7-{[3-(4-morpholinyl)propyl]oxy}-4-quinazolinyl)amino]benzenesulfonamide;

N-methyl-3-[(7-{[3-(4-morpholinyl)propyl]oxy}-4-quinazolinyl)amino]-4-[(2,2,2-trifluoroethyl)oxy]benzenesulfonamide;

N-methyl-3-[(7-{[3-(methyloxy)propyl]oxy}-4-quinazolinyl)amino]-4-[(2,2,2-trifluoroethyl)oxy]benzenesulfonamide;

4-(dimethylamino)-N-methyl-3-[(7-{[3-(methyloxy)propyl]oxy}-4-quinazolinyl)amino]benzenesulfonamide;

3-{[5,7-bis(methyloxy)-4-quinazolinyl]amino}-N-methyl-4-(methylsulfonyl)benzenesulfonamide;

3-(7-hydroxy-6-methoxyquinazolin-4-ylamino)-N-methyl-4-(2,2,2-trifluoroethoxy)benzenesulfonamide;

3-(7-isopropoxy-6-methoxy-quinazolin-4-ylamino)-N-methyl-4-(2,2,2-trifluoro-ethoxy)-benzenesulfonamide;

3-(7-ethoxy-6-methoxy-quinazolin-4-ylamino)-N-methyl-4-(2,2,2-trifluoro-ethoxy)-benzenesulfonamide;

3-[6-methoxy-7-(2-methoxy-ethoxy)-quinazolin-4-ylamino]-N-methyl-4-(2,2,2-trifluoro-ethoxy)-benzenesulfonamide;

3-{[5,7-bis(methyloxy)-4-quinazolinyl]amino}-N-methyl-4-[(2,2,2-trifluoro-1-methylethyl)oxy]benzenesulfonamide;

3-{[5,7-bis(methyloxy)-4-quinazolinyl]amino}-N-methyl-4-[(2,2,2-trifluoro-1-methylethyl)oxy]benzenesulfonamide;

3-((6-aminoquinazolin-4-yl)amino)-4-(dimethylamino)-N-methylbenzenesulfonamide;

3-((7-aminoquinazolin-4-yl)amino)-4-(dimethylamino)-N-methylbenzenesulfonamide;

4-(dimethylamino)-3-((6-(dimethylamino)quinazolin-4-yl)amino)-N-methylbenzenesulfonamide;

4-(dimethylamino)-N-methyl-3-((6-(methylamino)quinazolin-4-yl)amino)benzenesulfonamide; and 4-(dimethylamino)-N-methyl-3-((7-(methylamino)quinazolin-4-yl)amino)benzenesulfonamide;

or a pharmaceutically acceptable salt thereof.

13. A pharmaceutical composition comprising the compound or salt according to claim 1 and a pharmaceutically-acceptable excipient.

14. A method of inhibiting TNNI3K comprising contacting TNNI3K with the compound or salt according to claim 1.

15. A method for treating congestive heart failure comprising administering to a patient in need thereof an effective amount of the compound or salt according to claim 1.

16. A method for treating congestive heart failure comprising administering to a patient in need thereof the pharmaceutical composition according to claim 13.

* * * * *